ic double-strand|ed barcode|US011339208B1

(12) United States Patent
Mauzy et al.

(10) Patent No.: US 11,339,208 B1
(45) Date of Patent: May 24, 2022

(54) **CAMELIDAE SINGLE-DOMAIN ANTIBODIES AGAINST *YERSINIA PESTIS* AND METHODS OF USE**

(71) Applicant: Government of the United States as Represented by the Secretary of the Air Force, Wright-Patterson AFB, OH (US)

(72) Inventors: Camilla A Mauzy, Enon, OH (US); Serge Victor Marie Muyldermans, Brussels (BE)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 237 days.

(21) Appl. No.: 16/023,723

(22) Filed: Jun. 29, 2018

Related U.S. Application Data

(63) Continuation of application No. 13/906,386, filed on May 31, 2013, now abandoned.

(51) Int. Cl.
  *C07K 16/12* (2006.01)
(52) U.S. Cl.
  CPC ................................. *C07K 16/1228* (2013.01)
(58) Field of Classification Search
  None
  See application file for complete search history.

(56) References Cited

PUBLICATIONS

Skolnick et al. (Trends in Biotechnology 18: 34-39, 2000) (Year: 2000).*
Greenspan et al.,(Nature Biotechnology 17:936-937, 1999) (Year: 1999).*
Colman et al. (Research in Immunology 145: 33-36, 1994) (Year: 1994).*
Houghten et al. (New Approaches to Immunization, Vaccines 86, Cold Spring Harbor Laboratory, p. 21-25, 1986) (Year: 1986).*
Giusti et al. (Proc. Natl. Acad. Sci. USA. May 1987 ; 84 (9): 2926-2930) (Year: 1987).*
Winkler et al (J. Imm., 265:4505-4514, 2000) (Year: 2000).*
Chien et al. (Proc. Natl. Acad. Sci. USA. Jul. 1989; 86 (14): 5532-5536) (Year: 1989).*
Caldas et al. (Mol. Immunol. May 2003; 39 (15): 941-952) (Year: 2003).*
Casadevall et al. (PNAS vol. 109 No. 31, pp. 12272-12273) (Year: 2012).*

* cited by examiner

*Primary Examiner* — Robert A Zeman
(74) *Attorney, Agent, or Firm* — AFMCLO/JAZ; Chastity D Whitaker

(57) ABSTRACT

Single-domain antibodies (SAbs) against three *Yersinia pestis* surface proteins (LcrV, YscF, and F1), nucleic acid sequences encoding the SAbs, and polypeptides comprising two or more SAbs capable of recognizing two or more epitopes and/or antigens. The present invention further includes methods for preventing or treating *Y. pestis* infections in a patient; methods for detecting and/or diagnosing *Y. pestis* infections; and devices and methods for identifying and/or detecting *Y. pestis* on a surface and/or in an environment.

2 Claims, 32 Drawing Sheets

Specification includes a Sequence Listing.

```
SEQ
ID NO
154: QVQLQESGGGLVQAGGSLRLSCAASGRTWRA---YYMGWFRQAPGKEREFVAVMSRSGGTTSYADSVKG   : 66
155: QVQLQESGGGLVQAGGSLRLSCVASGRAFSN---YAMAWFRQAPGKEREFVAANWRSGGLTDYADSVKG   : 66
156: QVQLQESGGGLVQAGGSLRLSCAVSGRTFSR---YAMGWFRQAPGKEREFVAAISWSGSTYYADSVKG   : 66
157: QVQLQESGGGLVQAGGSLKLSCTASQRTFSR---YSLGWFRQAPGEERVFVAATTWSGISSDYADSVKG   : 66
158: QVQLQESGGGLVQAGGSLRLSCAASGRTFSS---HAMAWFRQGPGEERQFLAAIRWNGDNIHYSDSAKG   : 66
159: QVQLQESGGGLVQAGDSRILSCTASGRTFGRPFRYTMGWFRRAPGKEREFVGGITRSGNNIYYSDSVKG   : 69
160: QVQLQESGGGLVQAGGSLRLACAASGETVDD---LAIGWFRQAPGKEREEISCISGSDGSTYYADSLSG   : 66

154: RFTISRDNAKNTVYLQMNNLAPEDTATYYCKAGGG--MYG-PDLYGMTYWGKGTQVTVSS
155: RFTISRDDAKNTVYLQMNSLKPEDTAVYYCAAGGGSRWYGRTTASWYDYWGQGTQVTVSS
156: RFTISRDHAKNVMYLQMNGLKPEDTGVYVCARP-----AYGLRP-PYNYRGQGTQVTVSS
157: RFTISRDNAKNTGYLQMNNLKPEDTGVYYCAAGRSSWFAPWLTPYEYDYWGRGTQVTVSS
158: RFTISRDLAKNTLYLQMNSLKPEDTAVYYCARG------------VYDYWGQGTQVTVSS
159: RFTISRDNAKNTVYLQMNSLKPEDTAVYYCNADWG---------WRNYWGQGTQVTVSS
160: RFTISRDNVKNTVYLQMNSLKLEDTAVYYCYAEIYD------RRWYRNDYWGQGTQVTVSS
```

FIG. 10

| SEQ ID NO | | |
|---|---|---|
| 168: | QVQLQESGGGLVQAGGSLRLSCAVSGMMYIREAIRWYRQAPGKQREWVAFVSSTGN-PRYTDSVKG | 65 |
| 169: | QVQLQESGGGLVQPGGSLRLSCAVSGMMYIRYTMRWYRQAPGKQREWVAVVSSTGN-PHYADSVKG | 65 |
| 170: | QVQLQESGGGLVRPGGSLRLSCAVSGRAVNRYHMHWYRQAPGKQREWVTFISVGGT-TNYAGSVKG | 65 |
| 171: | QVQLQESGGGSVQPGGSLSLSCSASGIIFSDYALTWYRQAPGKQREWVAQITRSQN-INYTGSVKG | 65 |
| 172: | QVQLQESGGGSVQPGGSLSLSCSASGIIFSDYALTWYRQAPGKQREWVAQITRSQN-INYTGSVKG | 65 |
| 173: | QVQLQESGGGLVQPGGSLSLSCSASGIIFSDYALTWYRQAPGKQREWVAQITRSQN-INYTGSVKG | 65 |
| 174: | QVQLQESGGGLVQPGGSLSLSCSASGIIFSDYALTWYRQAPGKQREWVAQITRRQN-INYTGSVKG | 65 |
| 175: | QVQLQESGGGLVQPGGSLSLSCSASGIIFSDYALTWYRQAPGKQREWVAQITRSQN-INYTGSVKG | 65 |
| 176: | QVQLQESGGGLVQPGGSLRLSCAASARIFSIYAMVWYRQAPGKQREWVAAITTGGT-TNYADSVKG | 65 |

| 168: | RFTISRDNAKNTVYLQMNSLTPEDTAVYYCNTYLG-SRDYWGQGTQVTVSS |
|---|---|
| 169: | RFTISRDNAKNTVYLQMNSLTPEDTAVYYCNTYLG-SRDYWGQGTQVTVSS |
| 170: | RFTVSRDNAKNTLYLQMNSLKPEDTAVYYCNS----AEYWGQGTQVTVSS |
| 171: | RFTVSRDNAKNTVHLQMNSLKPEDTAVYYCHAYDGRRPPYWGQGTQVTVSS |
| 172: | RFTVSRDNAKNTVHLQMNSLKPEDTAVYYCHAYDGRRRTYWGQGTQVTVSS |
| 173: | RFTVSRDNAKNTVHLQMNSLKPEDTAVYYCHAYDGRRPPYWGQGTQVTVSS |
| 174: | RFTVSRDNAKNTVHLQMNSLKPEDTAVYYCHAYDGRRSPYWGQGTQVTVSS |
| 175: | RFTVSRDNAKNTVHLQMNSLKPEDAAVYYCHAYDGRRPPYWGQGTQVTVSS |
| 176: | RFTVSRDNAKNTVYLQMNSLKPEDTAVYYCNAPG-----YWGQGTQVTVSS |

FIG. 11A

| SEQ ID NO | Sequence | |
|---|---|---|
| 177: | QVQLQESGGGLVQPGGSLRLSCAASGVIASISVLRWYRQTPGKTRDWVAIITSGGN-TRYADSVKG | : 65 |
| 178: | QVQLQESGGGLVRPGGSLRLSCEASGTTFRSLVMKWYRQAPGKEREWVAFISSPGDRTRYTEAVKG | : 66 |
| 179: | QVQLQESGGGLVQSGDSLRLSCAASGFTFSNYAMSWVRQAPGKGLEWVSTINSGGSTSYAYSVKG | : 66 |
| 180: | QVQLQESGGGLVQPGGSLRLSCAASGFTFSNYAMSWVRQAPGKGLEWVSTINIGGSTSYADSVKG | : 66 |
| 181: | QVQLQESGGGLVQPGGSLRLSCAASGFTFRNYAMSWVRQAPGKGLEWVSTINGGGITSYADSVKG | : 66 |
| 182: | QVQLQESGGGLVQPGGSLRLSCAASGFTFSSYAMSWVRLAPGKGLEWVSTINIAGGITSYADSVKG | : 66 |
| 183: | QVQLQESGGGLVQPGGSLRLSCAASGFTFSSYAMSWVRQAPGKGLEWVSTINMGGTTSYADSVKG | : 66 |
| 184: | QVQLQESGGGLVQPGGSLRLSCAASGFTFSTSAMSWIRQPPGKAREVVATITSAGGSISYVNSVKG | : 66 |
| 185: | QVQLQESGGGLVQPGGSLRLSCAASGFTFSTNAMSWIRQPPGKAREVVATITSAGGSISYVNSVKG | : 66 |

| SEQ ID NO | Sequence |
|---|---|
| 177: | RFTVSRDNARNTVYLQMNSLKPEDTAVYYCNTLVG-AKDYWGQGTQVTVSS |
| 178: | RFTVSRDNAKNALYLQMNGLKPEDTAVYYCNAN----GIYWGKGTQVTVSS |
| 179: | RFTVSRDNAKNTLYLQMNSLKPEDTAVYYCAKTA--SHIPLSQGTQVTVSS |
| 180: | RFTVSRDNAKNTLYLQMNSLKPEDTAVYYCAKTA--SHIPLSQGTQVTVSS |
| 181: | RFTVSRDNAKNTMYLQMNSLKPEDTAVYYCAQTARDSRDSRGQGTQVTVSS |
| 182: | RFTVSRDNAKNTLYLQMNSLKPEDTAVYYCAKTAANWSAQRGQGTQVTVSS |
| 183: | RFTVSRDNAKNTLYLQMNSLKPEDTAVYYCAKTAGNWSAQRGQGTQVTVSS |
| 184: | RFTVSRDNAKNTLYLQMNMLKPEDTAVYYCARLVN--LAQTGQGTQVTVSS |
| 185: | RFTVSRDNAKNTLYLQMNMLKPEDTAVYYCARLVN--LAQTGQGTQVTVSS |

FIG. 11B

| SEQ ID NO: | Sequence | |
|---|---|---|
| 204: | QVQLQESGGGMVEPGGSLRLSCAASGFRFSSYAMSWVRQAPGKGLERVSAINSDGDKTSYADSVKG | 66 |
| 205: | QVQLQESGGGLVEPGGSLRLSCAASGFRFSSYAMSWVRQAPGKGLERVSAINSDGDKTSYADSVKG | 66 |
| 206: | QVQLQESGGGMVEPGGSLRLSCAASGFRFSSYAMSWVRQAPGKGLERVSAINSDGDKTSYADSVKG | 66 |
| 207: | QVQLQESGGGLVQSGESLRLSCAASGLRFSSYAMSWVRQAPGKGLERVSAINSDGDKTSYADSVKG | 66 |
| 208: | QVQLQESGGGLVQPGGSLKLSCAASGFTFNWYTMAWYRQVPGEERKMVATITGASGDTKYADSVKG | 66 |
| 209: | QVQLQESGGGLVRPGGSLKLSCAASGFTFNWYTMAWYRQVPGEERKMVATITGASGDTKYADSVKG | 66 |
| 210: | QVQLQESGGGSVQPGGSLKLSCAASGFTFNWYTMAWYRQVPGEERKMVATITGASGDTKYADSVKG | 66 |
| 211: | QVQLQESGGGSVQPGGSLKLSCAASGFTFNWYTMAWYRQVPGEERKMVATITGASGDTKYADSVKG | 66 |
| 212: | QVQLQESGGGFVQPGGSLKLSCAASGFTFNWYTMAWYRQVPGEERKMVATITGASGDTKYADSVKG | 66 |
| 213: | QVQLQESGGGLVQPGGSLKLSCAASGFTFNWYTMAWYRQVPGEERKMVATITGASGDTKYADSVKG | 66 |
| 214: | QVQLQESGGGLVQPGGSLGLSCAASGSLLNIYAMGWYRQAPGRQRELVATVT-SSGTAEYADSVKG | 65 |
| 215: | QVQLQESGGGLVQPGGSLRLSCAASGGTLGYYAIGWFRQAPGKEREAVSCITSSDTSAYYADSAKG | 66 |
| 216: | QVQLQESGGGLVQPGGSTRLSCAASGFTLDIYAIGWFRQAPGKEHEGVSWIVGNDGRTYIDSVKG | 66 |
| 217: | QVQLQESGGGLVQPGGSLILSCTISGASLRDRRVTWSRQGPGKSLEIIAVMAPDYG-VHYFGSLEG | 65 |

FIG. 12A

| SEQ ID NO | | |
|---|---|---|
| 204: | RFTISRDNARNTLYLQMSNLKPEDTAVYYCADR--DLYCSGSMCKDVLGGARYDFRGQGTQVTVSS |
| 205: | RFTISRDNARNTLYLQMSNLKPEDTAVYYCADR--DLYCSGSMCKDVLGGARYDFRGQGTQVTVSS |
| 206: | RFTISRDNARNTLYLQMNNLKPEDTAVYYCADR--DLYCSGSMCKDVLGGARYDFRGQGTQVTVSS |
| 207: | RFTISRDNARNTLYLQMSNLKPEDTAVYYCADR--DLYCSGSMCKDVLGGARYDFRGQGTQVTVSS |
| 208: | RFTISRDNAKNTVTLQMNSLKPGDAAVYYCHA---YLTYDSGSVKG------VNYWGQGTQVTVSS |
| 209: | RFTISRDNAKNTVTLQMNSLKPGDTAVYYCHA---YLTYDSGSVKG------VNYWGQGTQVTVSS |
| 210: | RFTISRDNAKNTVTLQMNSLKPGDTAVYYCHA---YLTYDSGSVKG------VNYWGQGTQVTVSS |
| 211: | RSTISRDNAKNTVTLQMNSLKPGDTAVYYCHA---CLTYDSGSVKG------VNYWGQGTQVTVSS |
| 212: | RFTISRDNAKNTVTLQMNSLKPGDTAVYYCHA---YLTYDSGSVKG------VNYWGQGTQVTVSS |
| 213: | RFTISRDNAKNTVTLQMNSLKPGDTAVYYCHA---YLTYDSGSAKG------VNYWGQGTQVTVSS |
| 214: | RFTISRDNAKNTVYLQMNSLRPEDTGVYYCNA---HLRYG-DYVRGPPE---YNYWGQGTQVTVSS |
| 215: | RFTISRDNAKNTMYLQMNNLKPEDTAVYYCAAGYYFRDYSDSYYTGTG---MKVWGKGTQVTVSS |
| 216: | RFTISRDNAKNTVYLEMNSLKPEDTAVYYCAAKFWPRYYSGRPPVGRDG---YDYWGQGTQVTVSS |
| 217: | RVAVRGDVVKNTVYLQVNALKPEDTAIYWCSMG-----------------NIRGLGTQVTVSS |

FIG. 12B

```
SEQ
ID NO
165:  CAGGTGCAGCTGCAGGAGTCTGGGGGAGGATTGGTGCAGCCTGGGGCTCTCTGAGACTCTCCTGTGCAGCCTC
166:  CAGGTGCAGCTGCAGGAGTCTGGGGGAGGATTGGTGCAGCCTGGGGACTCTCGGATATCTCCTGTACAGCCTC
161:  CAGGTGCAGCTGCAGGAGTCTGGGGGAGGATTGGTGCAGCCTGGGGGCTCTCTGAGACTCTCCTGTGCAGCCTC
167:  CAGGTGCAGCTGCAGGAGTCTGGGGGAGGCTTGGTGCAGCCTGGGGGGTCTCTGAGACTCTCGCCTGTGCAGCCTC

165:  TGGACGCACCTTCAGTAGCC------ATGCCATGCCTGGTTCCGCCAGGGTCCAGGGAGAGGAGCGTCAGT
166:  TGGACGCACCTTTGGACGCCCCCTTCAGATATACCATGGGCTGGTTCCGCCGGGCTCCAGGGAAGGAGCGTGAGT
161:  TGGACGCACCTGGAGAGCCT------ATTACATGGGCTGGTTCCGCCAGGCTCCAGGGAAGGAGCGTGAGT
167:  TGGAGAGACTGTCGATGATC------TTGCCATCGGCTGGTTCCGCCAGCCCCAGGGAAGGAGCGTGAGG

165:  TTCTAGCAGCTATTAGATGGAATGGTGATAACATACACTATTCAGACTCCGTGAAGGGCCGATTCACCATCTCC
166:  TTGTAGGAGGTATTACAAGAAGTGGTAATAATATATACTATTCAGACTCCGTGAAGGGCCGATTCACCATCTCC
161:  TTGTAGCAGTTATGAGTCGGAGCGGTGGCACCATCCTATGCGACTCCGTGAAGGGCCGATTCACCATCTCC
167:  AGATTTCATGTATTAGTGGTAGTGGTGATGGTAGCACATACTATGCAGACTCCGTGCGGGCCGATTCACCATCTCC
```

FIG. 15A

| SEQ ID NO | | |
|---|---|---|
| 165: | AGAGACCTCGCCAAGAACACGCTCTATCTGCAAATGAACAGCCTGAAACCTGAGGACACGGCCGTGTATTACTG |
| 166: | AGAGACAACGCCAAGAACACGGTGTATCTCCAAATGAACAGCCTGAAACCTGAGGACACGGCCGTGTATTATTG |
| 161: | AGAGACAACGCCAAGAACACGGTGTATCTACAAATGAACAACCTGGCACCTGAGGACACGGCCACGTATTATTG |
| 167: | AGGGACAACGTCAAGAACACGGTGTATCTGCAAATGAACAGCCTGAAACTTGAGGACACGGCCGTCTATTACTG |
| 165: | T---GCAAG-----------GGGGGT--GTA------------TGA-CTACTGGGCCAGGGGACC |
| 166: | TAACGCAGAT----------TGGGGGT--GGA------------GGAACTACTGGGGCCAGGGGACC |
| 161: | TAAGGCGGGGGGCGGAATGTAC-GGGCCGGACCTGTA--------T-GGTATGACATACTGGGGCAAAGGGACC |
| 167: | TTATGCAGAG------ATTTAC-GATAGACGCTGGTA--------TCGGAACGAC-TACTGGGGCCAGGGGACC |
| 165: | CAGGTCACCGTCTCCCAGCGGCCGCTACCCGTACGACGTTCCGGACTACGGTTCCGGCCGAGCATAG |
| 166: | CAGGTCACCGTCTCCAGCGGCCGCTACCCGTACGACGTTCCGGACTACGGTTCCGGCCGAGCATAG |
| 161: | CAGGTCACCGTCTCCAGCGGCCGCTACCCGTACGACGTTCCGGACTACGGTTCCGGCCGAGCATAG |
| 167: | CAGGTCACCGTCTCCAGCGGCCGCTACCCGTACGACGTTCCGGACTACGGTTCCGGCCGAGCATAG |

FIG. 15B

| SEQ ID NO | |
|---|---|
| 162: | CAGGTGCAGCTGCAGGAGTCTGGAGGAGGATTGGTACAGGCTGGGGCTCTCTGAGACTCTCCTGTGTAGCCTC |
| 163: | CAGGTGCAGCTGCAGGAGTCTGGGGGAGGATTGGTGCAGGCTGGGGCTCTCTGAGACTCTCCTGTGCAGTCTC |
| 164: | CAGGTGCAGCTGCAGGAGTCTGGGGGAGGATTGGTGCAGGCTGGGGCTCTGGGGCTCTCTGAAACTCTCCTGCACAGCCTC |
| | |
| 162: | TGGACGCGCCTTCAGTAATT------ATGCGATGGCCTGGTTCCGCCAGGCTCCAGGAAGGAGCGTGAGT |
| 163: | TGGACGCACCTTCAGTAGAT------ATGCCATGGGCTGGTTCCGCCAGGCTCCAGGAAGGAGCGTGAGT |
| 164: | TCAACGCACCTTCAGTCGCT------ATAGCTTGGGCTGGTTCCGCCAGGCTCCAGGTGAGGAGCGTGTTT |
| | |
| 162: | TTGTAGCAGCTAATTGGCGGAGTGGTGGTCTTACAGACTATGCAGACTCCGTGAAGGGCCGATTCACCATCTCC |
| 163: | TTGTAGCAGCTATTAGCTGGAGTGGTAGTAGCACATATTATGCAGACTCCGTGAAGGGCCGATTCACCATCTCC |
| 164: | TTGTAGCCGCTACTACATGGAGTGGTATAAGCAGTGGTACTAGCAGACTCCGTGAAGGGCCGATTCACCATCTCC |
| | |
| 162: | AGAGACGACGCCAAGAACACGGTGTATCTGCAAATGAACAGCCTGAAACCTGAGGACACGGCCGTTTATTACTG |
| 163: | AGAGACCACGCCAAGAACGTGATGTATCTGCAAATGAACGGCCTGAAACCTGAGGACACGGGTGTGTTTATGTCTG |
| 164: | AGAGACAACGCCAAGAACACGGGTATCTGCAAATGAACAATTTAAAACTGAGGACACGGGCGTTTATTACTG |
| | |
| 162: | TGCCGCCGGGGGCGGTAGTCGCTGGTACGGGCGAACAACCGCAAGTTGGTATGAC-TACTGGGGCCAGGGGACC |
| 163: | TGCCA--AGACCAGCTACGGACTCCGCCCCCG-------TATAAT-TACCGGGGCCAGGGGACC |
| 164: | TGCAGCAGGACGTAGTAGCTGGTTCGCCCCCTGTTGACCCCCTATGAGTATGAT-TATTGGGGCCGGGGGACC |
| | |
| 162: | CAGGTCACCGTCTCCAGCGGCCGCTACCCGTACCCGTACGACGTTCCGGCCGAGCATAG |
| 163: | CAGGTCACCGTCTCCAGCGGCCGCTACCCGTACGACGTTCCGGCCGAGCATAG |
| 164: | CAGGTCACCGTCTCCAGCGGCCGCTACCCGTACGACGTTCCGGCCGAGCATAG |

FIG. 15C

| SEQ ID NO | | | |
|---|---|---|---|
| 195: | CAGGTGCAGCTGCAGGAGTCTGGGGGAGGCTTGGTGCAGCCTGGGGGGTCTCTGAGACTCTCCTGTGCAGCCTC | TGGAGTCATCGCCAGTATCTCCGTCCTGCGCTGGTACCGCCAAACACCAGGAAAGACGCGCGACTGGTCGCAA | TTATTACTAG---TGGTGGCAACACACGCTATGCAGACTCCGTGAAGGGCCGATTCACCACCTCCAGAGATAAC |
| 194: | CAGGTGCAGCTGCAGGAGTCTGGGGGAGGCTTGGTGCAGCCTGGGGGGTCTCTGAGACTCTCCTGTGCAGCCTC | TGCCCGCATCTTCAGTATCTATGCCATGGTATGGTACCGCCAGGCTCCAGGGAAGCAGCGCGAGTGGGTCGCAG | CTATTACTAC---TGGTGGTACCACAAACTATGCAGACTCCGTGAAGGGCCGATTCACCATCTCCAGAGACAAC |
| 186: | CAGGTGCAGCTGCAGGAGTCTGGGGGAGGCTTGGTGCAGCCTGGGGGGCTCTCTGAGACTCTCCTGTGCAGTTTC | TGGAATGATGATGTACATTAGGAGGCTATACGCTGGTACCGCCAGGCTCCAGGGAAGCAGCGCGAGTGGGTCGCCT | TTGTAAGTAG---TACTGGTAATCCACGCTATACAGACTCCGTGAAGGGCCGATTCACCATCTCCAGAGACAAC |
| 187: | CAGGTGCAGCTGCAGGAGTCTGAGAGGCTTGGTGCAGCCTGGGGGGTCTGGGCAGCTCTCCTGTGCAGTTTC | TGGAATGATGATGTACATTAGGTACACTATGGTACCGCCAGGCTCCAGGGAAGCAGCGCGAGTGGGTCGCCG | TTGTAAGTAG---TACTGGTAATCCACACTATGCAGACTCCGTGAAGGGCCGATTCACCATCTCCAGAGACAAC |
| 188: | CAGGTGCAGCTGCAGCTGCAGGAGTCTGGGGGAGGCTTGGTGCGGCCTTGGTGCGGCCTTGCAGCTCTCCTGTGCAGTCTC | TGGAAGAGCCGTCAATAGTTATCACATGGTATCACATGCACTGTGGTACCGCCAGGCTCCAGGGAAGCAGCGCGAGTGGGTCACAT | TTATTAGTGT---TGGTGGTACCACCAAACTATGCAGGCTCCGGAAGGGCCGATTCACCGTCCCCGAGACAAC |

FIG. 16A

| SEQ ID NO | | | |
|---|---|---|---|
| 195: | GCCAGGAACACGGTGTATCTGCAAATGAACAGCCTGAGGACACGGCCGTCTATTACTGTAATACACT | TGTAGGAGCCAA----GGACTACTGGGGCCAGGGGACCCAGGTCACCGTCTCCCAGCGGCCGCTACCCGTACGAC | GTTCCGGACTACGGTTCCGGCCCGAGCATAG |
| 194: | GCCAAGAACACGGTGTATCTGCAAATGAACAGCCTGAGGACACGGCCGTCTATTACTGTAATGCTCC | -----------GGGCTACTGGGGCCAGGGGACCCAGGTCACCGTCTCCCAGCGGCCGCTACCCGTACGAC | GTTCCGGACTACGGTTCCGGCCCGAGCATAG |
| 186: | GCCAAGAACACGGTGTATCTGCAAATGAACAGCCTGACACCTGAGGACACGGCCGTCTATTACTGTAATACATA | CTTGGGCTCGAG----GGACTACTGGGGCCAGGGGACCCAGGTCACCGTCTCCCAGCGGCCGCTACCCGTACGAC | GTTCCGGACTACGGTTCCGGCCCGAGCATAG |
| 187: | GCCAAGAACACGGTGTATCTGCAAATGAACAGCCTGACACCTGAGGACACGGCCGTCTATTACTGTAATACATA | CTTGGGCTCGAG----GGACTACTGGGGCCAGGGGACCCAGGTCACCGTCTCCCAGCGGCCGCTACCCGTACGAC | GTTCCGGACTACGGTTCCGGCCCGAGCATAG |
| 188: | GCCAAAAACACGCTGTATCTGCAAATGAACAGCCTGAAACCTGAGGACACGGCCGTCTATTACTGTAATTCA-- | ----GCT-------GAATACTGGGGCCAGGGGACCCAGGTCACCGTCTCCCAGCGGCCGCTACCCGTACGAC | GTTCCGGACTACGGTTCCGGCCCGAGCATAG |

FIG. 16B

| SEQ ID NO: | |
|---|---|
| 190: | CAGGTGCAGCTGCAGCTGCAGGAGTCTGGGGAGGCTCGGTGCAGCCTCGGTGGGGGTCTCTGAGCCTCTCCTGTTCAGCCTC |
| 189: | CAGGTGCAGCTGCAGCTGCAGGAGTCTGGGGAGGCTCGGTGCAGCCTCGGTGGGGGTCTCTGAGCCTCTCCTGTTCAGCCTC |
| 191: | CAGGTGCAGCTGCAGCTGCAGGAGTCTGGGGAGGCTCGGTGCAGCCTTGGTGCAGCCTCGGTGGGGGTCTCTGAGCCTCTCCTGTTCAGCCTC |
| 193: | CAGGTGCAGCTGCAGCTGCAGGAGTCTGGGGAGGCTTGGTGCAGCCTTGGTGGGGGTCTCTGAGACTCTCCTGTTCAGCCTC |
| 192: | CAGGTGCAGCTGCAGCTGCAGGAGTCTGGGGAGGCTTGGTGCAGCCTTGGTGGGGGTCTCTGAGCCTCTCCTGTTCAGCCTC |
| | |
| 190: | TGGAATCATCTTCAGTGACTATGCCCTGACCTGGTACCGCCAGGCTCCAGGGAAGCAGCGCGAGTGGGTTGCAC |
| 189: | TGGAATCATCTTCAGTGACTATGCCCTGACCTGGTACCGCCAGGCTCCAGGGAAGCAGCGCGAGTGGGTTGCAC |
| 191: | TGGAATCATCTTCAGTGACTATGCCCTGACCTGGTACCGCCAGGCTCCAGGGAAGCAGCGCGAGTGGGTTGCAC |
| 193: | TGGAATCATCTTCAGTGACTATGCCCTGACCTGGTACCGCCAGGCTCCAGGGAAGCAGCAGCGCGAGTGGGTTGCAC |
| 192: | TGGAATCATCTTCAGTGACTATGCCCTGACCTGGTACCGCCAGGCTCCAGGGAAGCAGCAGCGCGAGTGGGTTGCAC |
| | |
| 190: | AGATTACGCG---AAGCCAAAATATAAATTATACAGGATCCGTGAAGGGCCGATTCACCGTCTCCAGAGACAAC |
| 189: | AGATTACGCG---AAGTCAAAATATAAATTATACAGGATCCGTGAAGGGCCGATTCACCGTCTCCAGAGACAAC |
| 191: | AGATTACGCG---AAGCCAAAATATAAATTATACAGGATCCGTGAAGGGCCGATTCACCGTCTCCAGAGACAAC |
| 193: | AGATTACGCG---AAGTCAAAATATAAATTATACAGGATCCGTGAAGGGCCGATTCACCGTCTCCAGAGACAAC |
| 192: | AGATTACGCG---AAGGCAAAATATAAATTATACAGGATCCGTGAAGGGCCGATTCACCGTCTCCAGAGACAAC |

FIG. 16C

| SEQ ID NO | |
|---|---|
| 190 : | GCCAAGAACACAGTGCATCTGCAAATGAACAGCCTGAAACCTGAGGACACGGCCGTCTACTATTGTCATGCATA |
| 189 : | GCCAAGAACACAGTGCATCTGCAAATGAACAGCCTGAAACCTGAGGACACGGCCGTCTACTATTGTCATGCATA |
| 191 : | GCCAAGAACACAGTGCATCTGCAAATGAACAGCCTGAAACCTGAGGACACGGCCGTCTACTATTGTCATGCATA |
| 193 : | GCCAAGAACACAGTGCATCTGCAAATGAACAGCCTGAAACCTGAGGACGCGGCCGTCTACTATTGTCATGCATA |
| 192 : | GCCAAGAACACAGTGCATCTGCAAATGAACAGCCTGAAACCTGAGGACACGGCCGTCTACTATTGTCATGCATA |
| 190 : | TGACGGTCGACGCC-GAACCTACTGGGGCCAGGGGACCCAGGTCACCGTCTCCAGCGGCCGCTACCCGTACGAC |
| 189 : | TGACGGTCGACGCC-CACCCTACTGGGGCCAGGGGACCCAGGTCACCGTCTCCAGCGGCCGCTACCCGTACGAC |
| 191 : | TGACGGTCGACGCC-CACCCTACTGGGGCCAGGGGACCCAGGTCACCGTCTCCAGCGGCCGCTACCCGTACGAC |
| 193 : | TGACGGTCGACGCC-CACCCTACTGGGGCCAGGGGACCCAGGTCTCCAGCGGCCGCTACCCGTACGAC |
| 192 : | TGACGGTCGACGAT-CACCCTACTGGGGCCAGGGGACCCAGGTCACCGTCTCCAGCGGCCGCTACCCGTACGAC |
| 190 : | GTTCCGGACTACGGTTCCGGCCGAGCATAG |
| 189 : | GTTCCGGACTACGGTTCCGGCCGAGCATAG |
| 191 : | GTTCCGGACTACGGTTCCGGCCGAGCATAG |
| 193 : | GTTCCGGACTACGGTTCCGGCCGAGCATAG |
| 192 : | GTTCCGGACTACGGTTCCGGCCGAGCATAG |

FIG. 16D

| SEQ ID NO | | 
|---|---|
| 200: | CAGGTGCAGCTGCAGGAGAGTCTGGGGGAGGCTTGGTGCAACCTGGGGGTTCTCTGAGACTCTCCTGTGCAGCCTC |
| 201: | CAGGTGCAGCTGCAGGAGAGTCTGGGGGAGGCTTGGTGCAACCTGGGGGTTCTCTGAGACTCTCCTGTGCAGCCTC |
| 197: | CAGGTGCAGCTGCAGGAGAGTCTGGGGGAGGCTTGGTGCAATCTGGGGATTCTCTGAGACTCTCCTGTGCAGCCTC |
| 198: | CAGGTGCAGCTGCAGGAGAGTCTGGGGGAGGCTTGGTGCAACCTGGGGGTTCTCTGAGACTCTCCTGTGCAGCCTC |
| 200: | TGGATTCACCTTCAGTAGCTATGCTATGAGCTGGGTCCGCCTGGCTCCAGGAAAGGGGCTCGAGTGGGTCTCAA |
| 201: | TGGATTCACCTTCAGTAGCTATGCTATGAGCTATGAGCTGGGTCCGCCAGGCTCCAGGAAAGGGGCTCGAGTGGGTCTCAA |
| 197: | TGGATTCACCTTCAGTAACTATGCTATGAGCTGGGTCCGCCAGGCTCCAGGAAAGGGGCTCGAGTGGGTCTCAA |
| 198: | TGGATTCACCTTCAGTAACTATGCTATGAGCTGGGTCCGCCAGGCTCCAGGAAAGGGGCTCGAGTGGGTCTCAA |
| 200: | CTATTAATATCGCTGGTGGTATCACAAGCTATGCAGACTCCGTGAAGGGCCGATTCACCATCTCCAGAGACAAC |
| 201: | CTATTAATATGGGTGGTGGTACCACAAGCTATGCAGACTCCGTGAAGGGCCGATTCACCATCTCCAGACACAAC |
| 197: | CTATTAATAGTGGTGGTAGCACAAGCTATGCGACTCCGTGAAGGGCCGATTCACCATCTCCAGAGACAAC |
| 198: | CTATTAATATTGGTGGTAGCACAAGCTATGCAGACTCCGTGAAGGGCCGATTCACCATCTCCAGAGACAAC |

FIG. 16E

| SEQ ID NO | |
|---|---|
| 200: | GCCAAGAACACGCTGTATCTGCAAATGAACAGCCTGAAACCTGAGGACACGGCCGTGTATTACTGTG-CAAAAA |
| 201: | GCCAAGAACACGCTGTATCTGCAAATGAACAGCCTGAAACCTGAGGACACGGCCGTGTATTACTGTG-CAAAAA |
| 197: | GCCAAGAACACGCTGTATCTGCAAATGAACAGCCTGAAACCTGAGGACACGGCCGTGTATTACTGTG-CAAAGA |
| 198: | GCCAAGAACACGCTGTATCTGCAAATGAACAGCCTGAAACCTGAGGACACGGCCGTGTATTACTGTG-CAAAGA |
| | |
| 200: | CGGCGGCCCAACTGGAGCGCCCAGAGAGGCCCAGGTGACCCAGGTCACCGTCTCCAGCGCCGCTACCCGTACGAC |
| 201: | CGGCGGGCCAACTGGAGCGCCCAGAGAGAGGCCAGGGGACCCAGGTCACCGTCTCCAGCGCCGCTACCCGTACGAC |
| 197: | CGGCCTCTCAC----ATACCCTTGA--GCCAGGGGACCCAGGTCACCGTCTCCAGCGCCGCTACCCGTACGAC |
| 198: | CGGCCTCTCAC----ATACCCTTGA--GCCAGGGGACCCAGGTCACCGTCTCCAGCGCCGCTACCCGTACGAC |
| | |
| 200: | GTTCCGGACTACGGTTCCGGCCGAGCATAG |
| 201: | GTTCCGGACTACGGTTCCGGCCGAGCATAG |
| 197: | GTTCCGGACTACGGTTCCGGCCGAGCATAG |
| 198: | GTTCCGGACTACGGTTCCGGCCGAGCATAG |

FIG. 16F

```
SEQ
ID NO
199:  CAGGTGCAGCTGCAGGAGTCTGGGGGAGGCTTGGTGCAACCTGGGGGGTTCTCTGAGACTCTCCTGTGCAGCCTC
202:  CAGGTGCAGCTGCAGGAGTCTGGGGGAGGCTTGGTGCAACCTGGGGGGTTCTCTGAGACTGTCCTGTGCAGCCTC
203:  CAGGTGCAGCTGCAGGAGTCTGGGGGAGGCCTGGTGCAACCTGGGGGGTTCTCTGAGACTGTCCTGTGCAGCCTC
196:  CAGGTGCAGCTGCAGGAGTCTGGGGGAGGCTTGGTGCGGCCTGGGGATCTCTAAGACTCTCCTGTGAAGCCTC

199:  TGGATTCACCTTCAGGAACTATGCAATGAGCTGGGTCCGTCAGGCTCCAGGAAAGGGGCTCGAGTGGGTCTCAA
202:  TGGATTCACCTTCAGTACAAGTACAAGTGCCATGAGTTGGATCCGCCAGCCTCCAGGGAAGGCGCGAGGTGGTCGCAA
203:  TGGATTCACCTTCAGTACAAATGCCATGAGTTGGATCCGCCAGCCTCCAGGAAGCCTCGAGGTGGTCGCAA
196:  TGGAACCACCTTCAGAGCCTCGTAATGAAATGGTACCGCCAGGCTCCAGGGAAGGAGCGCGAGTGGTCGCAT

199:  CTATTAATGGTGGTGGTGTATCACAAGCTATGCAGACTCCGTGAAGGGCCGATTCACCATCTCCAGAGACAAC
202:  CTATTACTAGTGCTGGTGGTAGTATAAGTTATGTAAACTCCGTGAAGGGCCGATTCACCATCTCCAGAGACAAC
203:  CTATTACTAGTGCTGGTGGTAGTATAAGTTATGTAAACTCCGTGAAGGGCCGATTCACCATCTCCAGAGACAAC
196:  TTATTTCTAGTCCTGGTGATCGCACTCGCTACACAGAAGCCGTGAAGGGCCGATTCACCATCTCCAGAGACAAT
```

FIG. 16G

| SEQ ID NO | |
|---|---|
| 199: | GCCAAGAACACAATGTATCTGCAAATGAACAGCCTGAAACCTGAGGACACGGCCGTCTATTACTGTG-CCCAAA |
| 202: | GCCAAGAACACGCTGTATCTGCAAATGAACATGCTGAAACCTGAGGACACGGCCGTGTATTACTGTG-CCCGAC |
| 203: | GCCAAGAACACGCTGTATCTGCAAATGAACATGCTGAAACCTGAGGACACGGCCGTGTATTACTGTG-CCCGAC |
| 196: | GCCAAGAACGCGCTGTATCTGCAAATGAACGGCCTGAAACCTGAGGACACGGCCGTGTATTATTGTAACGCGAA |
| 199: | CCGCCCGCGATTCCCGCGATTCCCGGGGCCAGGGGACCCAGGTCACCGTCTCCAGCGGCCGCTACCCGTACGAC |
| 202: | TGGTCAACCTT-----GCCCAGACCGGCCAGGGAACCCAGGTCACCGTCTCCAGCGGCCGCTACCCGTACGAC |
| 203: | TGGTCAACCTT-----GCCCAGACCGGCCAGGGACCCAGGTCACCGTCTCCAGCGGCCGCTACCCGTACGAC |
| 196: | CGGAATATACT-------GGGGCAAAGGGACCCAGGTCACCGTCTCCAGCGGCCGCTACCCGTACGAC |
| 199: | GTTCCGGACTACGGTTCCGGCCGAGCATAG |
| 202: | GTTCCGGACTACGGTTCCGGCCGAGCATAG |
| 203: | GTTCCGGACTACGGTTCCGGCCGAGCATAG |
| 196: | GTTCCGGACTACGGTTCCGGCCGAGCATAG |

FIG. 16H

| SEQ ID NO | | | |
|---|---|---|---|
| 218: | CAGGTGCAGCTGCAGGAGTCTGGGGGAGGCATGGTAGAACCTGGGGGTTCTCTGAGACTCTCCTGTGCAGCCTC | TGGATTCCGCTTCAGTAGTTATGCTATGAGTTGGGTCCGCCAGGCTCCAGGGAAAGGGGCTCGAGCGGGTCTCGG | CTATTAATAGTGATGGTGATAAAACAAGCTATGCAGACTCCGTGAAGGGCCGATTTACCATCTCCAGAGACAAC |
| 219: | CAGGTGCAGCTGCAGGAGTCTGGAGGAGGCTTGGTAGAACCTGGGGGTTCTCTGAGACTCTCCTGTGCAGCCTC | TGGATTCCGCTTCAGTAGTTATGCTATGAGTTGGGTCCGCCAGGCTCCAGGAAAGGGGCTCGAGCGGGTCTCAG | CTATTAATAGTGATGGTGATAAAACAAGCTATGCAGACTCCGTGAAGGGCCGATTTACCATCTCCAGAGACAAC |
| 220: | CAGGTGCAGCTGCAGGAGTCTGGGGGAGGCATGGTAGAACCTGGGGGTTCTCTGAGACTCTGTGCAGCCTC | TGGATTCCGCTTCAGTAGTAGTTATGCTATGAGTTGGGTCCGCCAGGCTCCAGGCTCCAGGAAAGGGGCTCGAGCGGGTCTCGG | CTATTAATAGTGATGGTGATAAAACAAGCTATGCAGACTCCGTGAAGGGCCGATTCACCATCTCCAGAGACAAC |
| 221: | CAGGTGCAGCTGCAGGAGTCTGGGGGAGGCTTGGTGCAGCCTGGTCTCTGAGTCTCTCAGACTCTCCTGTGCAGCCTC | TGGACTCCGCTTCAGTAGTAGTTATGCTATGAGTTGGGTCCGCCAGGCTCCAGGAAGGAAAGGGGCTCGAGCGGGTCTCGG | CTATTAATAGTGATGGTGATAAAACAAGCTATGCAGACTCCGTGAAGGGCCGATTCACCATCTCCAGAGACAAC |
| 225: | CAGGTGCAGCTGCAGGAGTCTGGGGGAGGCTCGGTGCAGCCTGGGGGGTCTCTGAAACTCTCCTGTGCAGCCTC | TGGATTCACCCTCAATTGGTATACCATGGCCTGGTATCGCCAGGTTCCAGGGAGGAGCGCAAAATGTGCCA | CAATTACAGGTGCTAGTGGTGACACAAAATATGCAGACTCCACCAATCTCCAGAGACAAT |

FIG. 17A

| SEQ ID NO | | |
|---|---|---|
| 218: | GCCAGGAACACGCTGTATCTGCAAATGAGCAACCTGAAGACACGGCCGTGTATTACTGTGCAGACCG |
| 219: | GCCAGGAACACGCTGTATCTGCAAATGAGCAACCTGAAGACACGGCCGTGTATTACTGTGCAGACCG |
| 220: | GCCAGGAACACGCTGTATCTGCAAATGAACAACCTGAAGACACGGCCGTGTATTACTGTGCAGACCG |
| 221: | GCCAGGAACACGCTGTATCTGCAAATGAGCAACCTGAAGACACGGCCGTGTATTACTGTGCAGACCG |
| 225: | GCCAAGAACACGGTGACACTGCAAATGAACAGCCTTAAACCTGGAGACACGGCCGTCTATTACTGTCATGCC-- |

| 218: | AGATTTGTACTGTGTTCAGGCTCTCTATGTGTA-AGGACGTCTTGG-GGGGAGCACGCTATGACTT-TCGGGGCCAGG |
|---|---|
| 219: | AGATTTGTACTGTGTTCAGGCTCTCTATGTGTA-AGGACGTCTTGG-GGGGAGCACGCTATGACTT-TCGGGGCCAGG |
| 220: | AGATTTGTACTGTGTTCGGGCTCTCTATGTGTA-AGGACGTCTTGG-GGGGAGCACGCTATGACTT-TCGGGGCCAGG |
| 221: | AGATTTGTACTGTGTTCAGGCTCTCTATGTGTA-AGGACGTCTTGG-GGGGAGCACGCTATGACTT-TCGGGGCCAGG |
| 225: | -----TGCC---TAAC---CTACGACT---CGGGGTCCGT----CAAAG--GAGT-TAACTA-CTGGGTCAGG |

| 218: | GGACCCAGGTCACCGTCACCGTCTCCAGCGGCCGCTACCCGTACGACGTTCCGGCCGAGCATAG |
|---|---|
| 219: | GGACCCAGGTCACCGTCACCGTCTCCAGCGGCCGCTACCCGTACGACGTTCCGGCCGAGCATAG |
| 220: | GGACCCAGGTCACCGTCACCGTCTCCAGCGGCCGCTACCCGTACGACGTTCCGGCCGAGCATAG |
| 221: | GGACCCAGGTCACCGTCACCGTCTCCAGCGGCCGCTACCCGTACGACGTTCCGGCCGAGCATAG |
| 225: | GGACCCAGGTCACCGTCACCGTCTCCAGCGGCCGCTACCCGTACGACGTTCCGGCCGAGCATAG |

FIG. 17B

| SEQ ID NO: | |
|---|---|
| 224: | CAGGTGCAGCTGCAGGAGAGTCTGGGGGAGGCTCGGTGCAGCCTGGGGGGTCTCTGAAACTCTCCTGTGCAGCCTC |
| 223: | CAGGTGCAGCTGCAGGAGAGTCTGGGGGAGGCTTGGTGCGGCCTGGGGGGTCTCTGAAACTCTCCTGTGCAGCCTC |
| 226: | CAGGTGCAGCTGCAGGAGAGTCTGGGGGAGGCTTGGTGCAGCCTGGGGGGTCTCTGAAACTCTCCTGTGCAGCCTC |
| 222: | CAGGTGCAGCTGCAGGAGAGTCTGGAGGAGGCCTGGTGCAGCCTGGGGGGTCTCTGAAACTCTCCTGTGCAGCCTC |
| 227: | CAGGTGCAGCTGCAGGAGAGTCTGGGGGAGGCCTGGTGCAGCCTGGGGGGTCTCTGAAACTCTCCTGTGCAGCCTC |
| 224: | TGGATTCACCTTCAATTGGTATACCATGGCCTGGTATCGCCAGGTTCCAGGGGAGGAGCGCAAAATGGTTGCCA |
| 223: | TGGATTCACCTTCAATTGGTATACCATGGCCTGGTATCGCCAGGTTCCAGGGGAGGAGCGCAAAATGGTCGCCA |
| 226: | TGGATTCACCTTCAATTGGTATACCATGGCCTGGTATCGCCAGGTTCCAGGGGAGGAGCGCAAAATGGTCGCCA |
| 222: | TGGATTCACCTTCAATTGGTATACCATGGCCTGGTATCGCCAGGTTCCAGGGGAGGAGCGCAAAATGGTCGCCA |
| 227: | TGGATTCACCTTCAATTGGTATACCATGGCCTGGTATCGCCAGGTTCCAGGGGAGGAGCGCAAAATGGTCGCCA |
| 224: | CAATTACAGGTGCTAGTGGTGACACAAAATATGCAGATCTCCGTGAAGGGCCGGTTCACCATCTCCAGAGACAAT |
| 223: | CAATTACAGGTGCTAGTGGTGACACAAAATATGCAGATCTCCGTGAAGGGCCGGTTCACCATCTCCAGAGACAAT |
| 226: | CAATTACAGGTGCTAGTGGTGACACAAAATATGCAGATCTCCGTGAAGGGCCGGTTCACCATCTCCAGAGACAAT |
| 222: | CAATTACAGGTGCTAGTGGTGACACAAAATATGCAGATCTCCGTGAAGGGCCGGTTCACCATCTCCAGAGACAAT |
| 227: | CAATTACAGGTGCTAGTGGTGACACAAAATATGCAGATCTCCGTGAAGGGCCGGTTCACCATCTCCAGAGACAAT |

FIG. 17C

| SEQ ID NO | |
|---|---|
| 224: | GCCAAGAACACGGTGACACTGCAAATGAACAGCCTTAAACCTGGAGACACGGCCGTCTATTACTGTCATGCC-- |
| 223: | GCCAAGAACACGGTGACACTGCAAATGAACAGCCTTAAACCTGGAGACACGGCCGTCTATTACTGTCATGCC-- |
| 226: | GCCAAGAACACGGTGACACTGCAAATGAACAGCCTTAAACCTGGAGACACGGCCGTCTATTACTGTCATGCC-- |
| 222: | GCCAAGAACACGGTGACACTGCAAATGAACAGCCTTAAACCTGGAGACACGGCCGTCTATTACTGTCATGCC-- |
| 227: | GCCAAGAACACGGTGACACTGCAAATGAACAGCCTTAAACCTGGAGACACGGCCGTCTATTACTGTCATGCC-- |

| 224: | -----TACC---TAAC----CTACGACT--CGGGGTCCGT----CAAAG--GAGT-TAACTA-CTGGGCCAGG |
| 223: | -----TACC---TAAC----CTACGACT--CGGGGTCCGT----CAAAG--GAGT-TAACTA-CTGGGCCAGG |
| 226: | -----TACC---TAAC----CTACGACT--CGGGGTCCGT----CAAAG--GAGT-TAACTA-CTGGGCCAGG |
| 222: | -----TACC---TAAC----CTACGACT--CGGGGTCCGT----CAAAG--GAGT-TAACTA-CTGGGCCAGG |
| 227: | -----TACC---TAAC----CTACGACT--CGGGGTCCGC----CAAAG--GAGT-TAACTA-CTGGGCCAGG |

| 224: | GGACCCAGGTCACCGTCTCCAGCGGCCGCTACCCGTACGACGTTCCGGACTACGGTTCCGGCCGAGCATAG |
| 223: | GGACCCAGGTCACCGTCTCCAGCGGCCGCTACCCGTACGACGTTCCGGACTACGGTTCCGGCCGAGCATAG |
| 226: | GGACCCAGGTCACCGTCTCCAGCGGCCGCTACCCGTACGACGTTCCGGACTACGGTTCCGGCCGAGCATAG |
| 222: | GGACCCAGGTCACCGTCTCCAGCGGCCGCTACCCGTACGACGTTCCGGACTACGGTTCCGGCCGAGCATAG |
| 227: | GGACCCAGGTCACCGTCTCCAGCGGCCGCTACCCGTACGACGTTCCGGACTACGGTTCCGGCCGAGCATAG |

FIG. 17D

```
SEQ
ID NO
227:  CAGGTGCAGCTGCAGGAGTCTGGGGGAGGCTTGGTGCAGCCTGGGGGGTCTCTAGGACTCTCCTGTGCAGCCTC
229:  CAGGTGCAGCTGCAGGAGTCTGGGGGAGGCTTGGTGCAGCCTGGGGGGTCTCTGAGACTCTCCTGTGCAGCCTC
230:  CAGGTGCAGCTGCAGGAGTCTGGGGGAGGCTTGGTGCAGCCTGGGGGGTCTACGAGACTCTCCTGTGCAGCCTC
231:  CAGGTGCAGCTGCAGGAGTCTGGGGGAGGCTTGGTGCAGCCTGGGGGGTCTCTGATACTCTCCTGTACAATCTC

227:  TGGAAGCCTCTTAAATATCTATGCCATGGCTCGGTACCGCCAGGCTCCAGGGAGACAGCGCGAGTTGGTCGCAA
229:  TGGAGGCACTTTGGGTTACTATGCCATAGGCTGGTTCCGCCAGGCCCAGGGAAGGAGCGCGAGGCGGTCTCCT
230:  TGGATTCACTTTGGATATATTTATGCTATAGGCTGGTTCCGCCAGGCCCAGGGAAGGAGCATGAGGGGGTCTCGT
231:  GGGAGCCTCGCTCCGAGACCGACGCGTCACCTGGAGTCGCCAAGGTCCAGGGAAATCGCTTGAGATCATCGCAG

227:  CTGTAACGAGT---AGTGGAACCGCAGAATATGCAGACTCCGTGAAGGGCCGATTCACCATCTCTAGAGACAAC
229:  GTATTACTAGTAGTGACACTAGCGCATACTATGCAGACTCCGCGAAGGGCCGATTCACCATCTCCAGAGACAAC
230:  GGATTGTTGGTAATGATGGTAGGACATACTACATAGACTCCGTGAAGGGCCGATTCACCATCTCCAGAGACAAC
231:  TTATGGCGCCG---GATTACGGGGTCCATTACTTTGGCTCCCTGGAGGGCGAGTTGCCGTCCGAGGAGACGTC
```

FIG. 17E

```
SEQ
ID NO
  227:  GCCAAGAACACGGTGTATCTGCAAATGAACAGCCTGAGACCTGAGGACACGGGCGTCTATTACTGTAATGCA------
  229:  GCCAAGAACACGATGTATCTGCAAATGAACAACCTGAAACCTGAGGACACAGCCGTCGTTTATTACTGTGCAGCCGG
  230:  GCCAAGAACACGGTGTATCTTGAAATGAACAGCCTGAGGATACAGCCGTTTATTACTGCGCAGCTAA----------
  231:  GTCAAGAATACAGTATATCTCCAAGTAAACGCCCTGAAACCTGAAACACAGCCATCTATTGGTGCAG-----------

227:  ------CATC---TCAG---ATATGGCGA-CTATGTCCGTGGCCCTCCG--GAGTATAACTA-CTGGGCCAGG
  229:  ---TTACTATT---TTAGAGACTATAGTGA-CAGTTACTACACGGGGACGGGTATGAAAGTCTGGGGCAAAG
  230:  ------GTTCTGGCCCCGATATTATAGTGGTAGGCCTCCAGTAGGGAGGGATGGCTATGACTA-TTGGGGCCAGG
  231:  ----------------TATGGGG------------------AATATCCGGGGCCTGG

227:  GGACCCAGGTCACCGTCTCCAGCGGCCGCTACCCGCTACGACGTTCCGGCCGAGCATAG
  229:  GGACCCAGGTCACCGTCTCCAGCGGCCGCTACCCGCTACGACGTTCCGGCCGAGCATAG
  230:  GGACCCAGGTCACCGTCTCCAGCGGCCGCTACCCGCTACGACGTTCCGGCCGAGCATAG
  231:  GGACCCAGGTCACCGTCTCCAGCGGCCGCTACCCGCTACGACGTTCCGGCCGAGCATAG
```

CAMELIDAE SINGLE-DOMAIN ANTIBODIES AGAINST *YERSINIA PESTIS* AND METHODS OF USE

CROSS-REFERENCE TO RELATED APPLICATIONS

This application is a continuation of U.S. application Ser. No. 13/906,386, filed May 31, 2013 (now abandoned), which claims the benefit of and priority to U.S. Provisional Application No. 61/653,488, filed on May 31, 2012. The disclosure of each application is incorporated herein by reference, in its entirety.

RIGHTS OF THE GOVERNMENT

The invention described herein may be manufactured and used by or for the Government of the United States for all governmental purposes without the payment of any royalty.

Field of the Invention

This invention relates generally to the field of single-domain antibodies. More particularly, it relates to single-domain antibodies and polypeptides against *Yersinia pestis*, nucleic acid sequences encoding the single-domain antibodies, and methods of using the same.

BACKGROUND OF THE INVENTION

Description of the Related Art

Increasing threats of bioterrorism have led to the development of new diagnostic and therapeutic tools for pathogens that can potentially be used as biological weapons. Many of these pathogens, such as the causative agents of plague, anthrax, and tularemia, are relatively easy to manipulate via genetic engineering and may be designed to evade detection by sensor devices. Many of these biological weapons candidates also display resistance to current medical treatments. To be useful, a diagnostic tool must be sensitive and specific, as well as able to withstand the extreme conditions often encountered in the field. The value of a therapeutic tool is largely determined by parameters such as toxicity, immunogenicity, and efficacy after administration. In addition, the therapeutic tool may be required to treat large number of people in the event of a bioterrorism attack. All of these requirements highlight the importance of a long shelf life and the production costs of biological weapon-related diagnostics and therapeutics.

Members of the family Camelidae, which includes alpacas, camels, and llamas, produce conventional antibodies, as well as antibodies consisting only of a dimer of heavy-chain polypeptides. The N-terminal domain of these heavy chain-only antibodies, which is referred to as VHH, is variable in sequence, and it is the sole domain that interacts with the cognate antigen. Because of their small size (12-15 kDa, 2.2 nm diameter, and 4 nm height), VHHs are also known as single-domain antibodies (SAbs), which are commercially-available as NANOBODIES (NANOBODY and NANOBODIES are registered trademarks of Ablynx N.V., Belgium).

SAbs make attractive as tools for biological weapon detection due to their high affinity and specificity for their respective targets and their high stability and solubility. Their small size gives SAbs the unique ability to recognize and bind to areas of an antigen that are often not normally accessible to full-size antibodies due to steric hindrance and other size constraints. In addition, SAbs may be economically produced in large quantities, and their sequences are relatively easy to tailor to a specific application. These properties, as well as their low immunogenicity, make SAbs uniquely suited for detection, diagnostics, and immunotherapeutics.

SUMMARY OF THE INVENTION

The present invention includes a composition comprising at least one single-domain antibody against one or more *Yersinia pestis* (*Y. pestis*) surface proteins, in which the one or more *Y. pestis* surface proteins are selected from the group consisting of YscF, F1, and LcrV, with each single-domain antibody comprising four framing regions (FRs) and three complementarity determining regions (CDRs), in which the at least one single-domain antibody is selected from the group consisting of: (1) at least one single-domain antibody comprising one CDR1 sequence selected from the group consisting of SEQ ID NOs:1-7, one CDR2 sequence selected from the group consisting of SEQ ID NOs:27-33, and one CDR3 sequence selected from the group consisting of SEQ ID NOs:54-60; (2) at least one single-domain antibody comprising one CDR1 sequence selected from the group consisting of SEQ ID NOs:8-19, one CDR2 sequence selected from the group consisting of SEQ ID NOs:34-47, and one CDR3 sequence selected from the group consisting of SEQ ID NOs:61-71, AEY, and PGY; and (3) at least one single-domain antibody comprising one CDR1 sequence selected from the group consisting of SEQ ID NOs:20-26, one CDR2 sequence selected from the group consisting of SEQ ID NOs:48-53, and one CDR3 sequence selected from the group consisting of SEQ ID NOs:72-78 and GNI, with the four framing regions of each single-domain antibody comprising one FR1 sequence selected from the group consisting of SEQ ID NOs:79-102, one FR2 sequence selected from the group consisting of SEQ ID NOs:103-120, one FR3 sequence selected from the group consisting of SEQ ID NOs:121-146, and one FR4 sequence selected from the group consisting of SEQ ID NOs:147-153.

In one embodiment, the at least one single-domain antibody is selected from the group consisting of SEQ ID NOs:154-160, 168-185, and 204-217. In a further embodiment, the at least one single-domain antibody further comprises at least one of a protein tag, a protein domain tag, or a chemical tag.

In one embodiment, the composition comprises a plurality of single-domain antibodies against a single *Y. pestis* surface protein. In another embodiment, at least a portion of the plurality of single-domain antibodies is against different epitopes on the single *Y. pestis* surface protein. In another embodiment, the composition comprises a plurality of single-domain antibodies against at least two *Y. pestis* surface proteins.

In an alternative embodiment, the composition comprises a plurality of single-domain antibodies further comprising a polypeptide. In one embodiment, the plurality of single-domain antibodies comprising the polypeptide are against a single *Y. pestis* surface protein. In another embodiment, at least a portion of the plurality of single-domain antibodies comprising the polypeptide are against different epitopes on the single *Y. pestis* surface protein. In another embodiment, the plurality of single-domain antibodies comprising the polypeptide are against at least two *Y. pestis* surface proteins.

In a further embodiment, the polypeptide comprises a fusion protein. In another embodiment, the polypeptide comprises a multivalent protein complex, with the single-domain antibodies being joined together with at least one linker molecule. In a further embodiment, at least one of the plurality of single-domain antibodies comprising the polypeptide further comprises at least one of a protein tag, a protein domain tag, or a chemical tag.

The present invention further includes at least one isolated nucleotide sequence encoding the at least one single-domain antibody, wherein the at least one isolated nucleotide sequence is selected from the group consisting of SEQ ID NOs:164-170, 189-206, and 221-234.

BRIEF DESCRIPTION OF THE DRAWINGS

FIG. 10 is a protein sequence alignment of seven exemplary YscF SAbs according to the present invention.

FIGS. 11A-B are protein sequence alignments of eighteen exemplary F1 SAbs according to the present invention.

FIGS. 12A-B are the protein sequence alignment of fourteen exemplary LcrV SAbs according to the present invention.

FIGS. 15A-C are sequence alignments of nucleic acid sequences encoding the exemplary YscF SAbs according to the present invention.

FIGS. 16A-H are sequence alignments of nucleic acid sequences encoding the exemplary F1 SAbs according to the present invention.

FIGS. 17A-F are sequence alignments of nucleic acid sequences encoding the exemplary LcrV SAbs according to the present invention.

DETAILED DESCRIPTION OF THE INVENTION

Figure 1:
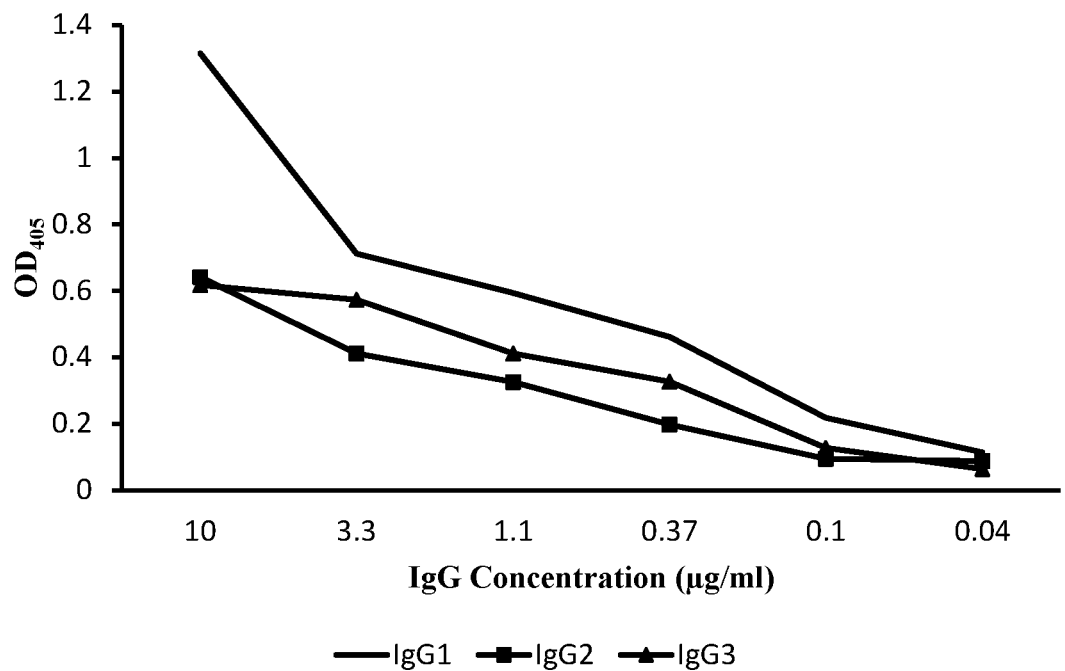
FIG. 1 is a graph of the binding response of IgG isolated from an immune alpaca to *Y. pestis* YscF (ELISA).

The present invention includes single-domain antibodies (SAbs) against three *Yersinia pestis* (*Y. pestis*) surface proteins (LcrV, YscF, and F1), the nucleic acids encoding the SAbs, and polypeptides comprising two or more SAbs capable of recognizing one or more *Y. pestis* surface proteins or epitopes. The present invention further includes methods for preventing or treating *Y. pestis* infections in a patient; methods for detecting and/or diagnosing *Y. pestis* infections; and devices and methods for identifying and/or detecting *Y. pestis* on a surface and/or in an environment.

*Y. pestis*, the gram-negative *bacillus* that causes plague, is considered a Class A biological weapon. *Y. pestis* infections occur in three different ways: infection of the lymph nodes (bubonic), the lungs (pneumonic), or the blood (septicemic). The most serious, contagious, and often fatal mode of plague is pneumonic plague, which may be caused by inhalation of contaminated respiratory droplets from another infected person or from intentional release of aerosolized plague pathogen. While *Y. pestis* infections are treatable with antibiotics, diagnosis and treatment are often delayed. In the case of pneumonic plague, the early symptoms such as fever, headache, and nausea may easily be mistaken for more common illnesses, delaying proper diagnosis and treatment during the early stages of the disease and greatly increasing the chances of death. Untreated pneumonic plague has a mortality rate of almost 100%. In the case of battlefield personnel and persons stationed or living in rural areas, access to proper health care may be further limited by distance and availability.

Of particular interest for detection and treatment are three *Y. pestis* surface proteins, LcrV, YscF, and F1. LcrV is a 37 kDa virulence factor that is secreted and expressed on the *Y. pestis* cell surface prior to bacterial interaction with host cells, making it an excellent antigenic protein for antibody capture. It has been shown that anti-LcrV antibodies can block the delivery of Yops, a set of virulence proteins exported into the host cell upon contact. Additionally, it has been shown that a single sensitive, specific antibody could be used to capture LcrV from *Y. pestis*, *Y. pseudotuberculosis*, and *Y. enterocolitica*. The functional determination of LcrV provides a possible reason for the success of anti-LcrV Ab immunotherapeutics as it is hypothesized that the anti-LcrV/Ab complex prevents the formation and function of the tip complex, thus interfering with the translocation of virulent Yops critical to infection. YscF has also been implicated as one of the "needle" proteins involved in T3SS injection of the virulent Yops proteins across eukaryotic membranes upon cell contact. Recent work using purified YscF to initiate an active immune response indicates that YscF-vaccinated mice have significant protection to a *Y. pestis* challenge. As with LcrV, these data indicate that YscF is an excellent antigen target for immunotherapeutic uses. F1 protein, which is a *Y. pestis* capsule protein, has likewise been identified as a potential therapeutic target and is one of the principal immunogens in currently available plague vaccines. Among other roles, F1 is thought to be involved in preventing *Y. pestis* uptake by macrophages.

SAbs in general, including the presently disclosed *Y. pestis* SAbs, comprise four framework regions (FRs) interrupted by three complementarity determining regions (CDRs) to yield the following general structure:

FR1-CDR1-FR2-CDR2-FR3-CDR3-FR4.

Like many SAbs, the CDR3 sequence of the presently disclosed *Y. pestis* SAbs is generally the most crucial in determining antigen specificity. SAbs directed against a particular antigen generally demonstrate some degree of homology or sequence identity between each FR and CDR. Where two nucleotide or amino acid sequences are the same length when aligned, the term "sequence identity" as used herein relates to the number of positions with identical nucleotides or amino acids divided by the total number of nucleotides or amino acids. The number of identical nucleotides or amino acids is determined by comparing corresponding positions of a designated first sequence (usually a reference sequence) with a second sequence. Where two nucleotide or amino acid sequences are of different length when aligned, the term "sequence identity" as used herein relates to the number of positions with identical nucleotides or amino acids divided by the number of nucleotides or amino acids in the designated or reference sequence. Any addition, deletion, insertion, or substitution of a nucleotide or amino acid is considered a difference when calculating the sequence identity. The degree of sequence identity may also be determined using computer algorithms, such algorithms may include, for example, commercially-available Basic Local Alignment Search Tool, also known as BLAST (U.S. National Library of Medicine, Bethesda, Md.).

*Y. pestis* SAbs according to the present invention may be used as components of in vivo and in vitro assays and may also be used diagnostic testing and imaging. The generally low toxicity and immunogenicity of SAbs further makes the present *Y. pestis* SAbs promising active and passive immunotherapeutic tools, particularly for self-administered fieldable therapeutics. In the case of an outbreak or a biological weapon attack, a self-administered treatment could provide sufficient temporary immunity and sufficiently slow the onset and progress of the disease to allow a person exposed to *Y. pestis* to reach a hospital for diagnosis and treatment. The SAbs may be introduced by any suitable method including intravenous and subcutaneous injection, oral ingestion, inhalation, and topical administration. The SAbs may bind to extracellular epitopes and antigens and may also bind to intracellular targets after introduction into the host cell by phagocytosis or other mechanisms. In addition, the *Y. pestis* SAbs may be useful for decontamination and as field-stable capture elements for real-time biological weapon detection and quantitation.

Many of the presently disclosed *Y. pestis* SAbs demonstrate full functionality and high affinity for their respective antigen targets, which is likely due to the ability of SAbs to bind to protein clefts that are often inaccessible to larger, conventional antibodies. This ability to access areas located in interior pockets may allow therapeutic and detection tools based on the present *Y. pestis* SAbs to detect multiple strains of the pathogen, as well as related organisms in the *Yersinia* genus. SAb-based tools and techniques may also be less susceptible to genetic engineering of pathogen surface proteins and epitopes designed to elude current detectors and to circumvent immunity conferred by conventional vaccination.

The *Y. pestis* SAbs according to the present invention may be quickly, easily, and inexpensively produced in large quantities in a bacterial expression system such as *E. coli* with little or no loss of protein activity and little or no need for post-translational modification. In addition, the SAbs are stable within a wide range of temperature, humidity, and pH. This stability may allow for stockpiling and long-term storage of the SAbs and SAb-based detection, diagnostic, and therapeutic tools in preparation for *Y. pestis* outbreaks and/or a bioterrorism attack, all without the need for costly climate control and/or monitoring. The stability of SAbs in extreme environments may further allow for reusable sensors and detection devices.

The following examples and methods are presented as illustrative of the present invention or methods of carrying out the invention, and are not restrictive or limiting of the scope of the invention in any manner. Amino acid residues will be according to the standard three-letter or one-letter amino acid code as set out in Table 1. The materials and methods used in Examples 1-4 are described, for example, in *Antibody Engineering*, Eds. R. Kontermann & S. Dübel, Springer-Verlag, Berlin Heidelberg (2010) Isolation of antigen-specific Nanobodies, Hassanzadeh Ghassabeh Gh., et al., Vol. 2, Chapter 20, pp. 251-266. Exemplary combinations of individual FR and CDR regions are shown in Table 2, and complete SAb protein sequences isolated according to the following Examples are listed in Tables 3, 5, and 7. Unique sequences (individual CDRs and FRs and complete SAb sequences) are each assigned a SEQ ID NO; sequences comprising less than four amino acids are not assigned a SEQ ID NO. As seen in FIGS. 10-12, some SAbs share 100% sequence identity in one or more CDRs and/or FRs because the SAbs are either from clonally-related B-cells or from the same B-cell with diversification due to PCR error during library construction.

Example 1: Antibody Development and Construction of a VHH Library

Figure 2:
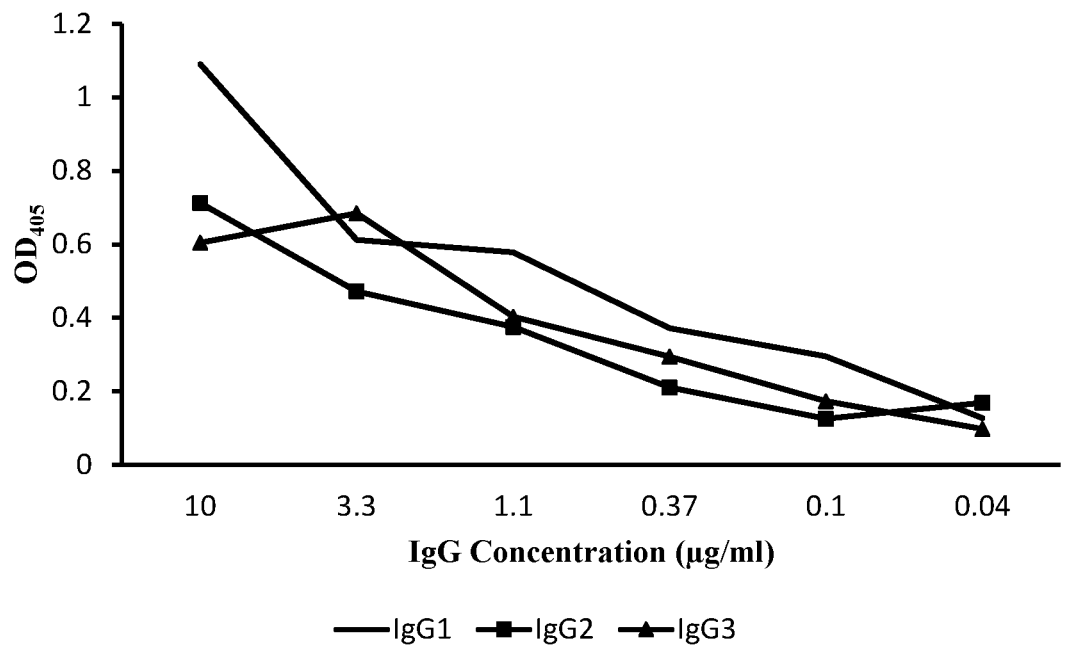
FIG. 2 is a graph of the binding response of IgG isolated from an immune alpaca to *Y. pestis* F1 (ELISA).
Figure 3:
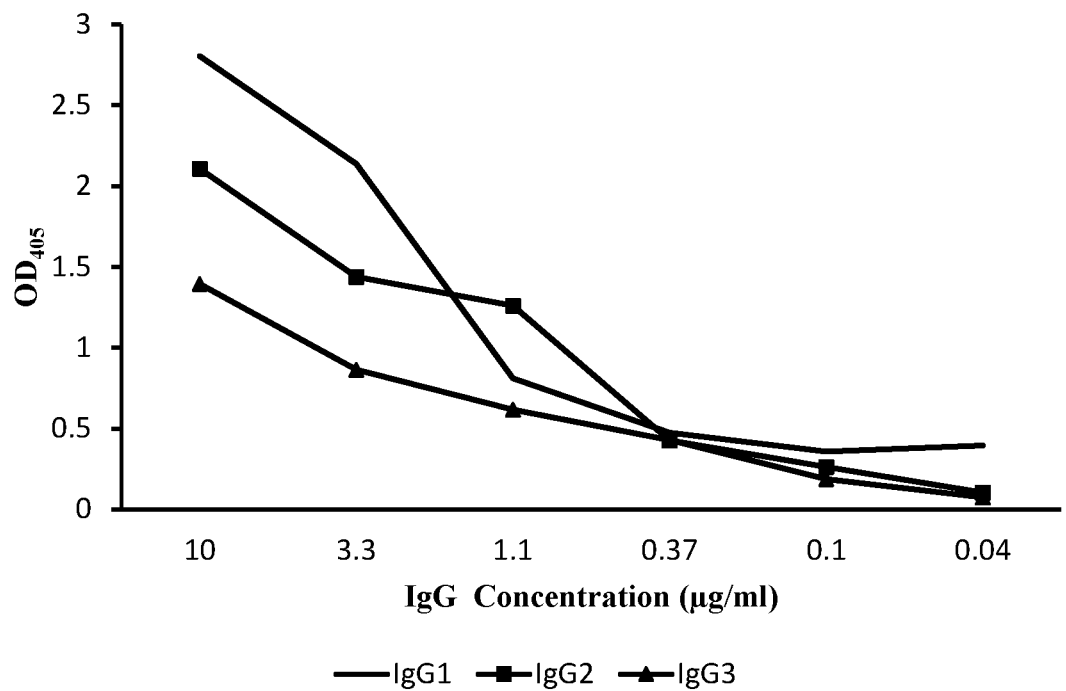
FIG. 3 is a graph of the binding response of IgG isolated from an immune alpaca to *Y. pestis* LcrV (ELISA).

All SAbs were developed using proteins (antigen) expressed from genes isolated from *Y. pestis* KIM5 (avirulent pgm−), which is similar in sequence to the same protein set in *Y. pestis* virulent strains (pgm+). An alpaca was injected subcutaneously on days 0, 7, 14, 21, 28 and 35, each time with about 165 µg YscF antigen, about 160 µg F1 antigen, and about 160 µg LcrV antigen. The same animal may be used for all experiments, but multiple animals may also be used. On day 39, anticoagulated blood was collected from the alpaca for the preparation of plasma and peripheral blood lymphocytes. Using plasma from the immune animal, IgG subclasses were obtained by successive affinity chromatography on protein A and protein G columns and were tested by ELISA to assess the immune response to YscF, F1, and LcrV antigens. FIGS. 1-3 are graphs of the immune response to YscF, F1, and LcrV, respectively, in both conventional (IgG1) and heavy chain (IgG2 & IgG3) antibodies. As seen in FIGS. 1-3, the IgG isolated from the immune animal exhibited a strong response toward all three antigens in both types of antibody.

A VHH library was then constructed and screened for the presence of SAbs specific to YscF, F1, and LcrV. Total RNA was extracted from peripheral blood lymphocytes isolated from the immune alpaca and used as a template for first strand cDNA synthesis with oligo(dT) primer. Using this cDNA, the VHH encoding sequences were amplified by PCR and cloned into the phagemid vector pHEN4. pHEN4 vectors containing the amplified VHH sequences were transformed into electrocompetent cells to obtain a VHH library of about $1-2 \times 10^8$ independent transformants. About 75-93% of transformants harbored vectors with the correct insert sizes. Antigen-specific SAbs were then selected from a phage display library.

Example 2: Isolation of YscF SAbs

Figure 4:
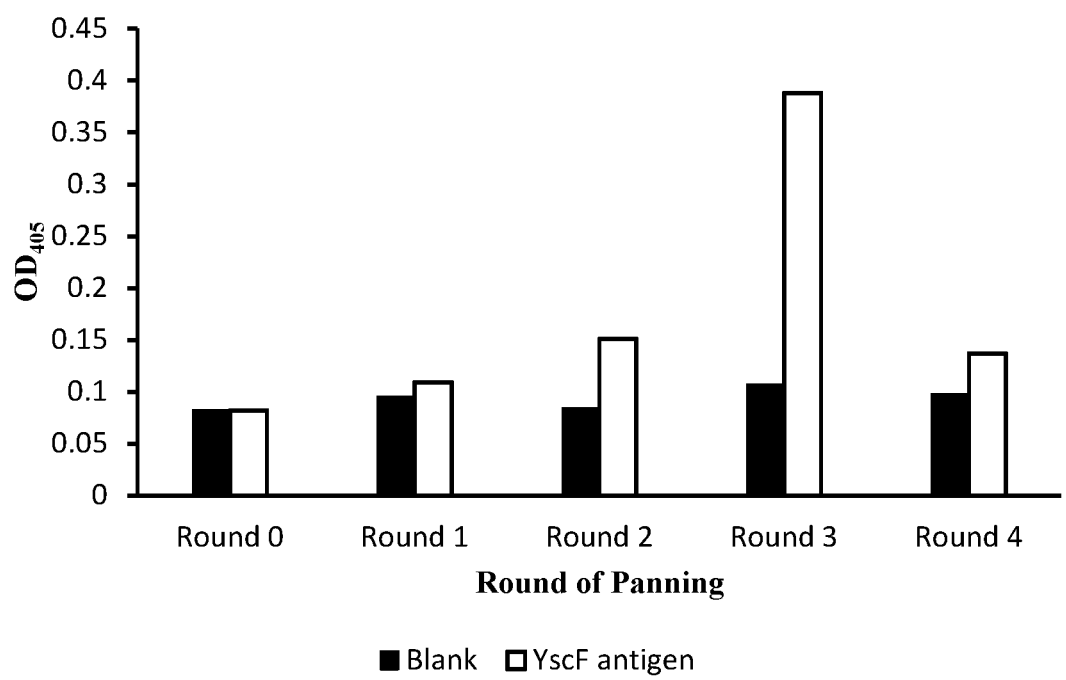
FIG. 4 is a graph of polyclonal phage ELISA testing after each round of panning to isolate YscF-specific phages.
Figure 5:
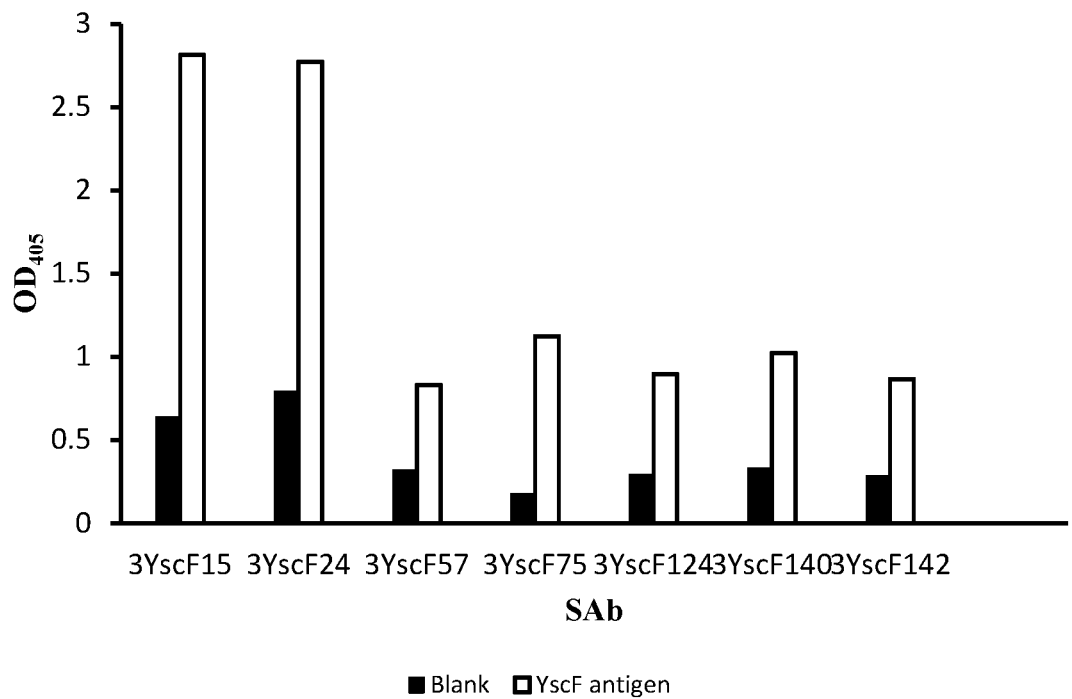
FIG. 5 is a graph of the ELISA for the presence of YscF-specific SAbs in the periplasmic extract of positive colonies.
Figure 6:
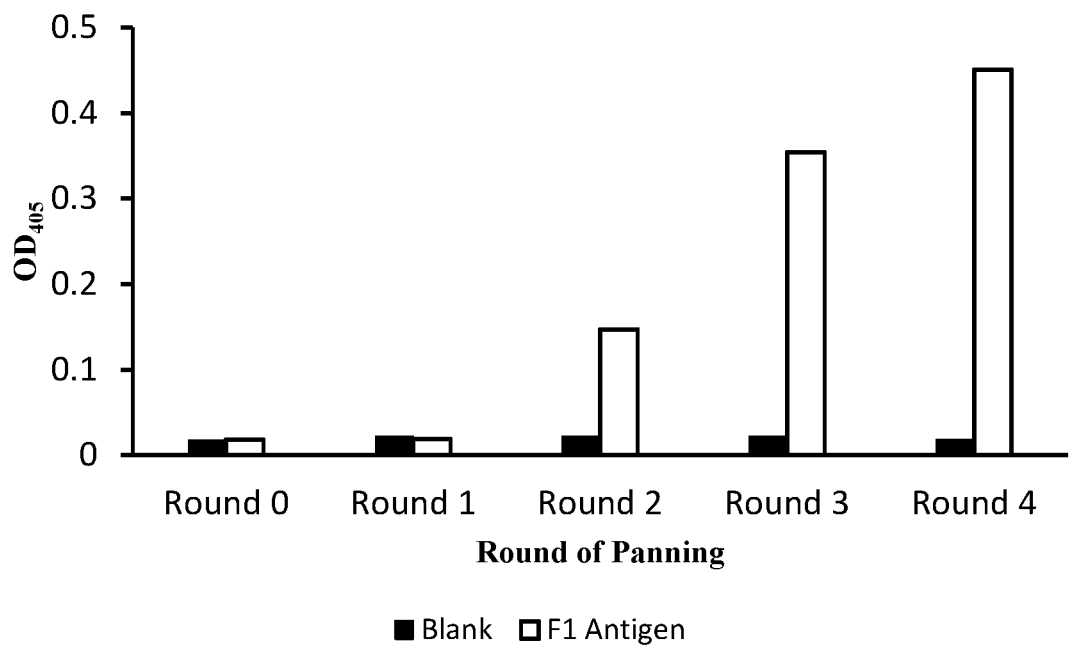
FIG. 6 is a graph of polyclonal phage ELISA testing after each round of panning to isolate F1-specific phages.
Figure 7A:
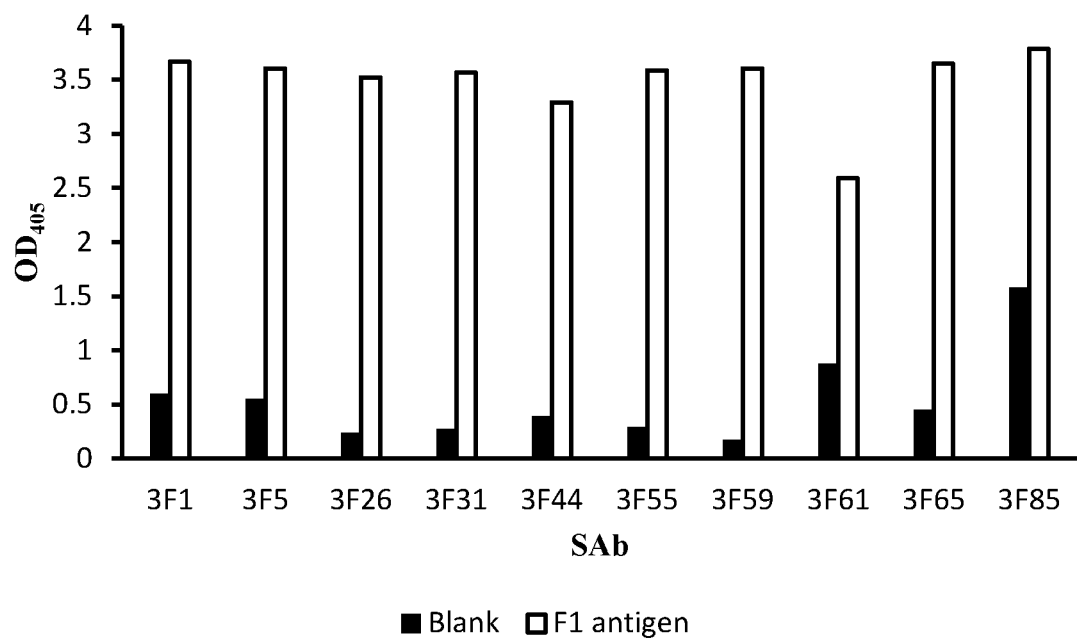
FIGS. 7A-B are graphs of the ELISA for the presence of F1-specific SAbs in the periplasmic extract of positive colonies.
Figure 7B:
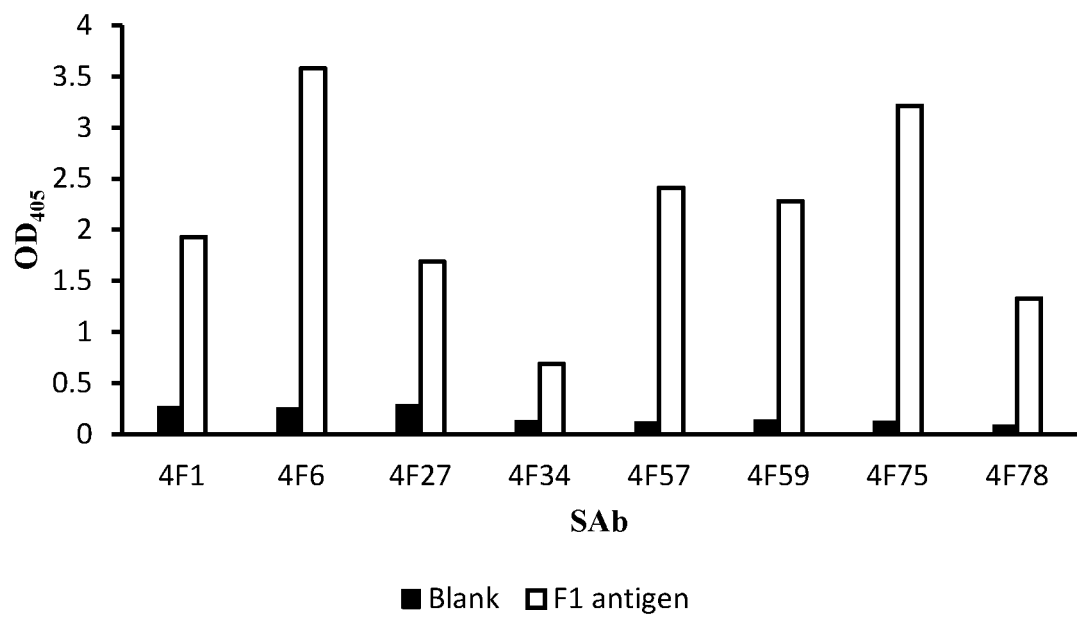
Figure 8:
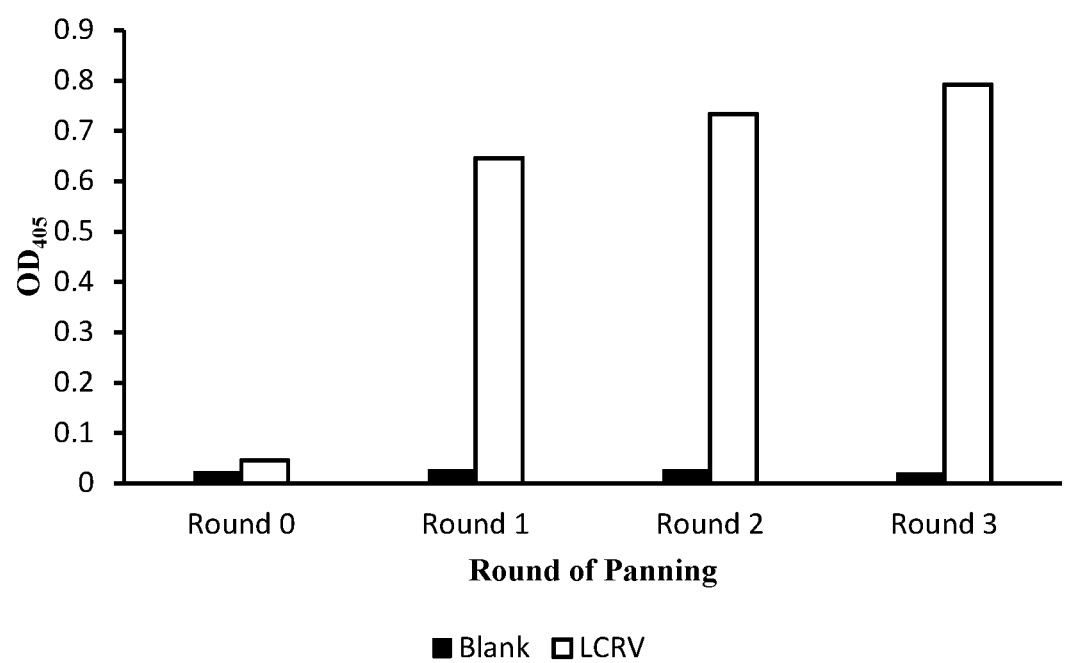
FIG. 8 is a graph of polyclonal phage ELISA testing after each round of panning to isolate LcrV-specific phages.
Figure 9A:
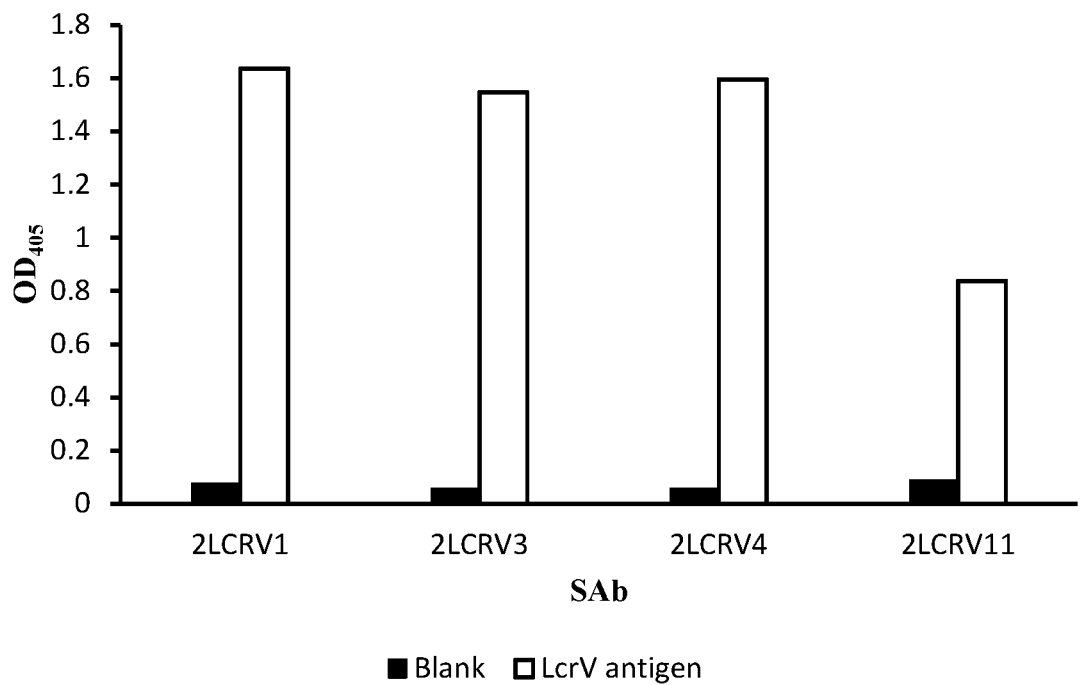
FIGS. 9A-B are graphs graph of the ELISA for the presence of LcrV-specific SAbs in the periplasmic extract of positive colonies.
Figure 9B:
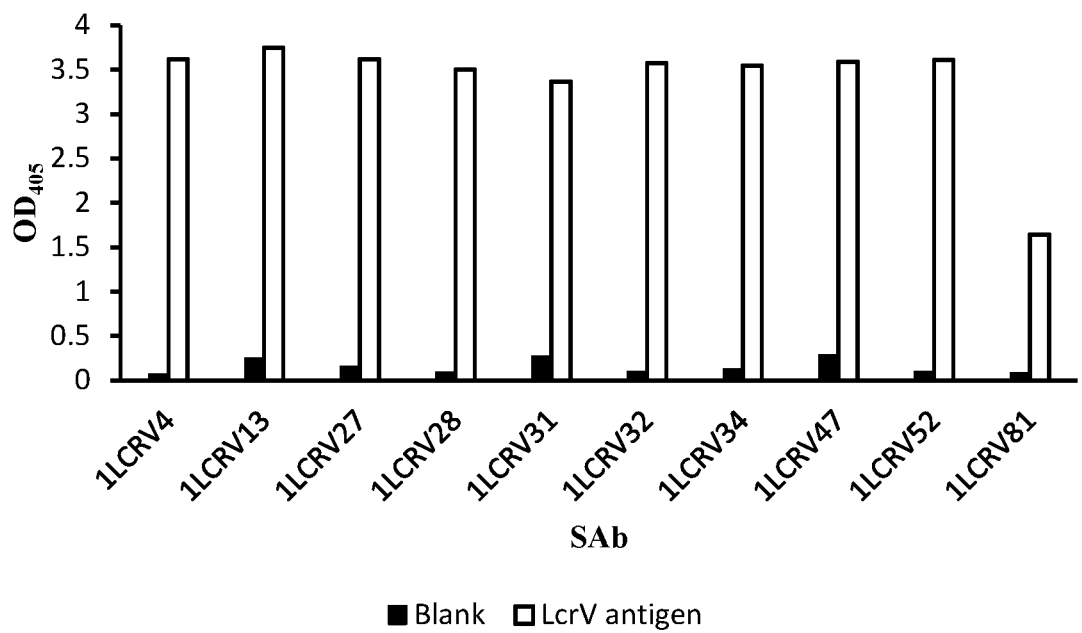

For the YscF antigen, the VHH library was subjected to four consecutive rounds of panning, performed on solid-phase coated antigen (concentration: 700 µg/ml, 30 µg/well, in 25 mM Tris (pH not tested), 150 mM NaCl, 0.05% Tween-20, and 1 mM EDTA). The enrichment for antigen-specific phages after each round of panning was assessed by comparing the number of phages eluted from antigen-coated wells with the number of phages eluted from negative control (only blocked) wells. The enrichment was also evaluated by polyclonal phage ELISA, which is shown in FIG. 4. These experiments suggested that the phage population was enriched for antigen-specific phages only after the third round of panning. In total, 385 individual colonies (95, 143, and 47 from second, third, and fourth rounds, respectively) were randomly selected and analyzed by ELISA for the presence of YscF-specific SAbs in their periplasmic extracts. Out of these 385 colonies, 19 colonies (all from the third round) scored positive. Sequencing of positive colonies identified seven different SAbs, and the ELISA results for these seven SAbs are shown in FIG. 5. The protein sequences of the seven exemplary YscF SAbs according to the present invention are shown in Table 3, and the nucleic acid sequences encoding the seven exemplary YscF SAbs are shown in Table 4.

FIG. 10 is a protein sequence alignment of the seven exemplary YscF SAbs listed in Table 3, and FIGS. 15A-C are sequence alignments of the nucleic acid sequences listed in Table 4. Gaps are introduced in the sequences contained in FIGS. 10 and 15A-C as needed in order to align the respective protein and nucleic acid sequences with one another. Referring to FIG. 10, the three CDRs are underlined in each sequence. The CDRs are defined according to the Kabat numbering system [Kabat, E. A., et al., (1991) Sequences of Proteins of Immunological Interest, Fifth Edition, NIH Publication No. 91-3242, US Department of Health and Human Services, Bethesda, MID]. The differences in the four FRs of each SAb (if any), as compared with 3YscF57 (SEQ ID NO:154), are in bold; any differences between the three CDRs of each SAb are not otherwise indicated. The seven exemplary YscF SAb sequences depicted in FIG. 10 and listed in Table 3 represent seven different groups i.e. they originate from seven clonally-unrelated B-cells.

Example 3: Isolation of F1 SAbs

For the F1 antigen, the library was subjected to four consecutive rounds of panning, performed on solid-phase coated antigen (concentration: 200 µg/ml, 20 µg/well, in the presence of 0.005% Tween-20). The enrichment for antigen-specific phages after each round of panning was assessed by comparing the number of phages eluted from antigen-coated wells with the number of phages eluted from negative control (blocked only) wells. The enrichment was also evaluated by polyclonal phage ELISA, which is shown in FIG. 6. These experiments suggested that the phage population was enriched for antigen-specific phages only after the third and fourth rounds of panning. In total, 285 individual colonies from second, third, and fourth rounds of panning (95 from each round) were randomly selected and analyzed by ELISA for the presence of F1-specific SAbs in their periplasmic extracts. Out of these 285 colonies, 55 scored positive (0, 29, and 26 from second, third, and fourth rounds, respectively). Sequencing of these 55 positive colonies identified 18 different SAbs, and the ELISA results for these 19 SAbs are shown in FIGS. 7A-B. The protein sequences of 18 exemplary F1 SAbs according to the present invention are shown in Table 5, and the nucleic acid sequences encoding the 18 F1 SAbs are shown in Table 6.

FIGS. 11A-B are protein sequence alignments of the 18 exemplary F1 SAbs listed in Table 5, and FIGS. 16A-H are sequence alignments of the nucleic acid sequences listed in Table 6. Gaps are introduced in the sequences in FIGS. 11A-B and 16A-H as needed in order to align the protein and nucleic acid sequences with one another. Referring to FIGS. 11A-B, the three CDRs are underlined in each sequence. The CDRs are defined according to the Kabat numbering system. The differences in the four FRs of each SAb (if any), as compared with 3F55 (SEQ ID NO:168), are in bold; any differences between the three CDRs of each SAb are not otherwise indicated. The 18 exemplary F1 SAbs shown in FIGS. 11A-B and listed in Table 5 represent 10 different groups, which are listed in Table 9. SAbs belonging to the same group are very similar, especially in the CDR3 region, and their amino acid sequences suggest that they are either from clonally-related B-cells resulting from somatic hypermutation or from the same B-cell with diversification due to PCR error during library construction.

Example 4: Isolation of LcrV SAbs

For the LcrV antigen, the library was subjected to three consecutive rounds of panning, performed on solid-phase coated antigen (concentration: 200 μg/ml, 20 μg/well). The enrichment for antigen-specific phages after each round of panning was assessed by comparing the number of phages eluted from antigen-coated wells with the number of phages eluted from negative control (blocked only) wells. The enrichment was also evaluated by polyclonal phage ELISA, which is shown in FIG. 8. These experiments suggested that the phage population was enriched for antigen-specific phages after the first, second, and third rounds of panning. 95 individual colonies from the second round of panning were randomly selected and analyzed by ELISA for the presence of LcrV-specific SAbs in their periplasmic extracts (not shown). Out of these 95 colonies, 85 scored positive. The VHHs from the 85 positive colonies were subjected to restriction fragment length polymorphism (RFLP) analysis using Hinf1 enzyme (not shown). Based on RFLP analysis, 40 colonies (several from each RFLP group) were selected for sequencing. Sequence analysis identified four different SAbs.

The high redundancy of the LcrV positive colonies identified after the second round of panning, together with the fact that the enrichment for antigen-specific phages was already good after the first round of panning, suggested that additional rounds of panning may have led to a loss of library diversity. To address this possibility and to identify additional unique sequences, 95 colonies from first round of panning were randomly selected and analyzed by ELISA for the presence of LcrV-specific SAbs in their periplasmic extracts, which is shown in FIGS. 9A-B. Out of these 95 colonies from the first round, 35 colonies were positive. These 35 colonies represented the four previously identified SAbs, as well as 10 novel sequences. The protein sequences of 14 exemplary LcrV SAbs according to the present invention are shown in Table 7, and the nucleic acid sequences encoding the 14 LcrV SAbs are shown in Table 8.

FIGS. 12A-B are the protein sequence alignment of the 14 exemplary LcrV SAbs listed in Table 7, and FIGS. 17A-F are sequence alignments of the nucleic acid sequences listed in Table 8. Gaps are introduced in the sequences in FIGS. 12A-B and 17A-F as needed in order to align the protein and nucleic acid sequences with one another. Referring to FIGS. 12A-B, the three CDRs are underlined in each sequence. The CDRs are defined according to the Kabat numbering system. The differences in the four FRs of each SAb (if any), as compared with 1LCRV32 (SEQ ID NO:204), are shown in bold; any differences between the three CDRs of each SAb are not otherwise indicated. The 14 exemplary LcrV SAbs shown in FIGS. 12A-B and listed in Table 7 represent six different groups, which are listed in Table 10. SAbs belonging to the same group are very similar, and their amino acid sequences suggest that they are from clonally-related B-cells resulting from somatic hypermutation or from the same B-cell with diversification due to PCR error during library construction.

Example: 5 Binding Kinetics of LcrV and F1 SAbs

Binding kinetics studies were conducted on selected LcrV and F1 SAbs. LcrV and F1 protein was immobilized on the surface of a BIACORE CM5 chip (GE Healthcare Biosciences), and each SAb was allowed to associate/dissociate with the appropriate antigen. The results of the binding kinetics study are shown in Table 11. Binding generally ranged from nM to pM, with the best two SAbs (LcrV-reactive SAbs SEQ ID NOs:209, 214) binding to the target in the mid-fM range. The binding constants of the seven LcrV SAbs from Table 11 (SEQ ID NOs:204, 209, 211, 214-217) are shown in Table 12. The $K_D$ is calculated as $k_d/k_a$ ("n.b."=no binding).

Figure 13A:
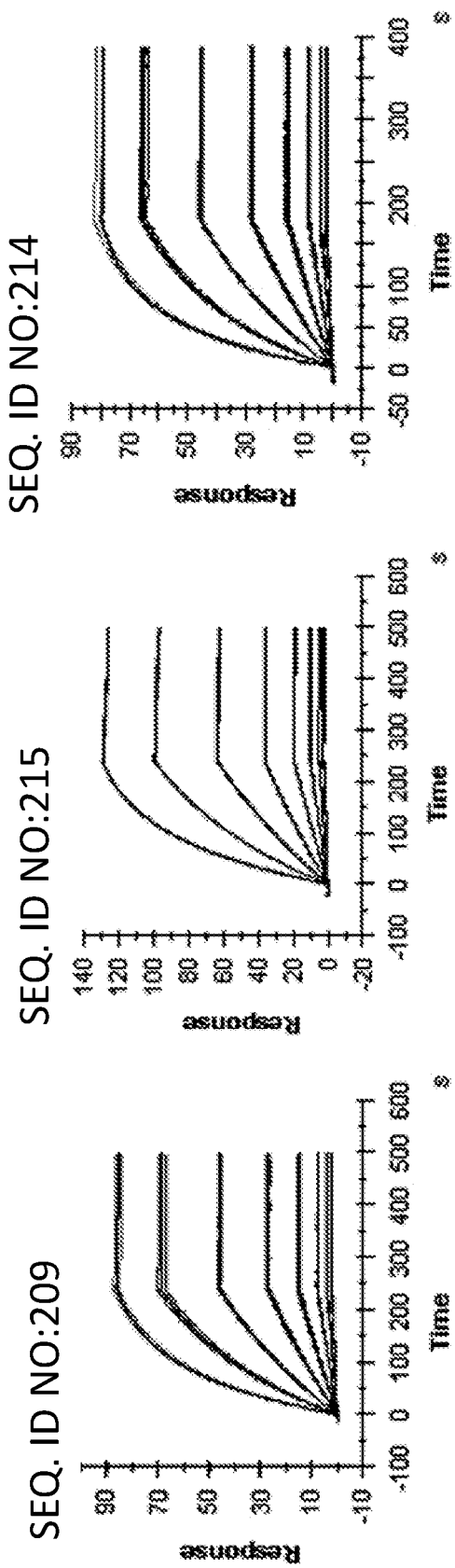
FIGS. 13A-B are the double-referenced sensorgrams obtained on the BIACORE T200 sensor instrument for selected LcrV SAbs.
Figure 13B:
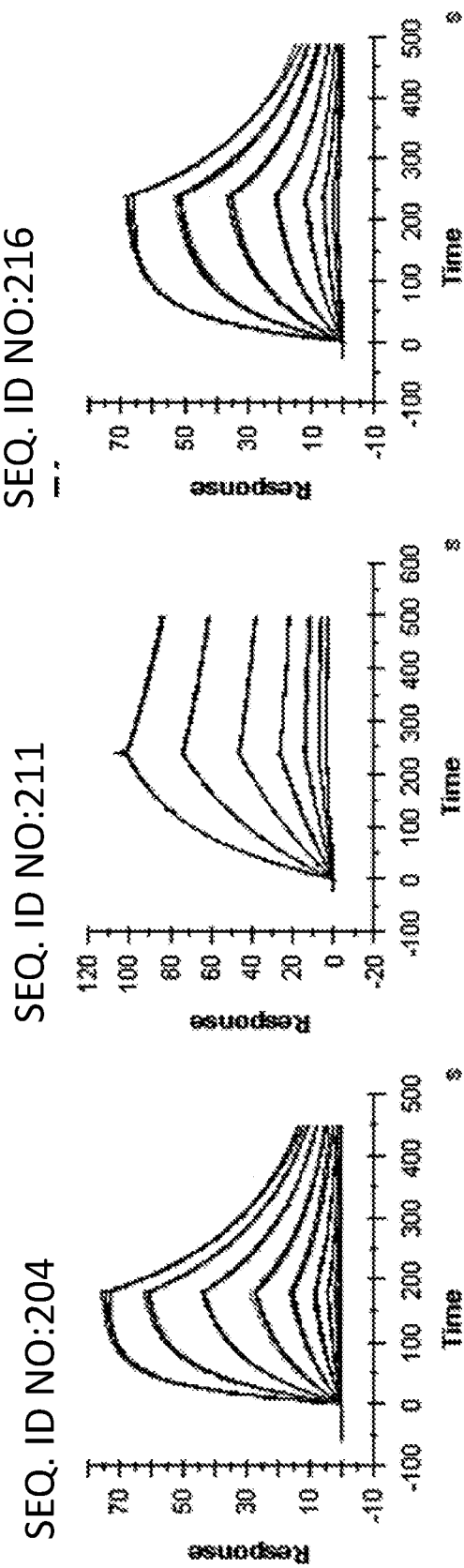

FIGS. 13A-B are the resulting double-referenced sensorgrams (colored by SAb concentration) obtained using a BIACORE T200 sensor instrument (General Electric Healthcare, United Kingdom) for six of the seven LcrV SAbs from Tables 11 and 12 (SEQ ID NOs:204, 209, 211, 214-217). A dissociation phase of 500 seconds was used for all concentrations of SAb. The overlaying curve fits are depicted in black, and the sensorgrams are based on a 1:1 binding model.

Figure 14A:
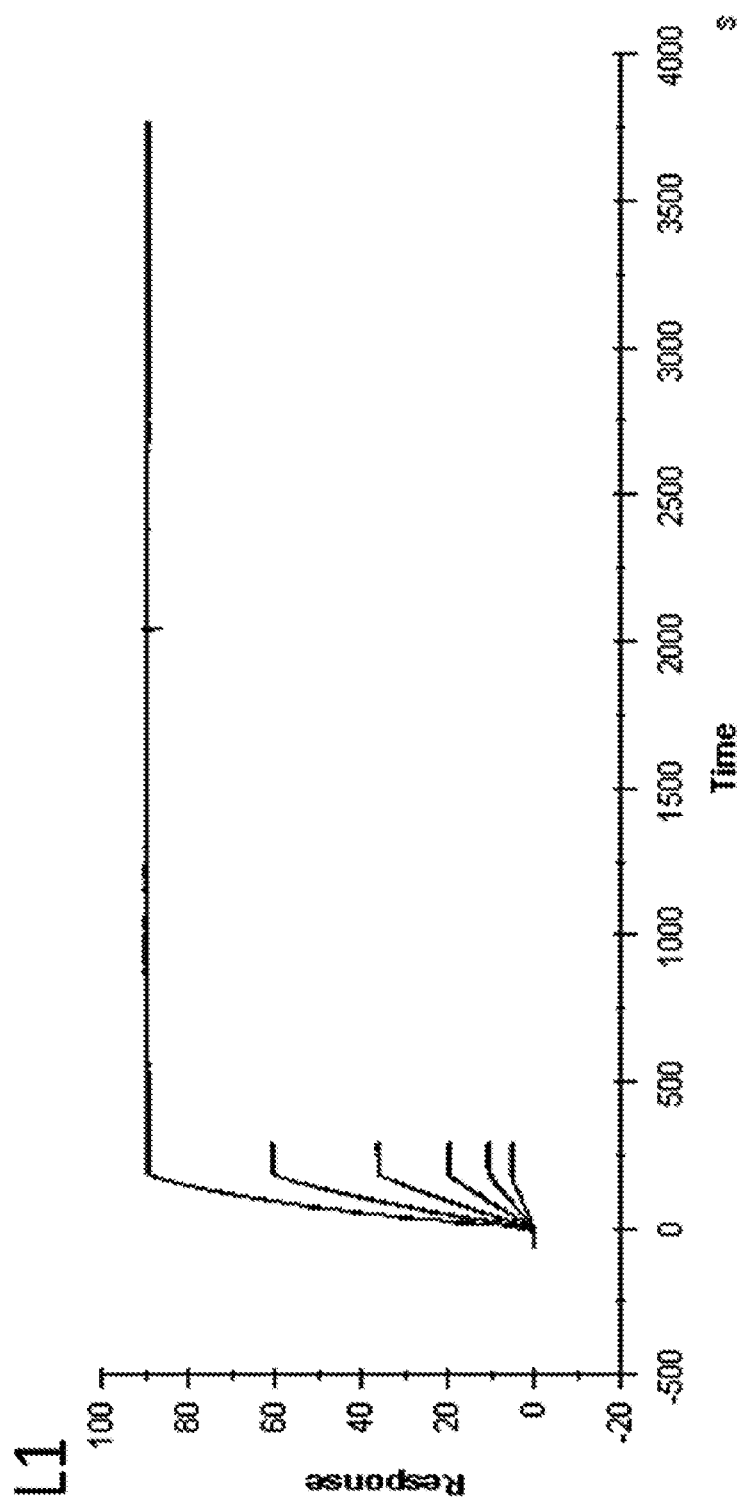
FIGS. 14A-B are the double-referenced sensorgrams obtained on the BIACORE T200 sensor instrument for the two LcrV SAbs demonstrating the best binding capabilities.
Figure 14B:
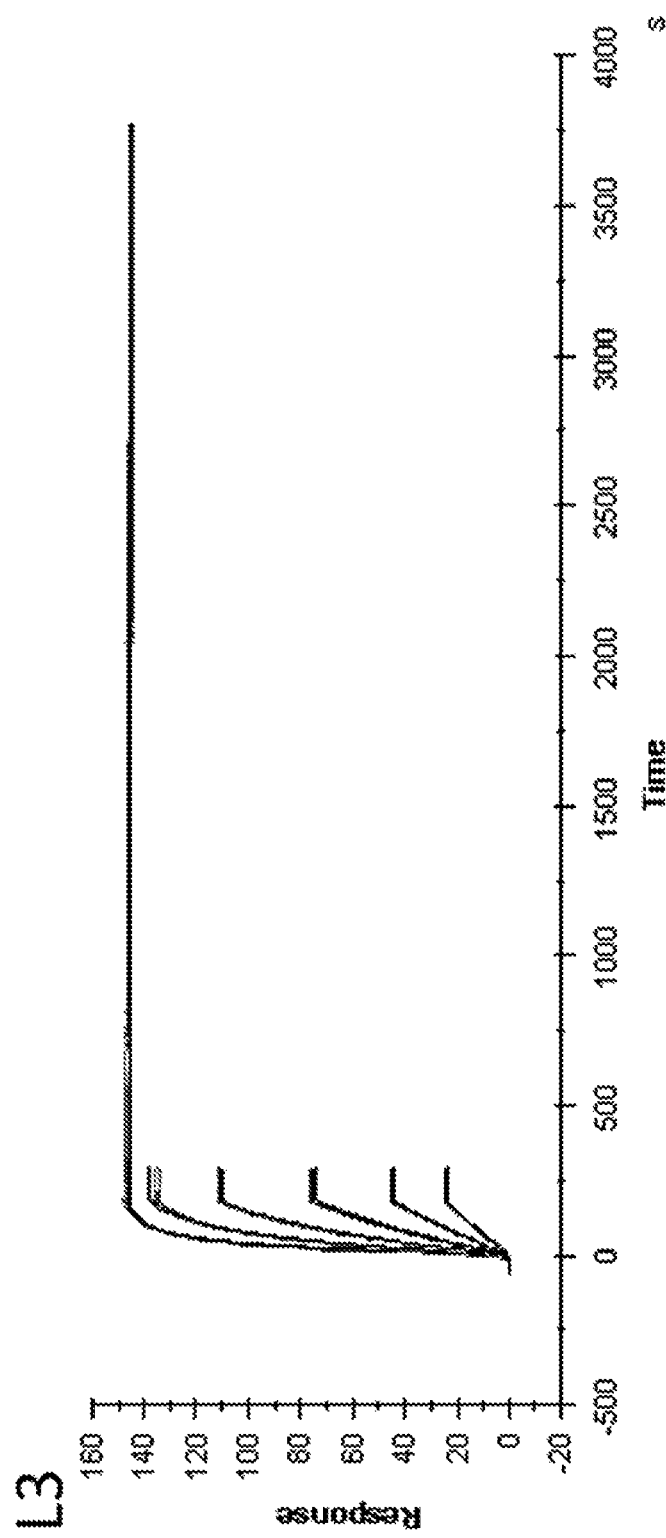

Of the described SAb sets, two SAbs (SEQ ID NOs:209, 214) demonstrate no discernible off rate ($k_d$) within the limits of THE BIACORE instrument analyses (see Tables 11 and 12). In a second test, LcrV was immobilized on the surface of a BIACORE CM5 chip, and LcrV-reactive SAbs SEQ ID NOs:209 and 214 were allowed to associate/dissociate. A dissociation phase of 120 seconds was used for all concentrations of SAb except the highest concentration, for which a 3600 second dissociation was used. FIGS. 14A-B are the double-referenced sensorgrams (colored by SAb concentration) obtained on the BIACORE T200 sensor instrument with overlaying curve fits (black), based on a 1:1 binding model. These data indicate that the SAb sequences of SEQ ID NOs:209 and 214 bind to the Y. pestis LcrV protein extremely and unusually tightly. Due to the nature of these two SAbs, both could bind to the Y. pestis bacteria in a manner that may make infection and/or replication difficult or impossible.

The present invention includes SAbs against at least one Y. pestis surface protein or antigen and the nucleotide sequences that encode the SAbs. The Y. pestis surface protein may include YscF, F1, and/or LcrV. The present invention includes a composition comprising a single SAb or a mixture of two or more different SAbs. For compositions comprising a mixture of two or more different SAbs, all of the SAbs may be against a single Y. pestis surface protein (single-antigen), or the SAbs may be against different epitopes on the same Y. pestis surface protein (single-antigen, multi-epitope). The mixture of two or more different SAbs may further comprise SAbs against two or more Y. pestis surface proteins (multi-antigen).

In one embodiment of the present invention, SAbs against at least one Y. pestis YscF epitope may comprise one each of a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60. In another embodiment, SAbs against at least one Y. pestis YscF epitope may comprise one each of an FR1 sequence selected from the group consisting of SEQ ID NOs:79-102; a CDR1 sequence selected from the group consisting of SEQ ID NOs:1-7; an FR2 sequence selected from the group consisting of SEQ ID NOs:103-120; a CDR2 sequence selected from the group consisting of SEQ ID NOs:27-33; an FR3 sequence selected from the group consisting of SEQ ID NOs:121-146; a CDR3 sequence selected from the group consisting of SEQ ID NOs:54-60; and an FR4 sequence selected from the group consisting of SEQ ID NOs:147-153. In a further embodiment, SAbs against at least one Y. pestis YscF epitope may comprise the specific arrangement of FRs and CDRs embodied in SEQ ID NOs:154-160. The present invention further includes isolated nucleotide sequences selected from the group consisting of SEQ ID NOs:161-167 that encode the SAbs comprising SEQ ID NOs:154-160.

In another embodiment, SAbs against at least one Y. pestis F1 epitope may comprise one each of a CDR1 sequence selected from the group consisting of SEQ ID NOs:8-19; a CDR2 sequence selected from the group consisting of SEQ ID NOs:34-47; and a CDR3 sequence selected from the group consisting of SEQ ID NOs:61-71, AEY, and PGY. In another embodiment, SAbs against at least one Y. pestis F1 epitope may comprise one each of an FR1 sequence selected from the group consisting of SEQ ID NOs:79-102; a CDR1 sequence selected from the group consisting of SEQ ID NOs:8-19; an FR2 sequence selected from the group consisting of SEQ ID NOs:103-120; a CDR2 sequence selected from the group consisting of SEQ ID NOs:34-47; an FR3 sequence selected from the group consisting of SEQ ID NOs:121-146; a CDR3 sequence selected from the group consisting of SEQ ID NOs:61-71, AEY, and PGY; and an FR4 sequence selected from the group consisting of SEQ ID NOs:147-153. In a further embodiment, SAbs against at least one Y. pestis F1 epitope comprise the specific arrangement of FRs and CDRs embodied in SEQ ID NOs:168-185. The present invention further includes isolated nucleotide sequences selected from the group consisting of SEQ ID NOs:186-203 that encode the SAbs comprising SEQ ID NOs:168-185.

In a further embodiment, SAbs against at least one Y. pestis LcrV epitope may comprise one each of a CDR1 sequence selected from the group consisting of SEQ ID NOs:20-26; a CDR2 sequence selected from the group consisting of SEQ ID NOs:48-53; and a CDR3 sequence selected from the group consisting of SEQ ID NOs:72-78 and GNI. In another embodiment, SAbs against at least one Y. pestis LcrV epitope may comprise one each of an FR1 sequence selected from the group consisting of SEQ ID NOs:79-102; a CDR1 sequence selected from the group consisting of SEQ ID NOs:20-26; an FR2 sequence selected from the group consisting of SEQ ID NOs:103-120; a CDR2 sequence selected from the group consisting of SEQ ID NOs:48-53; an FR3 sequence selected from the group consisting of SEQ ID NOs:121-146; a CDR3 sequence selected from the group consisting of SEQ ID NOs:72-78 and GNI; and an FR4 sequence selected from the group consisting of SEQ ID NOs:147-153. In a further embodiment, SAbs against at least one Y. pestis LcrV epitope may comprise the specific arrangement of FRs and CDRs embodied in SEQ ID NOs:204-217. The present invention further includes isolated nucleotide sequences selected from the group consisting of SEQ ID NOs:218-231 that encode the SAbs comprising SEQ ID NOs:204-217.

In an alternative embodiment, the present invention includes one or more SAbs against Y. pestis YscF, with each SAb comprising a CDR1 sequence, a CDR2 sequence, and a CDR3 sequence respectively having at least 15% sequence identity with a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60, in which the SAbs retain sufficient affinity for at least one of a *Y. pestis* YscF antigen or a *Y. pestis* YscF epitope. The present invention further includes one or more SAbs against *Y. pestis* YscF having at least 15% sequence identity with SEQ ID NOs:154-160, in which the SAbs retain sufficient affinity for at least one of a *Y. pestis* YscF antigen or a *Y. pestis* YscF epitope.

The present invention further includes one or more SAbs against *Y. pestis* F1, with each SAb comprising a CDR1 sequence, a CDR2 sequence, and a CDR3 sequence respectively having at least 15% sequence identity with at least one of a CDR1 sequence selected from the group consisting of SEQ ID NOs:8-19, a CDR2 sequence selected from the group consisting of SEQ ID NOs:34-47, and a CDR3 sequence selected from the group consisting of SEQ ID NOs:61-71, AEY, and PGY, in which the SAbs retain sufficient affinity for at least one of a *Y. pestis* F1 antigen or a *Y. pestis* F1 epitope. The present invention further includes one or more SAbs against *Y. pestis* F1 having at least 15% sequence identity with SEQ ID NOs: 168-185, in which the SAbs retain sufficient affinity for at least one of a *Y. pestis* F1 antigen or a *Y. pestis* F1 epitope The present invention further includes one or more SAbs against *Y. pestis* LcrV, with each SAb comprising a CDR1 sequence, a CDR2 sequence, and a CDR3 sequence respectively having at least 15% sequence identity with at least one of a CDR1 sequence selected from the group consisting of SEQ ID NOs:20-26, a CDR2 sequence selected from the group consisting of SEQ ID NOs:48-53, and a CDR3 sequence selected from the group consisting of SEQ ID NOs:72-78 and GNI, in which the SAbs retain sufficient affinity for at least one of a *Y. pestis* LcrV antigen or a *Y. pestis* LcrV epitope. The present invention further includes one or more SAbs against *Y. pestis* LcrV having at least 15% sequence identity with SEQ ID NOs: 204-217, in which the SAbs retain sufficient affinity for at least one of a *Y. pestis* LcrV antigen or a *Y. pestis* LcrV epitope.

In an another embodiment, the present invention further includes a polypeptide, which is used herein to refer to a structure comprising two or more of any of the above-described SAbs against *Y. pestis* YscF, F1, and/or LcrV in which the two or more SAbs are joined together. In one embodiment, the polypeptide may comprise a fusion protein that is created by joining together two or more SAbs at the genetic level. Two or more nucleic acid sequences encoding for two or more SAbs may be spliced together, and translation of the spliced nucleic acid sequence creates a longer, multi-antigen and/or multi-epitope fusion protein. The fusion protein may contain up to four SAbs joined end-to-end in a substantially linear fashion, similar to beads on a string.

In one embodiment, the fusion protein comprises SAbs that are all against a single *Y. pestis* surface protein or antigen i.e. a single-antigen fusion protein against either YscF, F1, or LcrV. In a further embodiment, this single-antigen fusion protein further comprises SAbs that bind to two or more different epitopes (multi-epitope, single-antigen) on the single antigen. In another embodiment, the fusion protein may comprise SAbs against two or more different *Y. pestis* surface proteins i.e. a multi-antigen fusion protein. The multi-antigen fusion protein may also comprise SAbs that bind to two or more different epitopes (multi-epitope, multi-antigen) on the same antigen(s). In use, each individual fusion protein molecule may bind to one *Y. pestis* surface protein molecule, or the individual fusion protein molecule may be bound to two or more separate *Y. pestis* surface protein molecules. Use of a multi-antigen and/or multi-epitope fusion protein may increase avidity in enzyme immunosorbent assays.

In another embodiment, the polypeptide may be created by joining two or more SAbs together with a protein or chemical linker to create a multivalent protein complex. For example, a linker molecule such as the verotoxin 1B-subunit may be used to create high avidity, pentavalent SAb complexes similar to keys on a key ring. In one embodiment, the multivalent protein complex may contain SAbs that are all against a single *Y. pestis* surface protein or antigen i.e. a single-antigen multivalent protein complex. This single-antigen multivalent protein complex may further comprise SAbs that bind to two or more different epitopes (multi-epitope, single-antigen) on the single antigen. In another embodiment, the multivalent protein complex may comprise SAbs against two or more different *Y. pestis* surface proteins i.e. a multi-antigen multivalent protein complex. The multi-antigen multivalent protein complex may further comprise SAbs that bind to two or more different epitopes (multi-epitope, multi-antigen) on the same antigen. In use, each multivalent protein complex may bind to one *Y. pestis* surface protein molecule, or the multivalent protein complex may be bound to two or more separate *Y. pestis* surface protein molecules. These multi-antigen and/or multi-epitope multivalent protein complexes may generally demonstrate increased affinity for their respective epitope and/or antigen target(s) and may have numerous applications for biomarker assays or proteomics.

In one embodiment of the present invention, polypeptides as described herein comprise at least two SAbs, with the SAbs being selected from the following groups: (1) SAbs comprising one each of a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60; (2) SAbs comprising one each of a CDR1 sequence selected from the group consisting of SEQ ID NOs:8-19; a CDR2 sequence selected from the group consisting of SEQ ID NOs:34-47; and a CDR3 sequence selected from the group consisting of SEQ ID NOs:61-71, AEY, and PGY; and (3) SAbs comprising one each of a CDR1 sequence selected from the group consisting of SEQ ID NOs:20-26; a CDR2 sequence selected from the group consisting of SEQ ID NOs:48-53; and a CDR3 sequence selected from the group consisting of SEQ ID NOs:72-78 and GNI.

In a further embodiment, the polypeptides comprise at least two SAbs selected from the group consisting of: (1) SAbs comprising one each of a CDR1 sequence selected from the group consisting of sequences having at least 15% sequence identity with SEQ ID NOs:1-7; a CDR2 sequence selected from the group consisting of sequences having at least 15% sequence identity with SEQ ID NOs: 27-33; and a CDR3 sequence selected from the group consisting of sequences having at least 15% sequence identity with SEQ ID NOs:54-60; (2) SAbs comprising one each of a CDR1 sequence selected from the group consisting of sequences having at least 15% sequence identity with SEQ ID NOs: 8-19; a CDR2 sequence selected from the group consisting of sequences having at least 15% sequence identity with SEQ ID NOs: 34-47; and a CDR3 sequence selected from the group consisting of sequences having at least 15% sequence identity with SEQ ID NOs: 61-71; and (3) SAbs comprising one each of a CDR1 sequence selected from the group consisting of sequences having at least 15% sequence identity with SEQ ID NOs: 20-26; a CDR2 sequence selected from the group consisting of sequences having at least 15% sequence identity with SEQ ID NOs: 48-53; and a CDR3 sequence selected from the group consisting of sequences having at least 15% sequence identity with SEQ ID NOs: 72-78.

In another embodiment, the polypeptides may comprise at least two SAbs, with the SAbs being selected from the following groups: (1) SAbs comprising one set of CDR1, CDR2, and CDR3 sequences (as described above with respect to polypeptides according to the present invention) and one each of an FR1 sequence selected from the group consisting of SEQ ID NOs:79-102, an FR2 sequence selected from the group consisting of SEQ ID NOs:103-120, an FR3 sequence selected from the group consisting of SEQ ID NOs:121-146, and an FR4 sequence selected from the group consisting of SEQ ID NOs:147-153; and (2) SAbs selected from the group consisting of SEQ ID NOs:154-160, 168-185, and 204-217 and sequences having at least 15% sequence identity with SEQ ID NOs:154-160, 168-185, and 204-217.

In another embodiment, any of the SAbs or polypeptides according to the present invention may further comprise a protein tag, a protein domain tag, or a chemical tag. These tags generally comprise one or more additional amino acids or chemical molecules or residues that may be placed using known methods on the C- or N-terminus of the SAb or polypeptide without altering the activity or functionality of the SAb or polypeptide. The tag may facilitate purification of the SAb or polypeptide, direct absorption and/or excretion in the body, and/or facilitate use in a variety of applications such as detecting and monitoring *Y. pestis*. The tag may include, but is not limited to, a histidine tag (HIS tag) and a poly-lysine tag.

The present invention further includes a method of preventing or treating a *Y. pestis* infection in a patient. *Y. pestis* infections are frequently difficult to properly diagnose, which can result in delayed treatment, and a low toxicity treatment such as the presently disclosed SAbs may provide a valuable tool for cases of suspected *Y. pestis* exposure and/or infection and/or for patients presenting with ambiguous symptoms. The method comprises identifying a patient who is suspected of having been exposed to and/or infected with *Y. pestis*, and administering to the patient a pharmaceutically active amount of one or more of the SAbs and/or polypeptides according to the present invention. As used throughout, a "pharmaceutically active amount" refers generally to an amount that upon administration to the patient, is capable of providing directly or indirectly, one or more of the effects or activities disclosed herein. In one embodiment, the SAb(s) and/or polypeptide(s) may be administered as a form of passive immunotherapy in which the SAb(s) and/or polypeptide(s) are administered to the patient prior to at least one of exposure to or infection with *Y. pestis*. In another embodiment, the SAb(s) and/or polypeptide(s) may be administered after the patient is exposed to or infected with *Y. pestis*. The SAb(s) and/or polypeptide(s). In all embodiments of the methods, the SAb(s) and/or polypeptide(s) may be capable of being self-administered and may be administered to the patient using known techniques including, but not limited to, intravenous and subcutaneous injection, oral ingestion, inhalation, and topical administration. The ability to self-administer the SAb(s) and/or polypeptide(s) may be particularly useful in the case of an outbreak or attack where access to medical personnel and treatment may be limited.

The present invention further includes a method of detecting and/or diagnosing a *Y. pestis* infection using one of more of the SAbs and/or polypeptides herein described. The method may include detection of *Y. pestis* and diagnosis of the infection using known in vivo and/or in vitro assays such as enzyme linked immunosorbent assays (ELISAs), dot blot assays, and other suitable immunoassays. The *Y. pestis* SAb(s) and/or polypeptide(s) may, for example, be used as a primary antibody or a capture antibody in an ELISA for the detection/diagnosis of a *Y. pestis* infection. The SAb(s) and/or polypeptide(s) according to the present invention may further be coupled to one or more enzymes or markers for use in imaging.

The present invention further includes devices and methods for the identification and detection of *Y. pestis* on a surface and/or in an environment A device for the environmental detection and/or quantification of *Y. pestis* may comprise one or more of the SAbs or polypeptides according to the present invention, with the SAb(s) and/or polypeptide(s) being used as a capture element. A method of identifying and detecting *Y. pestis* using the device comprises contacting one or more of the SAbs or polypeptides with an unknown target and detecting binding between the SAbs or polypeptides and the unknown target to identify the unknown target as *Y. pestis*. The method may further comprise use of the device to quantify an amount of *Y. pestis* on the surface and/or in the environment.

TABLE 1

Amino Acid Code

| | | | | | |
|---|---|---|---|---|---|
| Alanine | Ala | A | Methionine | Met | M |
| Cysteine | Cys | C | Asparagine | Asn | N |
| Aspartic Acid | Asp | D | Proline | Pro | P |
| Glutamic Acid | Glu | E | Glutamine | Gln | Q |
| Phenylalanine | Phe | F | Arginine | Arg | R |
| Glycine | Gly | G | Serine | Ser | S |
| Histidine | His | H | Threonine | Thr | T |
| Isoleucine | Ile | I | Valine | Val | V |
| Lysine | Lys | K | Tryptophan | Trp | W |
| Leucine | Leu | L | Tyrosine | Tyr | Y |

TABLE 2

Exemplary Combinations of FR and CDR Sequences

| ID # | FR1 | ID # | CDR1 | ID # | FR2 | ID # | CDR2 | ID # | FR3 | ID # | CDR3 | ID # | FR4 |
|---|---|---|---|---|---|---|---|---|---|---|---|---|---|
| | | | | | YscF SAb Sequences | | | | | | | | |
| 79 | QVQLQESGG GLVQAGGSL RLSCAAS | 1 | GRTWR AYYMG | 103 | WFRQA PGKER EFVA | 27 | VMSRSG GTTSYA DSVKG | 121 | RFTISRDNAKN TVYLQMNNLA PEDTATYYCKA | 54 | GGGMY GPDLYG MTY | 147 | WGKGT QVTVSS |
| 80 | QVQLQESGG GLVQAGGSL RLSCAAS | 2 | GRAFS NYAMA | 103 | WFRQA PGKER EFVA | 28 | ANWRSG GLTDYA DSVKG | 122 | RFTISRDDAKN TVYLQMNSLK PEDTAVYYCAA | 55 | GGGSRW YGRTTA SWYDY | 148 | WGQGT QVTVSS |

TABLE 2-continued

Exemplary Combinations of FR and CDR Sequences

| ID # | FR1 | ID # | CDR1 | ID # | FR2 | ID # | CDR2 | ID # | FR3 | ID # | CDR3 | ID # | FR4 |
|---|---|---|---|---|---|---|---|---|---|---|---|---|---|
| 81 | QVQLQESGGGLVQAGGSLRLSCAAS | 3 | GRTFSRYAMG | 103 | WFRQAPGKEREFVA | 29 | AISWSGSSTYYADSVKG | 123 | RFTISRDHAKNVMYLQMNGLKPEDTGVYVCAR | 56 | PAYGLRPPYNY | 149 | RGQGTQVTVSS |
| 82 | QVQLQESGGGLVQAGGSLKLSCTAS | 4 | QRTFSRYSLG | 104 | WFRQAPGEERVFVA | 30 | ATTWGISSDYADSVKG | 124 | RFTISRDNAKNTGYLQMNNLKPEDTGVYYCAA | 57 | GRSSWFAPWLTPYEYDY | 150 | WGRGTQVTVSS |
| 79 | QVQLQESGGGLVQAGGSLRLSCAAS | 5 | GRTFSSHAMA | 105 | WFRQGPGEERQFLA | 31 | AIRWNGDNIHYSDSAKG | 125 | RFTISRDLAKNTLYLQMNSLKPEDTAVYYCAR | 58 | GVYDY | 147 | WGQGTQVTVSS |
| 83 | QVQLQESGGGLVQAGDSRILSCTAS | 6 | GRTFGRPFRYTMG | 106 | WFRRAPGKEREFVG | 32 | GITRSGNNIYYSDSVKG | 126 | RFTISRDNAKNTVYLQMNSLKPEDTAVYYCNA | 59 | DWGWRNY | 148 | WGQGTQVTVSS |
| 84 | QVQLQESGGGLVQAGGSLRLACAAS | 7 | GETVDDLAIG | 107 | WFRQAPGKEREEOS | 33 | CISGSDGSTYYADSLSG | 127 | RFTISRDNVKNTVYLQMNSLKLEDTAVYYCYA | 60 | EIYDRRWYRNDY | 148 | WGQGTQVTVSS |

F1 SAb Sequences

| ID # | FR1 | ID # | CDR1 | ID # | FR2 | ID # | CDR2 | ID # | FR3 | ID # | CDR3 | ID # | FR4 |
|---|---|---|---|---|---|---|---|---|---|---|---|---|---|
| 81 | QVQLQESGGGLVQAGGSLRLSCAVS | 8 | GMMYIREAIR | 108 | WYRQAPGKQREWVA | 34 | FVSSTGNPRYTDSVKG | 128 | RFTISRDNAKNTVYLQMNSLTPEDTAVYYCNT | 61 | YLGSRDY | 148 | WGQGTQVTVSS |
| 85 | QVQLQESGGGLVQPGGSLRLSCAVS | 9 | GMMYIRYTMR | 108 | WYRQAPGKQREWVA | 35 | VVSSTGNPHYADSVKG | 128 | RFTISRDNAKNTVYLQMNSLTPEDTAVYYCNT | 61 | YLGSRDY | 148 | WGQGTQVTVSS |
| 86 | QVQLQESGGGLVRPGGSLRLSCAVS | 10 | GRAVNRYHMH | 109 | WYRQAPGKQREWVT | 36 | EISVGGTTNYAGSVKG | 129 | RFTVSRDNAKNTYLQMNSLKPEDTAVYYCNS | * | AEY | 148 | WGQGTQVTVSS |
| 87 | QVQLQESGGGSVQPGGSLSLSCSAS | 11 | GIIFSDYALT | 108 | WYRQAPGKQREWVA | 37 | QITRSQNINYTGSVKG | 130 | RFTVSRDNAKNTVHLQMNSLKPEDTAVYYCHA | 62 | YDGRRPPY | 148 | WGQGTQVTVSS |
| 87 | QVQLQESGGGSVQPGGSLSLSCSAS | 11 | GIIFSDYALT | 108 | WYRQAPGKQREWVA | 37 | QITRSQNINYTGSVKG | 130 | RFTVSRDNAKNTVHLQMNSLKPEDTAVYYCHA | 63 | YDGRRRPY | | WGQGTQVTVSS |
| 88 | QVQLQESGGGLVQPGGSLSLSCSAS | 11 | GIIFSDYALT | 108 | WYRQAPGKQREWVA | 37 | QITRSQNINYTGSVKG | 130 | RFTVSRDNAKNTVHLQMNSLKPEDTAVYYCHA | 62 | YDGRRPPY | 148 | WGQGTGVTVSS |
| 88 | QVQLQESGGGLVQPGGSLSLSCSAS | 11 | GIIFSDYALT | 108 | WYRQAPGKQREWVA | 38 | QITRRQNINYTGSVKG | 130 | RFTVSRDNAKNTVHLQMNSLKPEDTAVYYCHA | 64 | YDGRRSPY | 148 | WGQGTQVTVSS |
| 89 | QVQLQESGGGLVQPGGSLRLSCSAS | 11 | GIIFSDYALT | 108 | WYRQAPGKQREWVA | 37 | QITRSQNINYTGSVKG | 131 | RFTVSRDNAKNTVHLQMNSLKPEDAAVYYCHA | 62 | YDGRRPPY | 148 | WGQGTQVTVSS |
| 90 | QVQLQESGGGLVQPGGSLRLSCAAS | 12 | ARIFSIYAMV | 108 | WYRQAPGKQREWVA | 39 | AITTGGTTNYADSVKG | 126 | RFTISRDNAKNTVYLQMNSLKPEDTAVYYCHA | * | PGY | 148 | WGQGTQVTVSS |
| 90 | QVQLQESGGGLVQPGGSLRLSCAAS | 13 | GVIASISVLR | 110 | WYRQTPGKTRDWVA | 40 | IITSGGNTRYADSVKG | 132 | RFTTSRDNARNTVYLQMNSLKPEDTAVYYCNT | 65 | LVGAKDY | 148 | WGQGTQVTVSS |
| 91 | QVQLQESGGGLVRPGGSLRLSCEAS | 14 | GTTFRSLVMK | 111 | WYRQAPGKEREWVA | 41 | FISSPGDRTRYTEAVKG | 133 | RFTISRDNAKNALYLQMNGLKPEDTAVYYCNA | 66 | NGIY | 147 | WGKGTQVTVSS |
| 92 | QVQLQESGGGLVQSGDSLRLSCAAS | 15 | GRTFSNYAMS | 112 | WVRQAPGKGLEWVS | 42 | TINSGGGSTSYAYSVKG | 134 | RFTISRDNAKNTYLQMNSLKPEDTAVYYCAK | 67 | TASHIP | 151 | LSQGTQVTVSS |
| 90 | QVQLQESGGGLVQPGGSLRLSCAAS | 15 | GFTFSNYAMS | 112 | WVRQAPGKGLEWVS | 43 | TINIGGSTSYADSVKG | 134 | RFTISRDNAKNTLYLQMNSLKPEDTAVYYCAK | 67 | TASHIP | 151 | LSQGTQVTVSS |
| 90 | QVQLQESGGGLVQPGGSLRLSCAAS | 16 | GFTFRNYAMS | 112 | WVRQAPGKGLEWVS | 44 | TINGGGGITSYADSVKG | 135 | RFTISRDNAKNTMYLQMNSLKPEDTAVYYCAQ | 68 | TARDSRDS | 149 | RGQGTQVTVSS |
| 90 | QVQLQESGGGLVQPGGSLRLSCAAS | 17 | GFTFSSYAMS | 113 | WVRLAPGKGLEWVS | 45 | TINIAGGITSYADSVKG | 134 | RFTISRDNAKNTLYLQMNSLKPEDTAVYYCAK | 69 | TAANWSAQ | 149 | RGQGTQVTVSS |
| 90 | QVQLQESGGGLVQPGGSLRLSCAAS | 17 | GFTFSSYAMS | 112 | WVRQAPGKGLEWVS | 46 | TINMGGGTTSYADSVKG | 136 | RFTISRHNAKNTLYLQMNSLKPEDTAVYYCAK | 70 | TAGNWSAQ | 149 | RGQGTQVTVSS |
| 90 | QVQLQESGGGLVQPGGSLRLSCAAS | 18 | GFTFSTSAMS | 114 | WIRQPPGKAREVVA | 47 | TITSAGGSISYVNSVKG | 137 | RFTISRDNAKNTLYLQMNMLKPEDTAVYYCAR | 71 | LVNLAQ | 152 | TGQGTQVTVSS |
| 90 | QVQLQESGGGLVQPGGSLRLSCAAS | 19 | GFTFSTNAMS | 114 | WIRQPPGKAREVVA | 47 | TITSAGGSISYVNSVKG | 137 | RFTISRDNAKNTLYLQMNMLKPEDTAVYYCAR | 71 | LVNLAQ | 152 | TGQGTQVTVSS |

TABLE 2-continued

Exemplary Combinations of FR and CDR Sequences

LerV SAb Sequences

| ID # | FR1 | ID # | CDR1 | ID # | FR2 | ID # | CDR2 | ID # | FR3 | ID # | CDR3 | ID # | FR4 |
|---|---|---|---|---|---|---|---|---|---|---|---|---|---|
| 93 | QVQLQESGGGMVEPGGSLRLSCAAS | 20 | GFRFSSYAMS | 115 | WVRQAPGKGLERVS | 48 | AINSDGDKTSYADSVKG | 138 | RFTISRDNARNTLYLQMSNLKPEDTAVYYCAD | 72 | RDLYCSGSMCKDVLGGARYDF | 149 | RGQGTQVTVSS |
| 94 | QVQLQESGGGLVEPGGSLRLSCAAS | 20 | GFRFSSYAMS | 115 | WVRQAPGKGLERVS | 48 | AINSDGDKTSYADSVKG | 138 | RFTISRDNARNTLYLQMSNLKPEDTAVYYCAD | 72 | RDLYCSGSMCKDVLGGARYDF | 149 | RGQGTQVTVSS |
| 93 | QVQLQESGGGMVEPGGSLRLSCAAS | 20 | GFRFSSYAMS | 115 | WVRQAPGKGLERVS | 48 | AINSDGDKTSYADSVKG | 139 | RFTISRDNARNTLYLQMNNLKPEDTAVYYCAD | 72 | RDLYCSGSMCKDVLGGARYDF | 149 | RGQGTQVTVSS |
| 95 | QVQLQESGGGLVQSGESLRLSCAAS | 21 | GLRFSSYAMS | 115 | WVRQAPGKGLERVS | 48 | AINSDGDKTSYADSVKG | 138 | RFTISRDNARNTLYLQMSNLKPEDTAVYYCAD | 72 | RDLYCSGSMCKDVLGGARYDF | 149 | RGQGTQVTVSS |
| 96 | QVQLQESGGGLVQPGGSLKLSCAAS | 22 | GFTFNWYTMA | 116 | WYRQVPGEERKMVA | 49 | TITGASGDTKYADSVKG | 140 | RFTISRDNAKNTVTLQMNSLKPGDAAVYYCHA | 73 | YLTYDSGSVKGVNY | 148 | WGQGTQVTVSS |
| 97 | QVQLQESGGGLVRPGGSLKLSCAAS | 22 | GFTFNWYTMA | 116 | WYRQVPGEERKMVA | 49 | TITGASGDTKYADSVKG | 141 | RFTISRDNAKNTVTLQMNSLKPGDTAVYYCHA | 73 | YLTYDSGSVKGVNY | 148 | WGQGTQVTVSS |
| 98 | QVQLQESGGGSVQPGGSLKLSCAAS | 22 | GFTFNWYTMA | 116 | WYRQVPGEERKMVA | 49 | TITGASGDTKYADSVKG | 141 | RFTISRDNAKNTVTLQMNSLKPGDTAVYYCHA | 73 | YLTYDSGSVKGVNY | 148 | WGQGTQVTVSS |
| 98 | QVQLQESGGGSVQPGGSLKLSCAAS | 22 | GFTFNWYTMA | 116 | WYRQVPGEERKMVA | 49 | TITGASGDTKYADSVKG | 142 | RSTISRDNAKNTVTLQMNSLKPGDTAVYYCHA | 74 | CLTYDSGSVKGVNY | 148 | WGQGTQVTVSS |
| 99 | QVQLQESGGGFVQPGGSLKLSCAAS | 22 | GFTFNWYTMA | 116 | WYRQVPGEERKMVA | 49 | TITGASGDTKYADSVKG | 141 | RFTISRDNAKNTVTLQMNSLKPGDTAVYYCHA | 73 | YLTYDSGSVKGVNY | 148 | WGQGTQVTVSS |
| 96 | QVQLQESGGGFVQPGGSLKLSCAAS | 22 | GFTFNWYTMA | 116 | WYRQVPGEERKMVA | 49 | TITGASGDTKYADSVKG | 141 | RFTISRDNAKNTVTLQMNSLKPGDTAVYYCHA | 75 | YLTYDSGSAKGVNY | 148 | WGQGTQVTVSS |
| 100 | QVQLQESGGGLVQPGGSLGLSCAAS | 23 | GSLLNIYAMG | 117 | WYRQAPGRQRELVA | 50 | TVTSSGTAEYADSVKG | 143 | RFTISRDNAKNTVYLQMNSLRPEDTGVYYCNA | 76 | HLRYGDYVRGPPEYNY | 148 | WGQGTQVTVSS |
| 90 | QVQLQESGGGLVQPGGSLRLSCAAS | 24 | GGTLGYYAIG | 118 | WFRQAPGKEREAVS | 51 | CITSSDTSAYYADSAKG | 14 | RFTISRDNAKNTMYLQMNNLKPEDTAVYYCAA | 77 | GYYFRDYSDSYYYTGTGMKY | 147 | WGKGTQVTVSS |
| 101 | QVQLQESGGGLVQPGGSTRLSCAAS | 25 | GFTLDIYAIG | 119 | WFRQAPGKEHEGVS | 52 | WIVGNDGRTYYIDSVKG | 145 | RFTISRDNAKNTVYLEMNSLKPEDTAVYYCAA | 78 | KFWPRYYSGRPPVGRDGYDY | 148 | WGQGTQVTVSS |
| 102 | QVQLQESGGGLVQPGGSLILSCTIS | 26 | GASLRDRRVT | 120 | WSRQGPGKSLEIIA | 53 | VMAPDYGVHYFGSLEG | 146 | RVAVRGDVVKNTVYLQVNALKPEDTAIYWCSM | * | GNI | 153 | RGLGTQVTVSS |

*These sequences have fewer than the required minimum of four amino acids and are not assigned a SEQ ID NO.

TABLE 3

*Y. pestis* YseF SAb Protein Sequences

| SEQ ID NO | Name | Sequence |
|---|---|---|
| 154 | 3ysef57 | QVQLQESGGGLVQAGGSLRLSCAASGRTWRAYYMGWFRQAPGKEREFVAVMSRSGGTTSYADSVKGRFTISRDNAKNTVYLQMNNLAPEDTATYYCKAGGGMYGPDLYGMTYWGKGTQVTVSS |
| 155 | 3yscf124 | QVQLQESGGGLVQAGGSLRLSCVASGRAFSNYAMAWFRQAPGKEREFVAANWRSGGLTDYADSVKGRFTISRDDAKNTVYLQMNSLKPEDTAVYYCAAGGGSRWYGRTTASWYDYWGQGTQVTVSS |
| 156 | 3yscf15 | QVQLQESGGGLVQAGGSLRLSCAVSGRTFSRYAMGWFRQAPGKEREFVAAISWSGSSTYY-ADSVKGRFTISRDHAKNVMYLQMNGLKPEDTGVYVCARPAYGLRPPYNYRGQGTQVTVSS |
| 157 | 3yscf24 | QVQLQESGGGLVQAGGSLKLSCTASQRTFSRYSLGWFRQAPGEERVFVAATTWSGISSDY-ADSVKGRFTISRDNAKNTGYLQMNNLKPEDTGVYYCAAGRSSWFAPWLTPYEYDYWGRGTQVTVSS |

TABLE 3-continued

Y. pestis YseF SAb Protein Sequences

| SEQ ID NO | Name | Sequence |
|---|---|---|
| 158 | 3yscf142 | QVQLQESGGGLVQAGGSLRLSCAASGRTFSSHAMAWFRQGPGEERQFLAAIRWNGD-NIHYSDSAKG<br>RFTISRDLAKNTLYLQMNSLKPEDTAVYYCARGVYDYWGQGTQVTVSS |
| 159 | 3yscf75 | QVQLQESGGGLVQAGDSRILSCTASGRTFGRPFRYTMGWFRRAPGKEREFVGGITRSGN-NIYYSDS<br>VKGRFTISRDNAKNTVYLQMNSLKPEDTAVYYSNADWGWRNYWGQGTQVTVSS |
| 160 | 3yscf140 | QVQLQESGGGLVQAGGSLRLACAASGETVDDLAIGWFRQAPGKEREEISCISGSDGSTYY-ADSLSG<br>RFTISRDNVKNTVYLQMNSLKLEDTAVYYCYAEIYDRRWYRNDYWGQGTQVTVSS |

TABLE 4

Y. pestis YscF SAb DNA Sequences

| SEQ ID NO | Name | Sequence |
|---|---|---|
| 161 | 3yscf57 | CAGGTGCAGCTGCAGGAGTCTGGGGGAGGATTGGTGCAGGCTGGGGGCTCTCTGA-GACTCTCCTG<br>TGCAGCCTCTGGACGCACCTGGAGAGCCTATTACATGGGCTGGTTCCGCCAGGCTCCAGG-GAAGG<br>AGCGTGAGTTTGTAGCAGTTATGAGTCGGAGCGGTGGCACCACATCC-TATGCGGACTCCGTGAAG<br>GGCCGATTCACCATCTCCAGAGACAACGCCAAGAACACGGTGTATCTACAAAT-GAACAACCTGG<br>CACCTGAGGACACGGCCACGTATTATTGTAAGGCGGGGGGCG-GAATGTACGGGCCGGACCTGTA<br>TGGTATGACATACTGGGGCAAAGGGACCCAGGTCACCGTCTCCAGCGGCCGC-TACCCGTACGAC<br>GTTCCGGACTACGGTTCCGGCCGAGCATAG |
| 162 | 3yscf124 | CAGGTGCAGCTGCAGGAGTCTGGAGGAGGATTGGTACAGGCTGGGGGCTCTCTGA-GACTCTCCTG<br>TGTAGCCTCTGGACGCGCCTTCAGTAATTATGCGATGGCCTGGTTCCGCCAGGCTCCAGG-GAAGG<br>AGCGTGAGTTTGTAGCAGCTAATTGGCGGAGTGGTGGTCTTACAGACTATGCA-GACTCCGTGAAG<br>GGCCGATTCACCATCTCCAGAGACGACGCCAAGAACACGGTGTATCTGCAAAT-GAACAGCCTGA<br>AACCTGAGGACACGGCCGTTTAT-TACTGTGCCGCCGGGGCGGTAGTCGCTGGTACGGGCGAAC<br>AACCGCAAGTTGGTATGACTACTGGGGCCAGGGGACCCAGGT-CACCGTCTCCAGCGGCCGCTAC<br>CCGTACGACGTTCCGGACTACGGTTCCGGCCGAGCATAG |
| 163 | 3yscf15 | CAGGTGCAGCTGCAGGAGTCTGGGGGAGGATTGGTGCAGGCTGGGGGCTCTCTGA-GACTCTCCTG<br>TGCAGTCTCTGGACGCACCTTCAGTAGATATGCCATGGGCTGGTTCCGCCAGGCTCCAGG-GAAGG<br>AGCGTGAGTTTGTAGCAGCTATTAGCTGGAGTGGTAGTAGCACATATTATGCA-GACTCCGTGAAG<br>GGCCGATTCACCATCTCCAGAGACCACGCCAAGAACGTGATGTATCTGCAAAT-GAACGGCCTGA<br>AACCTGAGGACACGGGTGTTTATGTCTGTGCAA-GACCAGCGTACGGACTCCGCCCCCGTATAAT<br>TACCGGGGCCAGGGGACCCAGGTCACCGTCTCCAGCGGCCGC-TACCCGTACGACGTTCCGGACTA<br>CGGTTCCGGCCGAGCATAG |
| 164 | 3yscf24 | CAGGTGCAGCTGCAGGAGTCTGGGGGAGGATTGGTGCAGGCTGGGGGCTCTCT-GAAACTCTCCTG<br>CACAGCCTCTCAACGCACCTTCAGTCGC-TATAGCTTGGGCTGGTTCCGCCAGGCTCCAGGTGAGG<br>AGCGTGTTTTTGTAGCCGCTACTACATGGAGTGGTATAAGCAGTGACTATGCA-GACTCCGTGAAG<br>GGCCGATTCACCATCTCCAGAGACAACGCCAAGAACACGGGGTATCTGCAAATGAACAAT-TTAA<br>AACCTGAGGACACGGGCGTTTAT-TACTGTGCAGCAGGACGTAGTAGCTGGTTCGCCCCCTGGTTG<br>ACCCCCTATGAGTATGATTATTGGGGCCGGGGACCCAGGTCACCGTCTCCAGCGGCCGC-TACCC<br>GTACGACGTTCCGGACTACGGTTCCGGCCGAGCATAG |

TABLE 4-continued

Y. pestis YscF SAb DNA Sequences

| SEQ ID NO | Name | Sequence |
|---|---|---|
| 165 | 3yscf142 | CAGGTGCAGCTGCAGGAGTCTGGGGGAGGATTGGTGCAGGCTGGGGGCTCTCTGA-GACTCTCCTG<br>TGCAGCCTCTGGACGCACCTTCAGTAGCCATGCCATGGCCTGGTTCCGCCAGGGTCCAG-GAGAGG<br>AGCGTCAGTTTCTAGCAGCTATTAGATGGAATGGTGATAACATACACTATTCA-GACTCCGCGAAG<br>GGCCGATTCACCATCTCCAGAGACCTCGCCAAGAACACGCTCTATCTGCAAAT-GAACAGCCTGAA<br>ACCTGAGGACACGGCCGTGTATTACTGTGCAAGGGGGGTGTATGAC-TACTGGGGCCAGGGGACC<br>CAGGTCACCGTCTCCAGCGGCCGCTACCCGTACGACGTTCCGGAC-TACGGTTCCGGCCGAGCATA<br>G |
| 166 | 3yscf75 | CAGGTGCAGCTGCAGGAGTCTGGGGGAGGATTGGTGCAGGCTGGGGACTCTCGGA-TACTCTCCTG<br>TACAGCCTCTGGACGCACCTTTGGACGCCCCTTCAGATATAC-CATGGGCTGGTTCCGCCGGGCTC<br>CAGGGAAGGAGCGTGAGTTTGTAGGAGGTATTACAAGAAGTGGTAATAATATATACTAT-TCAGA<br>CTCCGTGAAGGGCCGATTCACCATCTCCAGAGACAACGCCAAGAACACGGTGTATCTC-CAAATG<br>AACAGCCTGAAACCTGAGGACACGGCCGTGTATTATTGTAACGCAGATTGGGGGTGGAG-GAACT<br>ACTGGGGCCAGGGGACCCAGGTCACCGTCTCCAGCGGCCGC-TACCCGTACGACGTTCCGGACTAC<br>GGTTCCGGCCGAGCATAG |
| 167 | 3yscf140 | CAGGTGCAGCTGCAGGAGTCTGGGGGAGGCTTGGTGCAGGCTGGGGGGTCTCTGA-GACTCGCCT<br>GTGCAGCCTCTGGAGAGACTGTCGATGATCTTGC-CATCGGCTGGTTCCGCCAGGCCCCAGGGAAG<br>GAGCGTGAGGAGATTTCATGTATTAGTGGTAGTGATGGTAGCACATACTATGCA-GACTCCCTGTC<br>GGGCCGATTCACCATCTCCAGGGACAACGTCAAGAACACGGTGTATCTGCAAAT-GAACAGCCTG<br>AAACTTGAGGACACGGCCGTCTATTACTGTTATGCAGAGATTTACGATA-GACGCTGGTATCGGAA<br>CGACTACTGGGGCCAGGGGACCCAGGTCACCGTCTCCAGCGGCCGC-TACCCGTACGACGTTCCGG<br>ACTACGGTTCCGGCCGAGCATAG |

TABLE 5

Y. pestis F1 SAb Protein Sequences

| SEQ ID NO | Name | Sequence |
|---|---|---|
| 168 | 3F55 | QVQLQESGGGLVQAGGSLRLSCAVSGMMYIREAIRWYRQAPGKQREWVAFVSSTGNPRYTDSVKG<br>RFTISRDNAKNTVYLQMNSLTPEDTAVYYCNTYLGSRDYWGQGTQVTVSS |
| 169 | 3F85 | QVQLQESGGGLVQPGGSLRLSCAVSGMMYIRYTMRWYRQAPGKQREWVAVVSSTGNPHYADSVK<br>GRFTISRDNAKNTVYLQMNSLTPEDTAVYYCNTYLGSRDYWGQGTQVTVSS |
| 170 | 3F44 | QVQLQESGGGLVRPGGSLRLSCAVSGRAVNRYHMHWYRQAPGKQREWVTFISVGGTTNYAGSVKG<br>RFTVSRDNAKNTLYLQMNSLKPEDTAVYYCNSAEYWGQGTQVTVSS |
| 171 | 4F34 | QVQLQESGGGSVQPGGSLSLSCSASGIIFSDYALTWYRQAPGKQREWVAQITRSQNINYTGSVKGRFT<br>VSRDNAKNTVHLQMNSLKPEDTAVYYCHAYDGRRPPYWGQGTQVTVSS |
| 172 | 4F6 | QVQLQESGGGSVQPGGSLSLSCSASGIIFSDYALTWYRQAPGKQREWVAQITRSQNINYTGSVKGRFT<br>VSRDNAKNTVHLQMNSLKPEDTAVYYCHAYDGRRRTYWGQGTQVTVSS |
| 173 | 4F1 | QVQLQESGGGLVQPGGSLSLSCSASGIIFSDYALTWYRQAPGKQREWVAQITRSQNINYTGSVKGRFT<br>VSRDNAKNTVHLQMNSLKPEDTAVYYCHAYDGRRPPYWGQGTQVTVSS |
| 174 | 3F31 | QVQLQESGGGLVQPGGSLSLSCSASGIIFSDYALTWYRQAPGKQREWVAQITRRQNINYTGSVKGRFT<br>VSRDNAKNTVHLQMNSLKPEDTAVYYCHAYDGRRSPYWGQGTQVTVSS |
| 175 | 3F61 | QVQLQESGGGLVQPGGSLRLSCSASGIIFSDYALTWYRQAPGKQREWVAQITRSQNINYTGSVGRFT<br>VSRDNAKNTVHLQMNSLKPEDAAVYYCHAYDGRRPPYWGQGTQVTVSS |
| 176 | 4F27 | QVQLQESGGGLVQPGGSLRLSCAASARIFSIYAMVWYRQAPGKQREWVAAITTGGTTNYADSVKGR<br>FTISRDNAKNTVYLQMNSLKPEDTAVYYCNAPGYWGQGTQVTVSS |

TABLE 5-continued

Y. pestis F1 SAb Protein Sequences

| SEQ ID NO | Name | Sequence |
|---|---|---|
| 177 | 3F26 | QVQLQESGGGLVQPGGSLRLSCAASGVIASISVLRWYRQTPGKTRDWVAIITSGGNTRYADSVKGRF<br>TTSRDNARNTVYLQMNSLKPEDTAVYYCNTLVGAKDYWGQGTQVTVSS |
| 178 | 4F59 | QVQLQESGGGLVRPGGSLRLSCEASGTTFRSLVMKWYRQAPGKEREWVAFISSGDRTRYTEAVKG<br>RFTISRDNAKNALYLQMNGLKPEDTAVYYCNANGIYWGKGTQVTVSS |
| 179 | 3F5 | QVQLQESGGGLVQSGDSLRLSCAASGFTFSNYAMSWVRQAPGKGLEWVSTINSGGGSTSYAYSVKG<br>RFTISRDNAKNLYLQMNSLKPEDTAVYYCAKTASHIPLSQGTQVTVSS |
| 180 | 4F57 | QVQLQESGGGLVQPGGSLRLSCAASGFTFSNYAMSWVRQAPGKGLEWVSTINIGGGSTSYADSVKG<br>RFTISRDNAKNTLYLQMNSLKPEDTAVYYCAKTASHIPLSQGTQVTVSS |
| 181 | 4F75 | QVQLQESGGGLVQPGGSLRLSCAASGFTFRNYAMSWVRQAPGKGLEWVSTINGGGGITSYADSVKG<br>RFTISRDNAKNTMYLQMNSLKPEDTAVYYCAQTARDSRDSRGQGTQVTVSS |
| 182 | 3F59 | QVQLQESGGGLVQPGGSLRLSCAASGFTFSSYAMSWVRLAPGKGLEWVSTINIAGGITSYADSVKGR<br>FTISRDNAKNTLYLQMNSLKPEDTAVYYCAKTAANWSAQRGQGTQVTVSS |
| 183 | 4F78 | QVQLQESGGGLVQPGGSLRLSCAASGFTFSSYAMSWVRQAPGKGLEWVSTINMGGGTTSYADSVKG<br>RFTISRHNAKNTLYLQMNSLKPEDTAVYYCAKTAGNWSAQRGQGTQVTVSS |
| 184 | 3F1 | QVQLQESGGGLVQPGGSLRLSCAASGFTFSTSAMSWIRQPPGKAREVVATITSAGGSISYVNSVKGRF<br>TISRDNAKNTLYLQMNMLKPEDTAVYYCARLVNLAQTGQGTQVTVSS |
| 185 | 3F65 | QVQLQESGGGLVQPGGSLRLSCAASGFTFSTNAMSWIRQPPGKAREVVATITSAGGISYVNSVKGRF<br>TISRDNAKNTLYLQMNMLKPEDTAVYYCARLVNLAQTGQGTQVTVSS |

TABLE 6

Y. pestis F1 SAb DNA Sequences

| SEQ ID NO | Name | Sequence |
|---|---|---|
| 186 | 3F55 | CAGGTGCAGCTGCAGGAGTCTGGGGGAGGCTTGGTGCAGGCTGGGGGCTCTCTGAGACTCTCCT<br>GTGCAGTTTCTGGAATGATGTACATTAGGGAGGCTATACGCTGGTACCGCCAGGCTCCAGGGAA<br>GCAGCGCGAGTGGGTCGCCTTTGTAAGTAGTACTGGTAATCCACGCTATACAGACTCCGTGAAGG<br>GCCGATTCACCATCTCCAGAGACAACGCCAAGAACACGGTGTATCTGCAAATGAACAGCCTGAC<br>ACCTGAGGACACGGCCGTCTATTACTGTAATACATACTTGGGCTCGAGGGACTACTGGGGCCAGG<br>GGACCCAGGTCACCGTCTCCAGCGGCCGCTACCCGTACGACGTTCCGGACTACGGTTCCGGCCGA<br>GCATAG |
| 187 | 3F85 | CAGGTGCAGCTGCAGGAGTCTGGAGGAGGCTTGGTGCAGCCTGGGGGGTCTCTGAGACTCTCCT<br>GTGCAGTTTCTGGAATGATGTACATTAGGTACACTATGCGCTGGTACCGCCAGGCTCCAGGGAAG<br>CAGCGCGAGTGGGTCGCCGTTGTAAGTAGTACTGGTAATCCACACTATGCAGACTCCGTGAAGG<br>GCCGATTCACCATCTCCAGAGACAACGCCAAGAACACGGTGTATCTGCAAATGAACAGCCTGAC<br>ACCTGAGGACACGGCCGTCTATTACTGTAATACATACTTGGGCTCGAGGGACTACTGGGGCCAGG<br>GGACCCAGGTCACCGTCTCCAGCGGCCGCTACCCGTACGACGTTCCGGACTACGGTTCCGGCCGA<br>GCATAG |
| 188 | 3F44 | CAGGTGCAGCTGCAGGAGTCTGGGGGAGGCTTGGTGCGGCCTGGGGGGTCTCTGAGACTCTCCT<br>GTGCAGTCTCTGGAAGAGCCGTCAATAGGTATCACATGCACTGGTACCGCCAGGCTCCAGGGAA<br>GCAGCGCGAGTGGGTCACATTTATTAGTGTTGGTGGTACCACAAACTATGCAGGCTCCGTGAAGG<br>GCCGATTCACCCGTCTCCCGAGACAACGCCAAAAACACGCTGTATCTGCAAATGAACAGCCTGAA<br>ACCTGAGGACACGGCCGTCTATTACTGTAATTCAGCTGAATACTGGGGCCAGGGGACCCAGGTC<br>ACCGTCTCCAGCGGCCGCTACCCGTACGACGTTCCGGACTACGGTTCCGGCCGAGCATAG |
| 189 | 4F34 | CAGGTGCAGCTGCAGGAGTCTGGGGGAGGCTCGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGTCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGCCCACCCTACTGGGGCC<br>AGGGGACCCAGGTCACCGTCTCCAGCGGCCGCTACCCGTACGACGTTCCGGACTACGGTTCCGGC<br>CGAGCATAG |
| 190 | 4F6 | CAGGTGCAGCTGCAGGAGTCTGGGGGAGGCTCGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGTCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGCCGAACCTACTGGGGCC<br>AGGGGACCCAGGTCACCGTCTCCAGCGGCCGCTACCCGTACGACGTTCCGGACTACGGTTCCGGC<br>CGAGCATAG |

TABLE 6-continued

Y. pestis F1 SAb DNA Sequences

| SEQ ID NO | Name | Sequence |
|---|---|---|
| 191 | 4F1 | CAGGTGCAGCTGCAGGAGTCTGGGGGAGGCTTGGTGCAGCCTGGGGGGTCTCTGAGCCTCTCCTG<br>TTCAGCCTCTGGAATCATCTTCAGTGACTATGCCCTGACCTGGTACCGCCAGGCTCCAGGGAAGC<br>AGCGCGAGTGGGTTGCACAGATTACGCGAAGCAAAATATAAATTATACAGGATCCGTGAAGGG<br>CCGATTCACCGTCTCCAGAGACAACGCCAAGAACACAGTGCATCTGCAAATGAACAGCCTGAAA<br>CCTGAGGACACGGCCGTCTACTATTGTCATGCATATGACGGTCGACGCCCACCCTACTGGGGCCA<br>GGGGACCCAGGTCACCGTCTCCAGCGGCCGCTACCCGTACGACGTTCCGGACTACGGTTCCGGCC<br>GAGCATAG |
| 192 | 3F31 | CAGGTGCAGCTGCAGGAGTCTGGGGGAGGCTTGGTGCAGCCTGGGGGGTCTCTGAGCCTCTCCTG<br>TTCAGCCTCTGGAATCATCTTCAGTGACTATGCCCTGACCTGGTACCGCCAGGCTCCAGGGAAGC<br>AGCGCGAGTGGGTTGCACAGATTACGCGAAGGCAAAATATAAATTATACAGGATCCGTGAAGGG<br>CCGATTCACCGTCTCCAGAGACAACGCCAAGAACACAGTGCATCTGCAAATGAACAGCCTGAAA<br>CCTGAGGACACGGCCGTCTACTATTGTCATGCATATGACGGTCGACGATCACCCTACTGGGGCCA<br>GGGGACCCAGGTCACCGTCTCCAGCGGCCGCTACCCGTACGACGTTCCGGACTACGGTTCCGGCC<br>GAGCATAG |
| 193 | 3F61 | CAGGTGCAGCTGCAGGAGTCTGGGGGAGGCTTGGTGCAGCCTGGGGGGTCTCTGAGACTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGTCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACGCGGCCGTCTACTATTGTCATGCATATGACGGTCGACGCCCACCCTACTGGGGCC<br>AGGGGACCCAGGTCACCGTCTCCAGCGGCCGCTACCCGTACGACGTTCCGGACTACGGTTCCGGC<br>CGAGCATAG |
| 194 | 4F27 | CAGGTGCAGCTGCAGGAGTCTGGGGGAGGCTTGGTGCAGCCTGGGGGGTCTCTGAGACTCTCCT<br>GTGCAGCCTCTGCCCGCATCTTCAGTATCTATGCCATGGTATGGTACCGCCAGGCTCCAGGGAAG<br>CAGCGCGAGTGGGTCGCAGCTATTACTACTGGTGGTACCACAAACTATGCAGACTCCGTGAAGG<br>GCCGATTCACCATCTCCAGAGACAACGCCAAGAACACGGTGTATCTGCAAATGAACAGCCTGAA<br>ACCTGAGGACACGGCCGTCTATTACTGTAATGCTCCGGGCTACTGGGGCCAGGGGACCCAGGTC<br>ACCGTCTCCAGCGGCCGCTACCCGTACGACGTTCCGGACTACGGTTCCGGCCGAGCATAG |
| 195 | 3F26 | CAGGTGCAGCTGCAGGAGTCTGGGGGAGGCTTGGTGCAGCCTGGGGGGTCTCTGAGACTCTCCT<br>GTGCAGCCTCTGGAGTCATCGCCAGTATCTCCGTCCTGCGCTGGTACCGCCAAACACCAGGAAAG<br>ACGCGCGACTGGGTCGCAATTATTACTAGTGGTGGCAACACACGCTATGCAGACTCCGTGAAGG<br>GCCGATTCACCACCTCCAGAGATAACGCCAGGAACACGGTGTATCTGCAAATGAACAGCCTGAA<br>ACCTGAGGACACGGCCGTCTATTACTGTAATACACTTGTAGGAGCCAAGGACTACTGGGGCCAG<br>GGGACCCAGGTCACCGTCTCCAGCGGCCGCTACCCGTACGACGTTCCGGACTACGGTTCCGGCCG<br>AGCATAG |
| 196 | 4F59 | CAGGTGCAGCTGCAGGAGTCTGGGGGAGGCTTGGTGCGGCCTGGGGGATCTCTAAGACTCTCCT<br>GTGAAGCCTCTGGAACCACCTTCAGAAGCCTCGTAATGAAATGGTACCGCCAGGCTCCAGGGAA<br>GGAGCGCGAGTGGGTCGCATTTATTTCTAGTCCTGGTGATCGCACTCGCTACACAGAAGCCGTGA<br>AGGGCCGATTCACCATCTCCAGAGACAATGCCAAGAACGCGCTGTATCTGCAAATGAACGGCCT<br>GAAACCTGAGGACACGGCCGTGTATTATTGTAACGCGAACGGAATATACTGGGGCAAAGGGACC<br>CAGGTCACCGTCTCCAGCGGCCGCTACCCGTACGACGTTCCGGACTACGGTTCCGGCCGAGCATA<br>G |
| 197 | 3F5 | CAGGTGCAGCTGCAGGAGTCTGGGGGAGGCTTGGTGCAATCTGGGGATTCTCTGAGACTCTCCTG<br>TGCAGCCTCTGGATTCACCTTCAGTAACTATGCTATGAGCTGGGTCCGCCAGGCTCCAGGAAAGG<br>GGCTCGAGTGGGTCTCAACTATTAATAGTGGTGGTGGTAGCACAAGCTATGCGTACTCCGTGAAG<br>GGCCGATTCACCATCTCCAGAGACAACGCCAAGAACACGCTGTATCTGCAAATGAACAGCCTGA<br>AACCTGAGGACACGGCCGTGTATTACTGTGCAAAGACGGCCTCTCACATACCCTTGAGCCAGGG<br>GACCCAGGTCACCGTCTCCAGCGGCCGCTACCCGTACGACGTTCCGGACTACGGTTCCGGCCGAG<br>CATAG |
| 198 | 4F57 | CAGGTGCAGCTGCAGGAGTCTGGGGGAGGCTTGGTGCAACCTGGGGGTTCTCTGAGACTCTCCTG<br>TGCAGCCTCTGGATTCACCTTCAGTAACTATGCTATGAGCTGGGTCCGCCAGGCTCCAGGAAAGG<br>GGCTCGAGTGGGTCTCAACTATTAATATTGGTGGTGGTAGCACAAGCTATGCAGACTCCGTGAAG<br>GGCCGATTCACCATCTCCAGAGACAACGCCAAGAACACGCTGTATCTGCAAATGAACAGCCTGA<br>AACCTGAGGACACGGCCGTGTATTACTGTGCAAAGACGGCCTCTCACATACCCTTGAGCCAGGG<br>GACCCAGGTCACCGTCTCCAGCGGCCGCTACCCGTACGACGTTCCGGACTACGGTTCCGGCCGAG<br>CATAG |
| 199 | 4F75 | CAGGTGCAGCTGCAGGAGTCTGGGGGAGGCTTGGTGCAACCTGGGGGTTCTCTGAGACTCTCCTG<br>TGCAGCCTCTGGATTCACCTTCAGGAACTATGCAATGAGCTGGGTCCGTCAGGCTCCAGGAAAGG<br>GGCTCGAGTGGGTCTCAACTATTAATGGTGGTGGTGGTATCACAAGCTATGCAGACTCCGTGAAG<br>GGCCGATTCACCATCTCCAGAGACAACGCCAAGAACACAATGTATCTGCAAATGAACAGCCTGA<br>AACCTGAGGACACGGCCGTCTATTACTGTGCCCAAACCGCCCGCGATTCCCGCGATTCCCGGGGC<br>CAGGGGACCCAGGTCACCGTCTCCAGCGGCCGCTACCCGTACGACGTTCCGGACTACGGTTCCGG<br>CCGAGCATAG |

TABLE 6-continued

Y. pestis F1 SAb DNA Sequences

| SEQ ID NO | Name | Sequence |
|---|---|---|
| 200 | 3F59 | CAGGTGCAGCTGCAGGAGTCTGGGGGAGGCTTGGTGCAACCTGGGGGTTCTCTGAGACTCTCCTG<br>TGCAGCCTCTGGATTCACCTTCAGTAGCTATGCTATGAGCTGGGTCCGCCTGGCTCCAGGAAAGG<br>GGCTCGAGTGGGTCTCAACTATTAATATCGCTGGTGGTATCACAAGCTATGCAGACTCCGTGAAG<br>GGCCGATTCACCATCTCCAGAGACAACGCCAAGAACACGCTGTATCTGCAAATGAACAGCCTGA<br>AACCTGAGGACACGGCCGTGTATTACTGTGCAAAAACGGCGGCCAACTGGAGCGCCCAGAGAGG<br>CCAGGGGACCCAGGTCACCGTCTCCAGCGGCCGCTACCCGTACGACGTTCCGGACTACGGTTCCG<br>GCCGAGCATAG |
| 201 | 4F78 | CAGGTGCAGCTGCAGGAGTCTGGGGGAGGCTTGGTGCAACCTGGGGGTTCTCTGAGACTCTCCTG<br>TGCAGCCTCTGGATTCACCTTCAGTAGCTATGCTATGAGCTGGGTCCGCCAGGCTCCAGGAAAGG<br>GGCTCGAGTGGGTCTCAACTATTAATATGGGTGGTGGTACCACAAGCTATGCAGACTCCGTGAAG<br>GGCCGATTCACCATCTCCAGACACAACGCCAAGAACACGCTGTATCTGCAAATGAACAGCCTGA<br>AACCTGAGGACACGGCCGTGTATTACTGTGCAAAAACGGCGGGCAACTGGAGCGCCCAGAGAGG<br>CCAGGGGACCCAGGTCACCGTCTCCAGCGGCCGCTACCCGTACGACGTTCCGGACTACGGTTCCG<br>GCCGAGCATAG |
| 202 | 3F1 | CAGGTGCAGCTGCAGGAGTCTGGGGGAGGCTTGGTGCAACCTGGGGGTTCTCTGAGACTGTCCTG<br>TGCAGCCTCTGGATTCACCTTCAGTACAAGTGCCATGAGTTGGATCCGCCAGCCTCCAGGGAAGG<br>CGCGCGAGGTGGTCGCAACTATTACTAGTGCTGGTGGTAGTATAAGTTATGTAAACTCCGTGAAG<br>GGCCGATTCACCATCTCCAGAGACAACGCCAAGAACACGCTGTATCTGCAAATGAACATGCTGA<br>AACCTGAGGACACGGCCGTGTATTACTGTGCCCGACTGGTCAACCTTGCCCAGACCGGCCAGGG<br>AACCCAGGTCACCGTCTCCAGCGGCCGCTACCCGTACGACGTTCCGGACTACGGTTCCGGCCGAG<br>CATAG |
| 203 | 3F65 | CAGGTGCAGCTGCAGGAGTCTGGGGGAGGCCTGGTGCAACCTGGGGGTTCTCTGAGACTGTCCT<br>GTGCAGCCTCTGGATTCACCTTCAGTACAAATGCCATGAGTTGGATCCGCCAGCCTCCAGGGAAG<br>GCGCGCGAGGTGGTCGCAACTATTACTAGTGCTGGTGGTGGTAGTATAAGTTATGTAAACTCCGTGAA<br>GGGCCGATTCACCATCTCCAGAGACAACGCCAAGAACACGCTGTATCTGCAAATGAACATGCTG<br>AAACCTGAGGACACGGCCGTGTATTACTGTGCCCGACTGGTCAACCTTGCCCAGACCGGCCAGG<br>GAACCCAGGTCACCGTCTCCAGCGGCCGCTACCCGTACGACGTTCCGGACTACGGTTCCGGCCGA<br>GCATAG |

TABLE 7

Y. pestis LcrV SAb Protein Sequences

| SEQ ID NO | Name | Sequence |
|---|---|---|
| 204 | 1LCRV32 | QVQLQESGGGMVEPGGSLRLSCAASGFRFSSYAMSWVRQAPGKGLERVSAINSDGDKTSYADSVK<br>GRFTISRDNARNTLYLQMSNLKPEDTAVYYCADRDLYCSGSMCKDVLGGARYDFRGQGTQVTVSS |
| 205 | 2LCRV4 | QVQLQESGGGLVEPGGSLRLSCAASGFRFSSYAMSWVRQAPGKGLERVSAINSDGDKTSYADSVKG<br>RFTISRDNARNTLYLQMSNLKPEDTAVYYCADRDLYCSGSMCKDVLGGARYDFRGQGTQVTVSS |
| 206 | 2LCRV3 | QVQLQESGGGMVEPGGSLRLSCAASGFRFSSYAMSWVRQAPGKGLERVSAINSDGDKTSYADSVK<br>GRFTISRDNARNTLYLQMNNLKPEDTAVYYCADRDLYCSGSMCKDVLGGARYDFRGQGTQVTVSS |
| 207 | 1LCRV52 | QVQLQESGGGLVQSGESLRLSCAASGLRFSSYAMSWVRQAPGKGLERVSAINSDGDKTSYADSVKG<br>RFTISRDNARNTLYLQMSNLKPEDTAVYYCADRDLYCSGSMCKDVLGGARYDFRGQGTQVTVSS |
| 208 | 1LCRV4 | QVQLQESGGGLVQPGGSLKLSCAASGFTFNWYTMAWYRQVPGEERKMVATITGASGDTKYADSV<br>KGRFTISRDNAKNTVTLQMNSLKPGDAAVYYCHAYLTYDSGSVKGVNYWGQGIQVTVSS |
| 209 | 2LCRV13 | QVQLQESGGGLVRPGGSLKLSCAASGFTFNWYTMAWYRQVPGEERKMVATITGASGDTKYADSV<br>KGRFTISRDNAKNTVTLQMNSLKPGDTAVYYCHAYLTYDSGSVKGVNYWGQGTQVTVSS |
| 210 | 2LCRV1 | QVQLQESGGGSVQPGGSLKLSCAASGFTFNWYTMAWYRQVPGEERKMVATITGASGDTKYADSV<br>KGRFTISRDNAKNTVTLQMNSLKPGDTAVYYCHAYLTYDSGSVKGVNYWGQGTQVTVSS |
| 211 | 1LCRV81 | QVQLQESGGGSVQPGGSLKLSCAASGFTFNWYTMAWYRQVPGEERKMVATITGASGDTKYADSV<br>KGRSTISRDNAKNTVTLQMNSLKPGDTAVYYCHACLTYDSGSVKGVNYWGQGTQVTVSS |

TABLE 7-continued

Y. pestis LcrV SAb Protein Sequences

| SEQ ID NO | Name | Sequence |
|---|---|---|
| 212 | 1LCRV27 | QVQLQESGGGFVQPGGSLKLSCAASGFTFNWYTMAWYRQVPGEERKMVATITGASGDTKYADSV KGRFTISRDNAKNTVTLQMNSLKPGDTAVYYCHAYLTYDSGSVKGVNYWGQGIQVTVSS |
| 213 | 1LCRV34 | QVQLQESGGGLVQPGGSLKLSCAASGFTFNWYTMAWYRQVPGEERKMVATITGASGDTKYADSV KGRFTISRDNAKNTVTLQMNSLKPGDTAVYYCHAYLTYDSGSAKGVNYWGQGTQVTVSS |
| 214 | 1LCRV31 | QVQLQESGGGLVQPGGSLGLSCAASGSLLNIYAMGWYRQAPGRQRELVATVTSSGTAEYADSVKG RFTISRDNAKNTVYLQMNSLRPEDTGVYYCNAHLRYGDYVRGPPEYNYWGQGTQVTVSS |
| 215 | 1LCRV28 | QVQLQESGGGLVQPGGSLRLSCAASGGTLGYYAIGWFRQAPGKEREAVSCITSSDTSAYYADSAKG RFTISRDNAKNTMYLQMNNLKPEDTAVYYCAAGYYFRDYSDSYYYTGTGMKVWGKGTQVTVSS |
| 216 | 2LCRV11 | QVQLQESGGGLVQPGGSTRLSCAASGFTLDIYAIGWFRQAPGKEHEGVSWIVGNDGRTYYIDSVKG RFTISRDNAKNTVYLEMNSLKPEDTAVYYCAAKFWPRYYSGRPPVGRDGYDYWGQGTQVTVSS |
| 217 | 1LCRV47 | QVQLQESGGGLVQPGGSLILSCTISGASLRDRRVTWSRQGPGKSLEIIAVMAPDYGVHYFGSLEGRV AVRGDVVKNTVYLQVNALKPEDTAIYWCSMGNIRGLGTQVTVSS |

TABLE 8

Y. pestis LcrV SAb DNA Sequences

| SEQ ID NO | Name | Sequence |
|---|---|---|
| 218 | 1LCRV32 | CAGGTGCAGCTGCAGGAGTCTGGGGGAGGCATGGTAGAACCTGGGGGTTCTCTGAGACTCTCCT GTGCAGCCTCTGGATTCCGCTTCAGTAGTTATGCTATGAGTTGGGTCCGCCAGGCTCCAGGAAA GGGGCTCGAGCGGGTCTCGGCTATTAATAGTGATGGTGATAAAACAAGCTATGCAGACTCCGTG AAGGGCCGATTTACCATCTCCAGAGACAACGCCAGGAACACGCTGTATCTGCAAATGAGCAAC CTGAAACCTGAAGACACGGCCGTGTATTACTGTGCAGACCGAGATTTGTACTGTTCAGGCTCTA TGTGTAAGGACGTCTTGGGGGGAGCACGCTATGACTTTCGGGGCCAGGGGACCCAGGTCACCGT CTCCAGCGGCCGCTACCCGTACGACGTTCCGGACTACGGTTCCGGCCGAGCATAG |
| 219 | 2LCRV4 | CAGGTGCAGCTGCAGGAGTCTGGAGGAGGCTTGGTAGAACCTGGGGGTTCTCTGAGACTCTCCT GTGCAGCCTCTGGATTCCGCTTCAGTAGTTATGCTATGAGTTGGGTCCGCCAGGCTCCAGGAAA GGGGCTCGAGCGGGTCTCAGCTATTAATAGTGATGGTGATAAAACAAGCTATGCAGACTCCGTG AAGGGCCGATTTACCATCTCCAGAGACAACGCCAGGAACACGCTGTATCTGCAAATGAGCAAC CTGAAACCTGAAGACACGGCCGTGTATTACTGTGCAGACCGAGATTTGTACTGTTCAGGCTCTA TGTGTAAGGACGTCTTGGGGGGAGCACGCTATGACTTTCGGGGCCAGGGGACCCAGGTCACCGT CTCCAGCGGCCGCTACCCGTACGACGTTCCGGACTACGGTTCCGGCCGAGCATAG |
| 220 | 2LCRV3 | CAGGTGCAGCTGCAGGAGTCTGGGGGAGGCATGGTAGAACCTGGGGGTTCTCTGAGACTCTCTT GTGCAGCCTCTGGATTCCGCTTCAGTAGTTATGCTATGAGTTGGGTCCGCCAGGCTCCAGGAAA GGGGCTCGAGCGGGTCTCGGCTATTAATAGTGATGGTGATAAAACAAGCTATGCAGACTCCGTG AAGGGCCGATTCACCATCTCCAGAGACAACGCCAGGAACACGCTGTATCTGCAAATGAACAAC CTGAAACCTGAAGACACGGCCGTGTATTACTGTGCAGACCGAGATTTGTACTG TTCGGGCTCTATGTGTAAGGACGTCTTGGGGGGAGCACGCTATGACTTTCGGGGCCAGGGGACC CAGGTCACCGTCTCCAGCGGCCGCTACCCGTACGACGTTCCGGACTACGGTTCCGGCCGAGCAT AG |

TABLE 8-continued

Y. pestis LcrV SAb DNA Sequences

| SEQ ID NO | Name | Sequence |
|---|---|---|
| 221 | 1LCRV52 | CAGGTGCAGCTGCAGGAGTCTGGGGGAGGCTTGGTGCAGTCTGGCGAGTCTCTCAGACTCTCCT GTGCAGCCTCTGGACTCCGCTTCAGTAGTTATGCTATGAGTTGGGTCCGCCAGGCTCCAGGAAA GGGGCTCGAGCGGGTCTCGGCTATTAATAGTGATGGTGATAAAACAAGCTATGCAGACTCCGTG AAGGGCCGATTTACCATCTCCAGAGACAACGCCAGGAACACGCTGTATCTGCAAATGAGCAAC CTGAAACCTGAAGACACGGCCGTGTATTACTGTGCAGACCGAGATTTGTACTGTTCAGGCTCTA TGTGTAAGGACGTCTTGGGGGGAGCACGCTATGACTTTCGGGGCCAGGGGACCCAGGTCACCGT CTCCAGCGGCCGCTACCCGTACGACGTTCCGGACTACGGTTCCGGCCGAGCATAG |
| 222 | 1LCRV4 | CAGGTGCAGCTGCAGGAGTCTGGAGGAGGCCTGGTGCAGCCTGGGGGGTCTCTGAAACTCTCCT GTGCAGCCTCTGGATTCACCTTCAATTGGTATACCATGGCCTGGTATCGCCAGGTTCCAGGGGA GGAGCGCAAAATGGTCGCCACAATTACAGGTGCTAGTGGTGACACAAAATATGCAGACTCCGT GAAGGGCCGGTTCACCATCTCCAGAGACAATGCCAAGAACACGGTGACACTGCAAATGAACAG CCTTAAACCTGGAGACGCGGCCGTCTATTACTGTCATGCCTACCTAACCTACGACTCGGGGTCC GTCAAAGGAGTTAACTACTGGGGCCAGGGGACCCAGGTCACCGTCTCCAGCGGCCGCTACCCGT ACGACGTTCCGGACTACGGTTCCGGCCGAGCATAG |
| 223 | 1LCRV13 | CAGGTGCAGCTGCAGGAGTCTGGGGGAGGCTTGGTGCGGCCTGGGGGGTCTCTGAAACTCTCCT GTGCAGCCTCTGGATTCACCTTCAATTGGTATACCATGGCCTGGTATCGCCAGGTTCCAGGGGA GGAGCGCAAAATGGTCGCCACAATTACAGGTGCTAGTGGTGACACAAAATATGCAGACTCCGT GAAGGGCCGGTTCACCATCTCCAGAGACAATGCCAAGAACACGGTGACACTGCAAATGAACAG CCTTAAACCTGGAGACACGGCCGTCTATTACTGTCATGCCTACCTAACCTACGACTCGGGGTCC GTCAAAGGAGTTAACTACTGGGCCAGGGGACCCAGGTCACCGTCTCCAGCGGCCGCTACCCGT ACGACGTTCCGGACTACGGTTCCGGCCGAGCATAG |
| 224 | 2LCRV1 | CAGGTGCAGCTGCAGGAGTCTGGGGGAGGCTCGGTGCAGCCTGGGGGGTCTCTGAAACTCTCCT GTGCAGCCTCTGGATTCACCTTCAATTGGTATACCATGGCCTGGTATCGCCAGGTTCCAGGGGA GGAGCGCAAAATGGTTGCCACAATTACAGGTGCTAGTGGTGACACAAAATATGCAGACTCCGT GAAGGGCCGGTTCACCATCTCCAGAGACAATGCCAAGAACACGGTGACACTGCAAATGAACAG CCTTAAACCTGGAGACACGGCCGTCTATTACTGTCATGCCTACCTAACCTACGACTCGGGGTCC GTCAAAGGAGTTAACTACTGGGCCAGGGGACCCAGGTCACCGTCTCCAGCGGCCGCTACCCGT ACGACGTTCCGGACTACGGTTCCGGCCGAGCATAG |
| 225 | 1LCRV81 | CAGGTGCAGCTGCAGGAGTCTGGGGGAGGCTCGGTGCAGCCTGGGGGTCTCTGAAACTCTCCT GTGCAGCCTCTGGATTCACCTTCAATTGGTATACCATGGCCTGGTATCGCCAGGTTCCAGGGGA GGAGCGCAAAATGGTCGCCACAATTACAGGTGCTAGTGGTGACACAAAATATGCAGACTCCGT GAAGGGCCGGTCCACCATCTCCAGAGACAATGCCAAGAACACGGTGACACTGCAAATGAACAG CCTTAAACCTGGAGACACGGCCGTCTATTACTGTCATGCCTGCCTAACCTACGACTCGGGGTCC GTCAAAGGAGTTAACTACTGGGGTCAGGGGACCCAGGTCACCGTCTCCAGCGGCCGCTACCCGT ACGACGTTCCGGACTACGGTTCCGGCCGAGCATAG |
| 226 | 1LCRV27 | CAGGTGCAGCTGCAGGAGTCTGGGGGAGGCTTCGTGCAGCCTGGGGGGTCTCTGAAACTCTCCT GTGCAGCCTCTGGATTCACCTTCAATTGGTATACCATGGCCTGGTATCGCCAGGTTCCAGGGGA GGAGCGCAAAATGGTCGCCACAATTACAGGTGCTAGTGGTGACACAAAATATGCAGACTCCGT |

TABLE 8-continued

*Y. pestis* LcrV SAb DNA Sequences

| SEQ ID NO | Name | Sequence |
|---|---|---|
| | | GAAGGGCCGGTTCACCATCTCCAGAGACAATGCCAAGAACACGGTGACACTGCAAATGAACAG |
| | | CCTTAAACCTGGAGACACGGCCGTCTATTACTGTCATGCCTACCTAACCTACGACTCGGGGTCC |
| | | GTCAAAGGAGTTAACTACTGGGGCCAGGGGACCCAGGTCACCGTCTCCAGCGGCCGCTACCCGT |
| | | ACGACGTTCCGGACTACGGTTCCGGCCGAGCATAG |
| 227 | 1LCRV34 | CAGGTGCAGCTGCAGGAGTCTGGGGGAGGCCTGGTGCAGCCTGGGGGGTCTCTGAAACTCTCCT |
| | | GTGCAGCCTCTGGATTCACCTTCAATTGGTATACCATGGCCTGGTATCGCCAGGTTCCAGGGGA |
| | | GGAGCGCAAAATGGTCGCCACAATTACAGGTGCTAGTGGTGACACAAAATATGCAGACTCCGT |
| | | GAAGGGCCGGTTCACCATCTCCAGAGACAATGCCAAGAACACGGTGACACTGCAAATGAACAG |
| | | CCTTAAACCTGGAGACACGGCCGTCTATTACTGTCATGCCTACCTAACCTACGACTCGGGGTCC |
| | | GCCAAAGGAGTTAACTACTGGGGCCAGGGGACCCAGGTCACCGTCTCCAGCGGCCGCTACCCG |
| | | TACGACGTTCCGGACTACGGTTCCGGCCGAGCATAG |
| 228 | 1LCRV31 | CAGGTGCAGCTGCAGGAGTCTGGGGGAGGCTTGGTGCAGCCTGGGGGGTCTCTAGGACTCTCCT |
| | | GTGCAGCCTCTGGAAGCCTCTTAAATATCTATGCCATGGGCTGGTACCGCCAGGCTCCAGGGAG |
| | | ACAGCGCGAGTTGGTCGCAACTGTAACGAGTAGTGGAACCGCAGAATATGCAGACTCCGTGAA |
| | | GGGCCGATTCACCATCTCTAGAGACAACGCCAAGAACACGGTGTATCTGCAAATGAACAGCCT |
| | | GAGACCTGAGGACACGGGCGTCTATTACTGTAATGCACATCTCAGATATGGCGACTATGTCCGT |
| | | GGCCCTCCGGAGTATAACTACTGGGGCCAGGGGACCCAGGTCACCGTCTCCAGCGGCCGCTACC |
| | | CGTACGACGTTCCGGACTACGGTTCCGGCCGAGCATAG |
| 229 | 1LCRV28 | CAGGTGCAGCTGCAGGAGTCTGGGGGAGGCTTGGTGCAGCCTGGGGGGTCTCTGAGACTCTCCT |
| | | GTGCAGCCTCTGGAGGCACTTTGGGTTACTATGCCATAGGCTGGTTCCGCCAGGCCCCAGGGAA |
| | | GGAGCGCGAGGCGGTCTCCTGTATTACTAGTAGTGACACTAGCGCATACTATGCAGACTCCGCG |
| | | AAGGGCCGATTCACCATCTCCAGAGACAACGCCAAGAACACGATGTATCTGCAAATGAACAAC |
| | | CTGAAACCTGAGGACACAGCCGTTTATTACTGTGCAGCCGGTTACTATTTTAGAGACTATAGTG |
| | | ACAGTTACTACTACACGGGGACGGGTATGAAAGTCTGGGGCAAAGGGACCCAGGTCACCGTCT |
| | | CCAGCGGCCGCTACCCGTACGACGTTCCGGACTACGGTTCCGGCCGAGCATAG |
| 230 | 2LCRV11 | CAGGTGCAGCTGCAGGAGTCTGGGGGAGGCTTGGTGCAGCCTGGGGGGTCTACGAGACTCTCCT |
| | | GTGCAGCCTCTGGATTCACTTTGGATATTTATGCTATAGGCTGGTTCCGCCAGGCCCCAGGGAA |
| | | GGAGCATGAGGGGGTCTCGTGGATTGTTGGTAATGATGGTAGGACATACTACATAGACTCCGTG |
| | | AAGGGCCGATTCACCATCTCCAGAGACAACGCCAAGAACACGGTGTATCTTGAAATGAACAGC |
| | | CTGAAACCTGAGGATACAGCCGTTTATTACTGCGCAGCTAAGTTCTGGCCCCGATATTATAGTG |
| | | GTAGGCCTCCAGTAGGGAGGGATGGCTATGACTATTGGGGCCAGGGGACCCAGGTCACCGTCT |
| | | CCAGCGGCCGCTACCCGTACGACGTTCCGGACTACGGTTCCGGCCGAGCATAG |
| 231 | 1LCRV47 | CAGGTGCAGCTGCAGGAGTCTGGGGGAGGCTTGGTGCAGCCTGGCGGGTCTCTGATACTCTCCT |
| | | GTACAATCTCGGGAGCCTCGCTCCGAGACCGACGCGTCACCTGGAGTCGCCAAGGTCCAGGGA |
| | | AATCGCTTGAGATCATCGCAGTTATGGCGCCGGATTACGGGGTCCATTACTTTGGCTCCCTGGA |
| | | GGGGCGAGTTGCCGTCCGAGGAGACGTCGTCAAGAATACAGTATATCTCCAAGTAAACGCCCT |

TABLE 8-continued

Y. pestis LcrV SAb DNA Sequences

| SEQ ID NO | Name | Sequence |
|---|---|---|
| | | GAAACCCGAAGACACAGCCATCTATTGGTGCAGTATGGGGAATATCCGGGGCCTGGGGACCCA |
| | | GGTCACCGTCTCCAGCGGCCGCTACCCGTACGACGTTCCGGACTACGGTTCCGGCCGAGCATAG |

TABLE 9

F1 SAb Groups

| Group | Name | SEQ ID NO |
|---|---|---|
| 1 | 3F55, 3F85 | 168, 169 |
| 2 | 3F44 | 170 |
| 3 | 3F31, 3F61, 4F1, 4F6, 4F34 | 171-175 |
| 4 | 4F27 | 176 |
| 5 | 3F26 | 177 |
| 6 | 4F59 | 178 |
| 7 | 3F5, 4F57 | 179-180 |
| 8 | 4F75 | 181 |
| 9 | 3F59, 4F78 | 182-183 |
| 10 | 3F1, 3F65 | 184-185 |

TABLE 10

LcrV SAb Groups

| Group | Name | SEQ ID NO |
|---|---|---|
| 1 | 1LCRV32, 2LCRV4, 2LCRV3, 1LCRV52 | 204-207 |
| 2 | 1CLRV4, 1LCRV13, 2LCRV1, 1LCRV81, 1LCRV27, 1LCRV34 | 208-213 |
| 3 | 1LCRV31 | 214 |
| 4 | 1LCRV28 | 215 |
| 5 | 2LCRV11 | 216 |
| 6 | 1LCRV47 | 217 |

TABLE 11

Binding Kinetics of LcrV and F1 Sabs

| Name | SEQ ID NO | BIACORE $K_D$ (nM) | Microcal $K_D$ (nM) |
|---|---|---|---|
| 1LCRV13 | 209 | 0.00063 | 3.2 |
| 1LCRV28 | 215 | 0.19 | 0.20 |
| 1LCRV31 | 214 | 0.0019 | 0.76 |
| 1LCRV32 | 204 | 22 | 26 |
| 1LCRV47 | 217 | >1000 | no heat |
| 1LCRV81 | 211 | 3.5 | Error |
| 2LCRV11 | 216 | 8.2 | Error |
| 3F1 | 184 | 97 | 110 |
| 3F5 | 179 | 47 | 83 |
| 3F26 | 177 | — | — |
| 3F44 | 170 | — | — |
| 3F55 | 168 | 2.2 | 190 |
| 3F59 | 182 | 5.9 | no heat |
| 3F61 | 175 | 68 | 290 |
| 3F85 | 169 | 15 | 110 |
| 4F1 | 173 | 520 | error |
| 4F6 | 172 | 34 | 80 |
| 4F27 | 176 | — | — |
| 4F34 | 171 | 390 | error |
| 4F59 | 178 | 27 | 83 |
| 4F75 | 181 | 6/9 | error |
| 4F78 | 183 | 6/28 | error |

TABLE 12

Binding Constants of LcrV SAbs

| Name | SEQ ID NO | $k_a$ (M$^{-1}$ s$^{-1}$) | $k_d$ (s$^{-1}$) | $K_D$ (nM) |
|---|---|---|---|---|
| 1LCRV13 | 209 | $2.5 \times 10^5$ | $1.6 \times 10^{-6}$ | 0.00063 |
| 1LCRV28 | 215 | $4.3 \times 10^5$ | $8.1 \times 10^{-5}$ | 0.19 |
| 1LCRV31 | 214 | $1.7 \times 10^5$ | $3.1 \times 10^{-7}$ | 0.0019 |
| 1LCRV32 | 204 | $3.4 \times 10^5$ | $7.3 \times 10^{-3}$ | 22 |
| 1LCRV47 | 217 | n.b. | n.b. | — |
| 1LCRV81 | 211 | $1.8 \times 10^5$ | $6.3 \times 10^{-4}$ | 3.5 |
| 2LCRV11 | 216 | $8.8 \times 10^5$ | $7.2 \times 10^{-3}$ | 8.2 |

Although specific embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:

1. A single-domain antibody against *Yersinia pestis* (*Y. pestis*) LcrV protein comprising:
   a first framing region ("FR") sequence comprising SEQ ID No:93;
   a first complementarity determining region ("CDR") sequence comprising SEQ ID No:20;
   a second FR sequence comprising SEQ ID No:115, the first CDR sequence being positioned between the first FR sequence and the second FR sequence;
   a second CDR sequence comprising SEQ ID No:48;
   a third FR sequence comprising SEQ ID No: 138, the second CDR sequence being positioned between the second FR sequence and the third FR sequence;
   a third CDR sequence comprising SEQ ID No.72; and
   a fourth FR sequence comprising SEQ ID No:149, the third CDR sequence being positioned between the third FR sequence and the fourth FR sequence.

2. The single-domain antibody of claim 1, further comprising:
   at least one of a protein tag, a protein domain tag, or a chemical tag.

* * * * *

SEQUENCE LISTING

<160> NUMBER OF SEQ ID NOS: 231

<210> SEQ ID NO 1
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 1

Gly Arg Thr Trp Arg Ala Tyr Tyr Met Gly
1               5                   10

```
<210> SEQ ID NO 2
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 2

Gly Arg Ala Phe Ser Asn Tyr Ala Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 3

Gly Arg Thr Phe Ser Arg Tyr Ala Met Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 4

Gln Arg Thr Phe Ser Arg Tyr Ser Leu Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 5

Gly Arg Thr Phe Ser Ser His Ala Met Ala
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Generated by phage peptide display

<400> SEQUENCE: 6

Gly Arg Thr Phe Gly Arg Pro Phe Arg Tyr Thr Met Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 7

Gly Glu Thr Val Asp Asp Leu Ala Ile Gly
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 8

Gly Met Met Tyr Ile Arg Glu Ala Ile Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 9

Gly Met Met Tyr Ile Arg Tyr Thr Met Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 10

Gly Arg Ala Val Asn Arg Tyr His Met His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 11

Gly Ile Ile Phe Ser Asp Tyr Ala Leu Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 12

Ala Arg Ile Phe Ser Ile Tyr Ala Met Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 13

Gly Val Ile Ala Ser Ile Ser Val Leu Arg
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 14

Gly Thr Thr Phe Arg Ser Leu Val Met Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 15

Gly Phe Thr Phe Ser Asn Tyr Ala Met Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 16

Gly Phe Thr Phe Arg Asn Tyr Ala Met Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 17

Gly Phe Thr Phe Ser Ser Tyr Ala Met Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 18

Gly Phe Thr Phe Ser Thr Ser Ala Met Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 19

Gly Phe Thr Phe Ser Thr Asn Ala Met Ser
1               5                   10
```

```
<210> SEQ ID NO 20
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 20

Gly Phe Arg Phe Ser Ser Tyr Ala Met Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 21

Gly Leu Arg Phe Ser Ser Tyr Ala Met Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 22

Gly Phe Thr Phe Asn Trp Tyr Thr Met Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 23

Gly Ser Leu Leu Asn Ile Tyr Ala Met Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 24

Gly Gly Thr Leu Gly Tyr Tyr Ala Ile Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 25

Gly Phe Thr Leu Asp Ile Tyr Ala Ile Gly
1               5                   10
```

```
<210> SEQ ID NO 26
<211> LENGTH: 10
<212> TYPE: PRT
<213> ORGANISM: Artificial Sequence
<220> FEATURE:
<223> OTHER INFORMATION: Generated by phage peptide display

<400> SEQUENCE: 26

Gly Ala Ser Leu Arg Asp Arg Arg Val Thr
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 27

Val Met Ser Arg Ser Gly Gly Thr Thr Ser Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 28

Ala Asn Trp Arg Ser Gly Gly Leu Thr Asp Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 29

Ala Ile Ser Trp Ser Gly Ser Ser Thr Tyr Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 30

Ala Thr Thr Trp Ser Gly Ile Ser Ser Asp Tyr Ala Asp Ser Val Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Generated by phage peptide display
```

```
<400> SEQUENCE: 31

Ala Ile Arg Trp Asn Gly Asp Asn Ile His Tyr Ser Asp Ser Ala Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 32

Gly Ile Thr Arg Ser Gly Asn Asn Ile Tyr Tyr Ser Asp Ser Val Lys
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 33

Cys Ile Ser Gly Ser Asp Gly Ser Thr Tyr Tyr Ala Asp Ser Leu Ser
1               5                   10                  15

Gly

<210> SEQ ID NO 34
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 34

Phe Val Ser Ser Thr Gly Asn Pro Arg Tyr Thr Asp Ser Val Lys Gly
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 35

Val Val Ser Ser Thr Gly Asn Pro His Tyr Ala Asp Ser Val Lys Gly
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 36

Phe Ile Ser Val Gly Gly Thr Thr Asn Tyr Ala Gly Ser Val Lys Gly
1               5                   10                  15
```

```
<210> SEQ ID NO 37
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 37

Gln Ile Thr Arg Ser Gln Asn Ile Asn Tyr Thr Gly Ser Val Lys Gly
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 38

Gln Ile Thr Arg Arg Gln Asn Ile Asn Tyr Thr Gly Ser Val Lys Gly
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 39

Ala Ile Thr Thr Gly Gly Thr Thr Asn Tyr Ala Asp Ser Val Lys Gly
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 40

Ile Ile Thr Ser Gly Gly Asn Thr Arg Tyr Ala Asp Ser Val Lys Gly
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 41

Phe Ile Ser Ser Pro Gly Asp Arg Thr Arg Tyr Thr Glu Ala Val Lys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Generated by phage peptide display
```

```
<400> SEQUENCE: 42

Thr Ile Asn Ser Gly Gly Gly Ser Thr Ser Tyr Ala Tyr Ser Val Lys
1               5                   10                  15
Gly

<210> SEQ ID NO 43
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 43

Thr Ile Asn Ile Gly Gly Gly Ser Thr Ser Tyr Ala Asp Ser Val Lys
1               5                   10                  15
Gly

<210> SEQ ID NO 44
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 44

Thr Ile Asn Gly Gly Gly Gly Ile Thr Ser Tyr Ala Asp Ser Val Lys
1               5                   10                  15
Gly

<210> SEQ ID NO 45
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 45

Thr Ile Asn Ile Ala Gly Gly Ile Thr Ser Tyr Ala Asp Ser Val Lys
1               5                   10                  15
Gly

<210> SEQ ID NO 46
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 46

Thr Ile Asn Met Gly Gly Gly Thr Thr Ser Tyr Ala Asp Ser Val Lys
1               5                   10                  15
Gly

<210> SEQ ID NO 47
<211> LENGTH: 17
<212> TYPE: PRT
<213> ORGANISM: Artificial Sequence
<220> FEATURE:
<223> OTHER INFORMATION: Generated by phage peptide display
```

```
<400> SEQUENCE: 47

Thr Ile Thr Ser Ala Gly Gly Ser Ile Ser Tyr Val Asn Ser Val Lys
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 48

Ala Ile Asn Ser Asp Gly Asp Lys Thr Ser Tyr Ala Asp Ser Val Lys
1               5                   10                  15
Gly

<210> SEQ ID NO 49
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 49

Thr Ile Thr Gly Ala Ser Gly Asp Thr Lys Tyr Ala Asp Ser Val Lys
1               5                   10                  15
Gly

<210> SEQ ID NO 50
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 50

Thr Val Thr Ser Ser Gly Thr Ala Glu Tyr Ala Asp Ser Val Lys Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 51

Cys Ile Thr Ser Ser Asp Thr Ser Ala Tyr Tyr Ala Asp Ser Ala Lys
1               5                   10                  15
Gly

<210> SEQ ID NO 52
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 52

Trp Ile Val Gly Asn Asp Gly Arg Thr Tyr Tyr Ile Asp Ser Val Lys
1               5                   10                  15
Gly
```

```
<210> SEQ ID NO 53
<211> LENGTH: 16
<212> TYPE: PRT
<213> ORGANISM: Artificial Sequence
<220> FEATURE:
<223> OTHER INFORMATION: Generated by phage peptide display

<400> SEQUENCE: 53

Val Met Ala Pro Asp Tyr Gly Val His Tyr Phe Gly Ser Leu Glu Gly
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 54

Gly Gly Gly Met Tyr Gly Pro Asp Leu Tyr Gly Met Thr Tyr
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 55

Gly Gly Gly Ser Arg Trp Tyr Gly Arg Thr Thr Ala Ser Trp Tyr Asp
1               5                   10                  15

Tyr

<210> SEQ ID NO 56
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 56

Pro Ala Tyr Gly Leu Arg Pro Pro Tyr Asn Tyr
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Generated by phage peptide display

<400> SEQUENCE: 57

Gly Arg Ser Ser Trp Phe Ala Pro Trp Leu Thr Pro Tyr Glu Tyr Asp
1               5                   10                  15

Tyr

<210> SEQ ID NO 58
<211> LENGTH: 5
<212> TYPE: PRT
<213> ORGANISM: Artificial Sequence
<220> FEATURE:
<223> OTHER INFORMATION: Generated by phage peptide display
```

```
<400> SEQUENCE: 58

Gly Val Tyr Asp Tyr
1               5

<210> SEQ ID NO 59
<211> LENGTH: 7
<212> TYPE: PRT
<213> ORGANISM: Artificial Sequence
<220> FEATURE:
<223> OTHER INFORMATION: Generated by phage peptide display

<400> SEQUENCE: 59

Asp Trp Gly Trp Arg Asn Tyr
1               5

<210> SEQ ID NO 60
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 60

Glu Ile Tyr Asp Arg Arg Trp Tyr Arg Asn Asp Tyr
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Generated by phage peptide display

<400> SEQUENCE: 61

Tyr Leu Gly Ser Arg Asp Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: Generated by phage peptide display

<400> SEQUENCE: 62

Tyr Asp Gly Arg Arg Pro Pro Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: Generated by phage peptide display

<400> SEQUENCE: 63

Tyr Asp Gly Arg Arg Arg Thr Tyr
1               5

<210> SEQ ID NO 64
<211> LENGTH: 8
<212> TYPE: PRT
<213> ORGANISM: Artificial Sequence
<220> FEATURE:
<223> OTHER INFORMATION: Generated by phage peptide display
```

```
<400> SEQUENCE: 64

Tyr Asp Gly Arg Arg Ser Pro Tyr
1               5

<210> SEQ ID NO 65
<211> LENGTH: 7
<212> TYPE: PRT
<213> ORGANISM: Artificial Sequence
<220> FEATURE:
<223> OTHER INFORMATION: Generated by phage peptide display

<400> SEQUENCE: 65

Leu Val Gly Ala Lys Asp Tyr
1               5

<210> SEQ ID NO 66
<211> LENGTH: 4
<212> TYPE: PRT
<213> ORGANISM: Artificial Sequence
<220> FEATURE:
<223> OTHER INFORMATION: Generated by phage peptide display

<400> SEQUENCE: 66

Asn Gly Ile Tyr
1

<210> SEQ ID NO 67
<211> LENGTH: 6
<212> TYPE: PRT
<213> ORGANISM: Artificial Sequence
<220> FEATURE:
<223> OTHER INFORMATION: Generated by phage peptide display

<400> SEQUENCE: 67

Thr Ala Ser His Ile Pro
1               5

<210> SEQ ID NO 68
<211> LENGTH: 8
<212> TYPE: PRT
<213> ORGANISM: Artificial Sequence
<220> FEATURE:
<223> OTHER INFORMATION: Generated by phage peptide display

<400> SEQUENCE: 68

Thr Ala Arg Asp Ser Arg Asp Ser
1               5

<210> SEQ ID NO 69
<211> LENGTH: 8
<212> TYPE: PRT
<213> ORGANISM: Artificial Sequence
<220> FEATURE:
<223> OTHER INFORMATION: Generated by phage peptide display

<400> SEQUENCE: 69

Thr Ala Ala Asn Trp Ser Ala Gln
1               5

<210> SEQ ID NO 70
<211> LENGTH: 8
<212> TYPE: PRT
<213> ORGANISM: Artificial Sequence
<220> FEATURE:
<223> OTHER INFORMATION: Generated by phage peptide display
```

```
<400> SEQUENCE: 70

Thr Ala Gly Asn Trp Ser Ala Gln
1               5

<210> SEQ ID NO 71
<211> LENGTH: 6
<212> TYPE: PRT
<213> ORGANISM: Artificial Sequence
<220> FEATURE:
<223> OTHER INFORMATION: Generated by phage peptide display

<400> SEQUENCE: 71

Leu Val Asn Leu Ala Gln
1               5

<210> SEQ ID NO 72
<211> LENGTH: 21
<212> TYPE: PRT
<213> ORGANISM: Artificial Sequence
<220> FEATURE:
<223> OTHER INFORMATION: Generated by phage peptide display

<400> SEQUENCE: 72

Arg Asp Leu Tyr Cys Ser Gly Ser Met Cys Lys Asp Val Leu Gly Gly
1               5                   10                  15

Ala Arg Tyr Asp Phe
            20

<210> SEQ ID NO 73
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 73

Tyr Leu Thr Tyr Asp Ser Gly Ser Val Lys Gly Val Asn Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 74

Cys Leu Thr Tyr Asp Ser Gly Ser Val Lys Gly Val Asn Tyr
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 75

Tyr Leu Thr Tyr Asp Ser Gly Ser Ala Lys Gly Val Asn Tyr
1               5                   10

<210> SEQ ID NO 76
<211> LENGTH: 16
<212> TYPE: PRT
<213> ORGANISM: Artificial Sequence
```

```
<220> FEATURE:
<223> OTHER INFORMATION: Generated by phage peptide display

<400> SEQUENCE: 76

His Leu Arg Tyr Gly Asp Tyr Val Arg Gly Pro Pro Glu Tyr Asn Tyr
1               5                   10                  15

<210> SEQ ID NO 77
<211> LENGTH: 20
<212> TYPE: PRT
<213> ORGANISM: Artificial Sequence
<220> FEATURE:
<223> OTHER INFORMATION: Generated by phage peptide display

<400> SEQUENCE: 77

Gly Tyr Tyr Phe Arg Asp Tyr Ser Asp Ser Tyr Tyr Tyr Thr Gly Thr
1               5                   10                  15

Gly Met Lys Val
            20

<210> SEQ ID NO 78
<211> LENGTH: 20
<212> TYPE: PRT
<213> ORGANISM: Artificial Sequence
<220> FEATURE:
<223> OTHER INFORMATION: Generated by phage peptide display

<400> SEQUENCE: 78

Lys Phe Trp Pro Arg Tyr Tyr Ser Gly Arg Pro Val Gly Arg Asp
1               5                   10                  15

Gly Tyr Asp Tyr
            20

<210> SEQ ID NO 79
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 79

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 80
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 80

Gln Val Gln Leu Gln Glu Ser Gly Gly Gly Leu Val Gln Ala Gly Gly
1               5                   10                  15

Ser Leu Arg Leu Ser Cys Val Ala Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: Generated by phage peptide display
```

```
<400> SEQUENCE: 81

Gln Val Gln Leu Gln Glu Ser Gly Gly Gly Leu Val Gln Ala Gly Gly
1               5                   10                  15

Ser Leu Arg Leu Ser Cys Ala Val Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 82

Gln Val Gln Leu Gln Glu Ser Gly Gly Gly Leu Val Gln Ala Gly Gly
1               5                   10                  15

Ser Leu Lys Leu Ser Cys Thr Ala Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 83

Gln Val Gln Leu Gln Glu Ser Gly Gly Gly Leu Val Gln Ala Gly Asp
1               5                   10                  15

Ser Arg Ile Leu Ser Cys Thr Ala Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 84

Gln Val Gln Leu Gln Glu Ser Gly Gly Gly Leu Val Gln Ala Gly Gly
1               5                   10                  15

Ser Leu Arg Leu Ala Cys Ala Ala Ser
            20                  25

<210> SEQ ID NO 85
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 85

Gln Val Gln Leu Gln Glu Ser Gly Gly Gly Leu Val Gln Pro Gly Gly
1               5                   10                  15

Ser Leu Arg Leu Ser Cys Ala Val Ser
            20                  25

<210> SEQ ID NO 86
<211> LENGTH: 25
<212> TYPE: PRT
<213> ORGANISM: Artificial Sequence
<220> FEATURE:
<223> OTHER INFORMATION: Generated by phage peptide display
```

```
<400> SEQUENCE: 86

Gln Val Gln Leu Gln Glu Ser Gly Gly Gly Leu Val Arg Pro Gly Gly
1               5                   10                  15

Ser Leu Arg Leu Ser Cys Ala Val Ser
            20                  25

<210> SEQ ID NO 87
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 87

Gln Val Gln Leu Gln Glu Ser Gly Gly Gly Ser Val Gln Pro Gly Gly
1               5                   10                  15

Ser Leu Ser Leu Ser Cys Ser Ala Ser
            20                  25

<210> SEQ ID NO 88
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 88

Gln Val Gln Leu Gln Glu Ser Gly Gly Gly Leu Val Gln Pro Gly Gly
1               5                   10                  15

Ser Leu Ser Leu Ser Cys Ser Ala Ser
            20                  25

<210> SEQ ID NO 89
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 89

Gln Val Gln Leu Gln Glu Ser Gly Gly Gly Leu Val Gln Pro Gly Gly
1               5                   10                  15

Ser Leu Arg Leu Ser Cys Ser Ala Ser
            20                  25

<210> SEQ ID NO 90
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 90

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 91
<211> LENGTH: 25
<212> TYPE: PRT
<213> ORGANISM: Artificial Sequence
<220> FEATURE:
<223> OTHER INFORMATION: Generated by phage peptide display
```

```
<400> SEQUENCE: 91

Gln Val Gln Leu Gln Glu Ser Gly Gly Gly Leu Val Arg Pro Gly Gly
1               5                   10                  15

Ser Leu Arg Leu Ser Cys Glu Ala Ser
            20                  25

<210> SEQ ID NO 92
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 92

Gln Val Gln Leu Gln Glu Ser Gly Gly Gly Leu Val Gln Ser Gly Asp
1               5                   10                  15

Ser Leu Arg Leu Ser Cys Ala Ala Ser
            20                  25

<210> SEQ ID NO 93
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 93

Gln Val Gln Leu Gln Glu Ser Gly Gly Gly Met Val Glu Pro Gly Gly
1               5                   10                  15

Ser Leu Arg Leu Ser Cys Ala Ala Ser
            20                  25

<210> SEQ ID NO 94
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 94

Gln Val Gln Leu Gln Glu Ser Gly Gly Gly Leu Val Glu Pro Gly Gly
1               5                   10                  15

Ser Leu Arg Leu Ser Cys Ala Ala Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 95

Gln Val Gln Leu Gln Glu Ser Gly Gly Gly Leu Val Gln Ser Gly Glu
1               5                   10                  15

Ser Leu Arg Leu Ser Cys Ala Ala Ser
            20                  25

<210> SEQ ID NO 96
<211> LENGTH: 25
<212> TYPE: PRT
<213> ORGANISM: Artificial Sequence
<220> FEATURE:
<223> OTHER INFORMATION: Generated by phage peptide display
```

```
<400> SEQUENCE: 96

Gln Val Gln Leu Gln Glu Ser Gly Gly Gly Leu Val Gln Pro Gly Gly
1               5                   10                  15

Ser Leu Lys Leu Ser Cys Ala Ala Ser
            20                  25

<210> SEQ ID NO 97
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 97

Gln Val Gln Leu Gln Glu Ser Gly Gly Gly Leu Val Arg Pro Gly Gly
1               5                   10                  15

Ser Leu Lys Leu Ser Cys Ala Ala Ser
            20                  25

<210> SEQ ID NO 98
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 98

Gln Val Gln Leu Gln Glu Ser Gly Gly Gly Ser Val Gln Pro Gly Gly
1               5                   10                  15

Ser Leu Lys Leu Ser Cys Ala Ala Ser
            20                  25

<210> SEQ ID NO 99
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 99

Gln Val Gln Leu Gln Glu Ser Gly Gly Gly Phe Val Gln Pro Gly Gly
1               5                   10                  15

Ser Leu Lys Leu Ser Cys Ala Ala Ser
            20                  25

<210> SEQ ID NO 100
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 100

Gln Val Gln Leu Gln Glu Ser Gly Gly Gly Leu Val Gln Pro Gly Gly
1               5                   10                  15

Ser Leu Gly Leu Ser Cys Ala Ala Ser
            20                  25

<210> SEQ ID NO 101
<211> LENGTH: 25
<212> TYPE: PRT
<213> ORGANISM: Artificial Sequence
<220> FEATURE:
<223> OTHER INFORMATION: Generated by phage peptide display
```

<400> SEQUENCE: 101

Gln Val Gln Leu Gln Glu Ser Gly Gly Gly Leu Val Gln Pro Gly Gly
1               5                   10                  15

Ser Thr Arg Leu Ser Cys Ala Ala Ser
            20                  25

<210> SEQ ID NO 102
<211> LENGTH: 25
<212> TYPE: PRT
<213> ORGANISM: Artificial Sequence
<220> FEATURE:
<223> OTHER INFORMATION: Generated by phage peptide display

<400> SEQUENCE: 102

Gln Val Gln Leu Gln Glu Ser Gly Gly Gly Leu Val Gln Pro Gly Gly
1               5                   10                  15

Ser Leu Ile Leu Ser Cys Thr Ile Ser
            20                  25

<210> SEQ ID NO 103
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 103

Trp Phe Arg Gln Ala Pro Gly Lys Glu Arg Glu Phe Val Ala
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 104

Trp Phe Arg Gln Ala Pro Gly Glu Glu Arg Val Phe Val Ala
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 105

Trp Phe Arg Gln Gly Pro Gly Glu Glu Arg Gln Phe Leu Ala
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 106

Trp Phe Arg Arg Ala Pro Gly Lys Glu Arg Glu Phe Val Gly
1               5                   10

```
<210> SEQ ID NO 107
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 107

Trp Phe Arg Gln Ala Pro Gly Lys Glu Arg Glu Glu Ile Ser
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 108

Trp Tyr Arg Gln Ala Pro Gly Lys Gln Arg Glu Trp Val Ala
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 109

Trp Tyr Arg Gln Ala Pro Gly Lys Gln Arg Glu Trp Val Thr
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 110

Trp Tyr Arg Gln Thr Pro Gly Lys Thr Arg Asp Trp Val Ala
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 111

Trp Tyr Arg Gln Ala Pro Gly Lys Glu Arg Glu Trp Val Ala
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 112

Trp Val Arg Gln Ala Pro Gly Lys Gly Leu Glu Trp Val Ser
1               5                   10
```

```
<210> SEQ ID NO 113
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 113

Trp Val Arg Leu Ala Pro Gly Lys Gly Leu Glu Trp Val Ser
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 114

Trp Ile Arg Gln Pro Pro Gly Lys Ala Arg Glu Val Val Ala
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 115

Trp Val Arg Gln Ala Pro Gly Lys Gly Leu Glu Arg Val Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 116

Trp Tyr Arg Gln Val Pro Gly Glu Glu Arg Lys Met Val Ala
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 117

Trp Tyr Arg Gln Ala Pro Gly Arg Gln Arg Glu Leu Val Ala
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 118

Trp Phe Arg Gln Ala Pro Gly Lys Glu Arg Glu Ala Val Ser
1               5                   10
```

```
<210> SEQ ID NO 119
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 119

Trp Phe Arg Gln Ala Pro Gly Lys Glu His Glu Gly Val Ser
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Generated by phage peptide display

<400> SEQUENCE: 120

Trp Ser Arg Gln Gly Pro Gly Lys Ser Leu Glu Ile Ile Ala
1               5                   10

<210> SEQ ID NO 121
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 121

Arg Phe Thr Ile Ser Arg Asp Asn Ala Lys Asn Thr Val Tyr Leu Gln
1               5                   10                  15

Met Asn Asn Leu Ala Pro Glu Asp Thr Ala Thr Tyr Tyr Cys Lys Ala
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 122

Arg Phe Thr Ile Ser Arg Asp Asp Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 123

Arg Phe Thr Ile Ser Arg Asp His Ala Lys Asn Val Met Tyr Leu Gln
1               5                   10                  15

Met Asn Gly Leu Lys Pro Glu Asp Thr Gly Val Tyr Val Cys Ala Arg
            20                  25                  30

<210> SEQ ID NO 124
<211> LENGTH: 32
<212> TYPE: PRT
<213> ORGANISM: Artificial Sequence
```

```
<220> FEATURE:
<223> OTHER INFORMATION: Generated by phage peptide display

<400> SEQUENCE: 124

Arg Phe Thr Ile Ser Arg Asp Asn Ala Lys Asn Thr Gly Tyr Leu Gln
1               5                   10                  15

Met Asn Asn Leu Lys Pro Glu Asp Thr Gly Val Tyr Tyr Cys Ala Ala
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 125

Arg Phe Thr Ile Ser Arg Asp Leu Ala Lys Asn Thr Leu Tyr Leu Gln
1               5                   10                  15

Met Asn Ser Leu Lys Pro Glu Asp Thr Ala Val Tyr Tyr Cys Ala Arg
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 126

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 127

Arg Phe Thr Ile Ser Arg Asp Asn Val Lys Asn Thr Val Tyr Leu Gln
1               5                   10                  15

Met Asn Ser Leu Lys Leu Glu Asp Thr Ala Val Tyr Tyr Cys Tyr Ala
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 128

Arg Phe Thr Ile Ser Arg Asp Asn Ala Lys Asn Thr Val Tyr Leu Gln
1               5                   10                  15

Met Asn Ser Leu Thr Pro Glu Asp Thr Ala Val Tyr Tyr Cys Asn Thr
            20                  25                  30
```

```
<210> SEQ ID NO 129
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 129

Arg Phe Thr Val Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Asn Ser
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 130

Arg Phe Thr Val Ser Arg Asp Asn Ala Lys Asn Thr Val His Leu Gln
1               5                   10                  15

Met Asn Ser Leu Lys Pro Glu Asp Thr Ala Val Tyr Tyr Cys His Ala
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 131

Arg Phe Thr Val Ser Arg Asp Asn Ala Lys Asn Thr Val His Leu Gln
1               5                   10                  15

Met Asn Ser Leu Lys Pro Glu Asp Ala Ala Val Tyr Tyr Cys His Ala
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 132

Arg Phe Thr Thr Ser Arg Asp Asn Ala Arg Asn Thr Val Tyr Leu Gln
1               5                   10                  15

Met Asn Ser Leu Lys Pro Glu Asp Thr Ala Val Tyr Tyr Cys Asn Thr
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 133

Arg Phe Thr Ile Ser Arg Asp Asn Ala Lys Asn Ala Leu Tyr Leu Gln
1               5                   10                  15

Met Asn Gly Leu Lys Pro Glu Asp Thr Ala Val Tyr Tyr Cys Asn Ala
            20                  25                  30
```

```
<210> SEQ ID NO 134
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 134

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 135

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Gln
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 136

Arg Phe Thr Ile Ser Arg His Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 137

Arg Phe Thr Ile Ser Arg Asp Asn Ala Lys Asn Thr Leu Tyr Leu Gln
1               5                   10                  15

Met Asn Met Leu Lys Pro Glu Asp Thr Ala Val Tyr Tyr Cys Ala Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 138

Arg Phe Thr Ile Ser Arg Asp Asn Ala Arg Asn Thr Leu Tyr Leu Gln
1               5                   10                  15

Met Ser Asn Leu Lys Pro Glu Asp Thr Ala Val Tyr Tyr Cys Ala Asp
            20                  25                  30
```

```
<210> SEQ ID NO 139
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 139

Arg Phe Thr Ile Ser Arg Asp Asn Ala Arg Asn Thr Leu Tyr Leu Gln
1               5                   10                  15

Met Asn Asn Leu Lys Pro Glu Asp Thr Ala Val Tyr Tyr Cys Ala Asp
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 140

Arg Phe Thr Ile Ser Arg Asp Asn Ala Lys Asn Thr Val Thr Leu Gln
1               5                   10                  15

Met Asn Ser Leu Lys Pro Gly Asp Ala Ala Val Tyr Tyr Cys His Ala
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 141

Arg Phe Thr Ile Ser Arg Asp Asn Ala Lys Asn Thr Val Thr Leu Gln
1               5                   10                  15

Met Asn Ser Leu Lys Pro Gly Asp Thr Ala Val Tyr Tyr Cys His Ala
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 142

Arg Ser Thr Ile Ser Arg Asp Asn Ala Lys Asn Thr Val Thr Leu Gln
1               5                   10                  15

Met Asn Ser Leu Lys Pro Gly Asp Thr Ala Val Tyr Tyr Cys His Ala
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 143

Arg Phe Thr Ile Ser Arg Asp Asn Ala Lys Asn Thr Val Tyr Leu Gln
1               5                   10                  15

Met Asn Ser Leu Arg Pro Glu Asp Thr Gly Val Tyr Tyr Cys Asn Ala
            20                  25                  30
```

```
<210> SEQ ID NO 144
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 144

Arg Phe Thr Ile Ser Arg Asp Asn Ala Lys Asn Thr Met Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 145

Arg Phe Thr Ile Ser Arg Asp Asn Ala Lys Asn Thr Val Tyr Leu Glu
1               5                   10                  15

Met Asn Ser Leu Lys Pro Glu Asp Thr Ala Val Tyr Tyr Cys Ala Ala
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Generated by phage peptide display

<400> SEQUENCE: 146

Arg Val Ala Val Arg Gly Asp Val Val Lys Asn Thr Val Tyr Leu Gln
1               5                   10                  15

Val Asn Ala Leu Lys Pro Glu Asp Thr Ala Ile Tyr Trp Cys Ser Met
            20                  25                  30

<210> SEQ ID NO 147
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 147

Trp Gly Lys Gly Thr Gln Val Thr Val Ser Ser
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 148

Trp Gly Gln Gly Thr Gln Val Thr Val Ser Ser
1               5                   10

<210> SEQ ID NO 149
<211> LENGTH: 11
<212> TYPE: PRT
<213> ORGANISM: Artificial Sequence
```

-continued

```
<220> FEATURE:
<223> OTHER INFORMATION: Generated by phage peptide display

<400> SEQUENCE: 149

Arg Gly Gln Gly Thr Gln Val Thr Val Ser Ser
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 150

Trp Gly Arg Gly Thr Gln Val Thr Val Ser Ser
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 151

Leu Ser Gln Gly Thr Gln Val Thr Val Ser Ser
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 152

Thr Gly Gln Gly Thr Gln Val Thr Val Ser Ser
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Generated by phage peptide display

<400> SEQUENCE: 153

Arg Gly Leu Gly Thr Gln Val Thr Val Ser Ser
1               5                   10

<210> SEQ ID NO 154
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 154

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Trp Arg Ala Tyr
            20                  25                  30

Tyr Met Gly Trp Phe Arg Gln Ala Pro Gly Lys Glu Arg Glu Phe Val
        35                  40                  45
```

```
Ala Val Met Ser Arg Ser Gly Gly Thr Thr Ser Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Asn Leu Ala Pro Glu Asp Thr Ala Thr Tyr Tyr Cys
                 85                  90                  95

Lys Ala Gly Gly Gly Met Tyr Gly Pro Asp Leu Tyr Gly Met Thr Tyr
                100                 105                 110

Trp Gly Lys Gly Thr Gln Val Thr Val Ser Ser
            115                 120
```

<210> SEQ ID NO 155
<211> LENGTH: 126
<212> TYPE: PRT
<213> ORGANISM: Artificial Sequence
<220> FEATURE:
<223> OTHER INFORMATION: Generated by phage peptide display

<400> SEQUENCE: 155

```
Gln Val Gln Leu Gln Glu Ser Gly Gly Gly Leu Val Gln Ala Gly Gly
 1               5                  10                  15

Ser Leu Arg Leu Ser Cys Val Ala Ser Gly Arg Ala Phe Ser Asn Tyr
                 20                  25                  30

Ala Met Ala Trp Phe Arg Gln Ala Pro Gly Lys Glu Arg Glu Phe Val
             35                  40                  45

Ala Ala Asn Trp Arg Ser Gly Gly Leu Thr Asp Tyr Ala Asp Ser Val
     50                  55                  60

Lys Gly Arg Phe Thr Ile Ser Arg Asp Asp Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Gly Gly Gly Ser Arg Trp Tyr Gly Arg Thr Thr Ala Ser Trp
                100                 105                 110

Tyr Asp Tyr Trp Gly Gln Gly Thr Gln Val Thr Val Ser Ser
            115                 120                 125
```

<210> SEQ ID NO 156
<211> LENGTH: 120
<212> TYPE: PRT
<213> ORGANISM: Artificial Sequence
<220> FEATURE:
<223> OTHER INFORMATION: Generated by phage peptide display

<400> SEQUENCE: 156

```
Gln Val Gln Leu Gln Glu Ser Gly Gly Gly Leu Val Ala Gly Gly
 1               5                  10                  15

Ser Leu Arg Leu Ser Cys Ala Val Ser Gly Arg Thr Phe Ser Arg Tyr
                 20                  25                  30

Ala Met Gly Trp Phe Arg Gln Ala Pro Gly Lys Glu Arg Glu Phe Val
             35                  40                  45

Ala Ala Ile Ser Trp Ser Gly Ser Thr Tyr Tyr Ala Asp Ser Val
     50                  55                  60

Lys Gly Arg Phe Thr Ile Ser Arg Asp His Ala Lys Asn Val Met Tyr
 65                  70                  75                  80

Leu Gln Met Asn Gly Leu Lys Pro Glu Asp Thr Gly Val Tyr Val Cys
                 85                  90                  95
```

Ala Arg Pro Ala Tyr Gly Leu Arg Pro Pro Tyr Asn Tyr Arg Gly Gln
            100                 105                 110

Gly Thr Gln Val Thr Val Ser Ser
        115                 120

<210> SEQ ID NO 157
<211> LENGTH: 126
<212> TYPE: PRT
<213> ORGANISM: Artificial Sequence
<220> FEATURE:
<223> OTHER INFORMATION: Generated by phage peptide display

<400> SEQUENCE: 157

Gln Val Gln Leu Gln Glu Ser Gly Gly Gly Leu Val Gln Ala Gly Gly
1               5                   10                  15

Ser Leu Lys Leu Ser Cys Thr Ala Ser Gln Arg Thr Phe Ser Arg Tyr
            20                  25                  30

Ser Leu Gly Trp Phe Arg Gln Ala Pro Gly Glu Glu Arg Val Phe Val
        35                  40                  45

Ala Ala Thr Thr Trp Ser Gly Ile Ser Ser Asp Tyr Ala Asp Ser Val
    50                  55                  60

Lys Gly Arg Phe Thr Ile Ser Arg Asp Asn Ala Lys Asn Thr Gly Tyr
65                  70                  75                  80

Leu Gln Met Asn Asn Leu Lys Pro Glu Asp Thr Gly Val Tyr Tyr Cys
                85                  90                  95

Ala Ala Gly Arg Ser Ser Trp Phe Ala Pro Trp Leu Thr Pro Tyr Glu
            100                 105                 110

Tyr Asp Tyr Trp Gly Arg Gly Thr Gln Val Thr Val Ser Ser
        115                 120                 125

<210> SEQ ID NO 158
<211> LENGTH: 114
<212> TYPE: PRT
<213> ORGANISM: Artificial Sequence
<220> FEATURE:
<223> OTHER INFORMATION: Generated by phage peptide display

<400> SEQUENCE: 158

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser His
            20                  25                  30

Ala Met Ala Trp Phe Arg Gln Gly Pro Gly Glu Glu Arg Gln Phe Leu
        35                  40                  45

Ala Ala Ile Arg Trp Asn Gly Asp Asn Ile His Tyr Ser Asp Ser Ala
    50                  55                  60

Lys Gly Arg Phe Thr Ile Ser Arg Asp Leu Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Gly Val Tyr Asp Tyr Trp Gly Gln Gly Thr Gln Val Thr Val
            100                 105                 110

Ser Ser

<210> SEQ ID NO 159
<211> LENGTH: 119
<212> TYPE: PRT
<213> ORGANISM: Artificial Sequence
<220> FEATURE:
<223> OTHER INFORMATION: Generated by phage peptide display

<400> SEQUENCE: 159

Gln Val Gln Leu Gln Glu Ser Gly Gly Gly Leu Val Gln Ala Gly Asp
1               5                   10                  15

Ser Arg Ile Leu Ser Cys Thr Ala Ser Gly Arg Thr Phe Gly Arg Pro
            20                  25                  30

Phe Arg Tyr Thr Met Gly Trp Phe Arg Ala Pro Gly Lys Glu Arg
            35                  40                  45

Glu Phe Val Gly Gly Ile Thr Arg Ser Gly Asn Asn Ile Tyr Tyr Ser
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Asn Ala Asp Trp Gly Trp Arg Asn Tyr Trp Gly Gln Gly
            100                 105                 110

Thr Gln Val Thr Val Ser Ser
            115

<210> SEQ ID NO 160
<211> LENGTH: 121
<212> TYPE: PRT
<213> ORGANISM: Artificial Sequence
<220> FEATURE:
<223> OTHER INFORMATION: Generated by phage peptide display

<400> SEQUENCE: 160

Gln Val Gln Leu Gln Glu Ser Gly Gly Gly Leu Val Gln Ala Gly Gly
1               5                   10                  15

Ser Leu Arg Leu Ala Cys Ala Ala Ser Gly Glu Thr Val Asp Asp Leu
            20                  25                  30

Ala Ile Gly Trp Phe Arg Gln Ala Pro Gly Lys Glu Arg Glu Glu Ile
            35                  40                  45

Ser Cys Ile Ser Gly Ser Asp Gly Ser Thr Tyr Tyr Ala Asp Ser Leu
    50                  55                  60

Ser Gly Arg Phe Thr Ile Ser Arg Asp Asn Val Lys Asn Thr Val Tyr
65                  70                  75                  80

Leu Gln Met Asn Ser Leu Lys Leu Glu Asp Thr Ala Val Tyr Tyr Cys
                85                  90                  95

Tyr Ala Glu Ile Tyr Asp Arg Arg Trp Tyr Arg Asn Asp Tyr Trp Gly
            100                 105                 110

Gln Gly Thr Gln Val Thr Val Ser Ser
            115                 120

<210> SEQ ID NO 161
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 161
caggtgcagc tgcaggagtc tgggggagga ttggtgcagg ctgggggctc tctgagactc      60
tcctgtgcag cctctggacg cacctggaga gcctattaca tgggctggtt ccgccaggct    120
ccagggaagg agcgtgagtt tgtagcagtt atgagtcgga gcggtggcac cacatcctat    180

```
gcggactccg tgaagggccg attcaccatc tccagagaca acgccaagaa cacggtgtat    240
ctacaaatga caacctggc acctgaggac acggccacgt attattgtaa ggcggggggc    300
ggaatgtacg ggccggacct gtatggtatg acatactggg gcaaagggac ccaggtcacc    360
gtctccagcg ccgctaccc gtacgacgtt ccggactacg gttccggccg agcatag      417
```

<210> SEQ ID NO 162
<211> LENGTH: 426
<212> TYPE: DNA
<213> ORGANISM: Artificial Sequence
<220> FEATURE:
<223> OTHER INFORMATION: Generated by phage peptide display

<400> SEQUENCE: 162

```
caggtgcagc tgcaggagtc tggaggagga ttggtacagg ctgggggctc tctgagactc     60
tcctgtgtag cctctggacg cgccttcagt aattatgcga tggcctggtt ccgccaggct    120
ccagggaagg agcgtgagtt tgtagcagct aattggcgga gtggtggtct tacagactat    180
gcagactccg tgaagggccg attcaccatc tccagagacg acgccaagaa cacggtgtat    240
ctgcaaatga acagcctgaa acctgaggac acggccgttt attactgtgc cgccgggggc    300
ggtagtcgct ggtacgggcg aacaaccgca agttggtatg actactgggg ccaggggacc    360
caggtcaccg tctccagcgg ccgctaccc tacgacgttc cggactacgg ttccggccga    420
gcatag                                                             426
```

<210> SEQ ID NO 163
<211> LENGTH: 408
<212> TYPE: DNA
<213> ORGANISM: Artificial Sequence
<220> FEATURE:
<223> OTHER INFORMATION: Generated by phage peptide display

<400> SEQUENCE: 163

```
caggtgcagc tgcaggagtc tgggggagga ttggtgcagg ctgggggctc tctgagactc     60
tcctgtgcag tctctggacg caccttcagt agatatgcca tgggctggtt ccgccaggct    120
ccagggaagg agcgtgagtt tgtagcagct attagctgga gtggtagtag cacatattat    180
gcagactccg tgaagggccg attcaccatc tccagagacc acgccaagaa cgtgatgtat    240
ctgcaaatga acggcctgaa acctgaggac acgggtgttt atgtctgtgc aagaccagcg    300
tacggactcc gccccccgta taattaccgg ggccagggga cccaggtcac cgtctccagc    360
ggccgctacc cgtacgacgt tccggactac ggttccggcc gagcatag               408
```

<210> SEQ ID NO 164
<211> LENGTH: 426
<212> TYPE: DNA
<213> ORGANISM: Artificial Sequence
<220> FEATURE:
<223> OTHER INFORMATION: Generated by phage peptide display

<400> SEQUENCE: 164

```
caggtgcagc tgcaggagtc tgggggagga ttggtgcagg ctgggggctc tctgaaactc     60
tcctgcacag cctctcaacg caccttcagt cgctatagct gggctggtt ccgccaggct    120 ccaggtgagg agcgtgtttt tgtagccgct actacatgga gtggtataag cagtgactat    180
gcagactccg tgaagggccg attcaccatc tccagagaca acgccaagaa cacggggtat    240
ctgcaaatga acaatttaaa acctgaggac acggcgtttt attactgtgc agcaggacgt    300
agtagctggt tcgcccccctg gttgaccccc tatgagtatg attattgggg ccgggggacc    360
```

```
caggtcaccg tctccagcgg ccgctacccg tacgacgttc cggactacgg ttccggccga    420
gcatag                                                                426

<210> SEQ ID NO 165
<211> LENGTH: 390
<212> TYPE: DNA
<213> ORGANISM: Artificial Sequence
<220> FEATURE:
<223> OTHER INFORMATION: Generated by phage peptide display

<400> SEQUENCE: 165
caggtgcagc tgcaggagtc tgggggagga ttggtgcagg ctgggggctc tctgagactc     60
tcctgtgcag cctctggacg caccttcagt agccatgcca tggcctggtt ccgccagggt    120
ccaggagagg agcgtcagtt tctagcagct attagatgga atggtgataa catacactat    180
tcagactccg cgaagggccg attcaccatc tccagagacc tcgccaagaa cacgctctat    240
ctgcaaatga acagcctgaa acctgaggac acggccgtgt attactgtgc aaggggggtg    300
tatgactact ggggccaggg gacccaggtc accgtctcca gcggccgcta cccgtacgac    360
gttccggact acggttccgg ccgagcatag                                     390

<210> SEQ ID NO 166
<211> LENGTH: 405
<212> TYPE: DNA
<213> ORGANISM: Artificial Sequence
<220> FEATURE:
<223> OTHER INFORMATION: Generated by phage peptide display

<400> SEQUENCE: 166
caggtgcagc tgcaggagtc tgggggagga ttggtgcagg ctggggactc tcggatactc     60
tcctgtacag cctctggacg caccttggga cgccccttca gatataccat gggctggttc    120
cgccgggctc agggaaggag gcgtgagttt gtaggaggta ttacaagaag tggtaataat    180
atatactatt cagactccgt gaagggccga ttcaccatct ccagagacaa cgccaagaac    240
acggtgtatc tccaaatgaa cagcctgaaa cctgaggaca cggccgtgta ttattgtaac    300
gcagattggg ggtggaggaa ctactggggc caggggaccc aggtcaccgt ctccagcggc    360
cgctacccgt acgacgttcc ggactacggt tccggccgag catag                    405

<210> SEQ ID NO 167
<211> LENGTH: 411
<212> TYPE: DNA
<213> ORGANISM: Artificial Sequence
<220> FEATURE:
<223> OTHER INFORMATION: Generated by phage peptide display

<400> SEQUENCE: 167
caggtgcagc tgcaggagtc tgggggaggc ttggtgcagg ctgggggtc tctgagactc      60 gcctgtgcag cctctggaga gactgtcgat gatcttgcca tcggctggtt ccgccaggcc    120 cagggaagg agcgtgagga gatttcatgt attagtggta gtgatggtag cacatactat     180
gcagactccc tgtcgggccg attcaccatc tccagggaca cgtcaagaa cacggtgtat     240 ctgcaaatga acagcctgaa acttgaggac acggccgtct attactgtta tgcagagatt    300
tacgatagac gctggtatcg gaacgactac tggggccagg gacccaggt caccgtctcc     360 agcggccgct acccgtacga cgttccggac tacggttccg gccgagcata g             411
```

<210> SEQ ID NO 168
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 168

Gln Val Gln Leu Gln Glu Ser Gly Gly Gly Leu Val Gln Ala Gly Gly
1               5                   10                  15

Ser Leu Arg Leu Ser Cys Ala Val Ser Gly Met Met Tyr Ile Arg Glu
            20                  25                  30

Ala Ile Arg Trp Tyr Arg Gln Ala Pro Gly Lys Gln Arg Glu Trp Val
        35                  40                  45

Ala Phe Val Ser Ser Thr Gly Asn Pro Arg Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Thr Pro Glu Asp Thr Ala Val Tyr Tyr Cys Asn
                85                  90                  95

Thr Tyr Leu Gly Ser Arg Asp Tyr Trp Gly Gln Gly Thr Gln Val Thr
            100                 105                 110

Val Ser Ser
        115

<210> SEQ ID NO 169
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 169

Gln Val Gln Leu Gln Glu Ser Gly Gly Gly Leu Val Gln Pro Gly Gly
1               5                   10                  15

Ser Leu Arg Leu Ser Cys Ala Val Ser Gly Met Met Tyr Ile Arg Tyr
            20                  25                  30

Thr Met Arg Trp Tyr Arg Gln Ala Pro Gly Lys Gln Arg Glu Trp Val
        35                  40                  45

Ala Val Val Ser Ser Thr Gly Asn Pro His Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Thr Pro Glu Asp Thr Ala Val Tyr Tyr Cys Asn
                85                  90                  95

Thr Tyr Leu Gly Ser Arg Asp Tyr Trp Gly Gln Gly Thr Gln Val Thr
            100                 105                 110

Val Ser Ser
        115

<210> SEQ ID NO 170
<211> LENGTH: 111
<212> TYPE: PRT
<213> ORGANISM: Artificial Sequence
<220> FEATURE:
<223> OTHER INFORMATION: Generated by phage peptide display -continued

<400> SEQUENCE: 170

Gln Val Gln Leu Gln Glu Ser Gly Gly Gly Leu Val Arg Pro Gly Gly
1               5                   10                  15

Ser Leu Arg Leu Ser Cys Ala Val Ser Gly Arg Ala Val Asn Arg Tyr
            20                  25                  30

His Met His Trp Tyr Arg Gln Ala Pro Gly Lys Gln Arg Glu Trp Val
        35                  40                  45

Thr Phe Ile Ser Val Gly Thr Thr Asn Tyr Ala Gly Ser Val Lys
    50                  55                  60

Gly Arg Phe Thr Val Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asn
            85                  90                  95

Ser Ala Glu Tyr Trp Gly Gln Gly Thr Gln Val Thr Val Ser Ser
            100                 105                 110

<210> SEQ ID NO 171
<211> LENGTH: 116
<212> TYPE: PRT
<213> ORGANISM: Artificial Sequence
<220> FEATURE:
<223> OTHER INFORMATION: Generated by phage peptide display

<400> SEQUENCE: 171

Gln Val Gln Leu Gln Glu Ser Gly Gly Gly Ser Val Gln Pro Gly Gly
1               5                   10                  15

Ser Leu Ser Leu Ser Cys Ser Ala Ser Gly Ile Ile Phe Ser Asp Tyr
            20                  25                  30

Ala Leu Thr Trp Tyr Arg Gln Ala Pro Gly Lys Gln Arg Glu Trp Val
        35                  40                  45

Ala Gln Ile Thr Arg Ser Gln Asn Ile Asn Tyr Thr Gly Ser Val Lys
    50                  55                  60

Gly Arg Phe Thr Val Ser Arg Asp Asn Ala Lys Asn Thr Val His Leu
65                  70                  75                  80

Gln Met Asn Ser Leu Lys Pro Glu Asp Thr Ala Val Tyr Tyr Cys His
            85                  90                  95

Ala Tyr Asp Gly Arg Arg Pro Pro Tyr Trp Gly Gln Gly Thr Gln Val
            100                 105                 110

Thr Val Ser Ser
        115

<210> SEQ ID NO 172
<211> LENGTH: 116
<212> TYPE: PRT
<213> ORGANISM: Artificial Sequence
<220> FEATURE:
<223> OTHER INFORMATION: Generated by phage peptide display

<400> SEQUENCE: 172

Gln Val Gln Leu Gln Glu Ser Gly Gly Gly Ser Val Gln Pro Gly Gly
1               5                   10                  15

Ser Leu Ser Leu Ser Cys Ser Ala Ser Gly Ile Ile Phe Ser Asp Tyr
            20                  25                  30

Ala Leu Thr Trp Tyr Arg Gln Ala Pro Gly Lys Gln Arg Glu Trp Val
        35                  40                  45

Ala Gln Ile Thr Arg Ser Gln Asn Ile Asn Tyr Thr Gly Ser Val Lys
    50                  55                  60

Gly Arg Phe Thr Val Ser Arg Asp Asn Ala Lys Asn Thr Val His Leu
65                  70                  75                  80

Gln Met Asn Ser Leu Lys Pro Glu Asp Thr Ala Val Tyr Tyr Cys His
                85                  90                  95

Ala Tyr Asp Gly Arg Arg Arg Thr Tyr Trp Gly Gln Gly Thr Gln Val
            100                 105                 110

Thr Val Ser Ser
        115

<210> SEQ ID NO 173
<211> LENGTH: 116
<212> TYPE: PRT
<213> ORGANISM: Artificial Sequence
<220> FEATURE:
<223> OTHER INFORMATION: Generated by phage peptide display

<400> SEQUENCE: 173

Gln Val Gln Leu Gln Glu Ser Gly Gly Gly Leu Val Gln Pro Gly Gly
1               5                   10                  15

Ser Leu Ser Leu Ser Cys Ser Ala Ser Gly Ile Ile Phe Ser Asp Tyr
            20                  25                  30

Ala Leu Thr Trp Tyr Arg Gln Ala Pro Gly Lys Gln Arg Glu Trp Val
        35                  40                  45

Ala Gln Ile Thr Arg Ser Gln Asn Ile Asn Tyr Thr Gly Ser Val Lys
    50                  55                  60

Gly Arg Phe Thr Val Ser Arg Asp Asn Ala Lys Asn Thr Val His Leu
65                  70                  75                  80

Gln Met Asn Ser Leu Lys Pro Glu Asp Thr Ala Val Tyr Tyr Cys His
                85                  90                  95

Ala Tyr Asp Gly Arg Arg Pro Pro Tyr Trp Gly Gln Gly Thr Gln Val
            100                 105                 110

Thr Val Ser Ser
        115

<210> SEQ ID NO 174
<211> LENGTH: 116
<212> TYPE: PRT
<213> ORGANISM: Artificial Sequence
<220> FEATURE:
<223> OTHER INFORMATION: Generated by phage peptide display

<400> SEQUENCE: 174

Gln Val Gln Leu Gln Glu Ser Gly Gly Gly Leu Val Gln Pro Gly Gly
1               5                   10                  15

Ser Leu Ser Leu Ser Cys Ser Ala Ser Gly Ile Ile Phe Ser Asp Tyr
            20                  25                  30

Ala Leu Thr Trp Tyr Arg Gln Ala Pro Gly Lys Gln Arg Glu Trp Val
        35                  40                  45

Ala Gln Ile Thr Arg Arg Gln Asn Ile Asn Tyr Thr Gly Ser Val Lys
    50                  55                  60

Gly Arg Phe Thr Val Ser Arg Asp Asn Ala Lys Asn Thr Val His Leu
65                  70                  75                  80

Gln Met Asn Ser Leu Lys Pro Glu Asp Thr Ala Val Tyr Tyr Cys His
                85                  90                  95

Ala Tyr Asp Gly Arg Arg Ser Pro Tyr Trp Gly Gln Gly Thr Gln Val
            100                 105                 110

Thr Val Ser Ser
        115

-continued

```
<210> SEQ ID NO 175
<211> LENGTH: 116
<212> TYPE: PRT
<213> ORGANISM: Artificial Sequence
<220> FEATURE:
<223> OTHER INFORMATION: Generated by phage peptide display

<400> SEQUENCE: 175
```

Gln Val Gln Leu Gln Glu Ser Gly Gly Gly Leu Val Gln Pro Gly Gly
1               5                   10                  15

Ser Leu Arg Leu Ser Cys Ser Ala Ser Gly Ile Ile Phe Ser Asp Tyr
            20                  25                  30

Ala Leu Thr Trp Tyr Arg Gln Ala Pro Gly Lys Gln Arg Glu Trp Val
        35                  40                  45

Ala Gln Ile Thr Arg Ser Gln Asn Ile Asn Tyr Thr Gly Ser Val Lys
    50                  55                  60

Gly Arg Phe Thr Val Ser Arg Asp Asn Ala Lys Asn Thr Val His Leu
65                  70                  75                  80

Gln Met Asn Ser Leu Lys Pro Glu Asp Ala Ala Val Tyr Tyr Cys His
                85                  90                  95

Ala Tyr Asp Gly Arg Arg Pro Pro Tyr Trp Gly Gln Gly Thr Gln Val
            100                 105                 110

Thr Val Ser Ser
        115

```
<210> SEQ ID NO 176
<211> LENGTH: 111
<212> TYPE: PRT
<213> ORGANISM: Artificial Sequence
<220> FEATURE:
<223> OTHER INFORMATION: Generated by phage peptide display

<400> SEQUENCE: 176
```

Gln Val Gln Leu Gln Glu Ser Gly Gly Gly Leu Val Gln Pro Gly Gly
1               5                   10                  15

Ser Leu Arg Leu Ser Cys Ala Ala Ser Ala Arg Ile Phe Ser Ile Tyr
            20                  25                  30

Ala Met Val Trp Tyr Arg Gln Ala Pro Gly Lys Gln Arg Glu Trp Val
        35                  40                  45

Ala Ala Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Pro Gly Tyr Trp Gly Gln Gly Thr Gln Val Thr Val Ser Ser
            100                 105                 110

```
<210> SEQ ID NO 177
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 177
```

Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Ile Ala Ser Ile Ser
            20                  25                  30

Val Leu Arg Trp Tyr Arg Gln Thr Pro Gly Lys Thr Arg Asp Trp Val
            35                  40                  45

Ala Ile Ile Thr Ser Gly Gly Asn Thr Arg Tyr Ala Asp Ser Val Lys
 50                  55                  60

Gly Arg Phe Thr Thr Ser Arg Asp Asn Ala Arg Asn Thr Val Tyr Leu
 65                  70                  75                  80

Gln Met Asn Ser Leu Lys Pro Glu Asp Thr Ala Val Tyr Tyr Cys Asn
                 85                  90                  95

Thr Leu Val Gly Ala Lys Asp Tyr Trp Gly Gln Gly Thr Gln Val Thr
            100                 105                 110

Val Ser Ser
        115

<210> SEQ ID NO 178
<211> LENGTH: 113
<212> TYPE: PRT
<213> ORGANISM: Artificial Sequence
<220> FEATURE:
<223> OTHER INFORMATION: Generated by phage peptide display

<400> SEQUENCE: 178

Gln Val Gln Leu Gln Glu Ser Gly Gly Gly Leu Val Arg Pro Gly Gly
 1               5                  10                  15

Ser Leu Arg Leu Ser Cys Glu Ala Ser Gly Thr Thr Phe Arg Ser Leu
             20                  25                  30

Val Met Lys Trp Tyr Arg Gln Ala Pro Gly Lys Glu Arg Glu Trp Val
            35                  40                  45

Ala Phe Ile Ser Ser Pro Gly Asp Arg Thr Arg Tyr Thr Glu Ala Val
 50                  55                  60

Lys Gly Arg Phe Thr Ile Ser Arg Asp Asn Ala Lys Asn Ala Leu Tyr
 65                  70                  75                  80

Leu Gln Met Asn Gly Leu Lys Pro Glu Asp Thr Ala Val Tyr Tyr Cys
                 85                  90                  95

Asn Ala Asn Gly Ile Tyr Trp Gly Lys Gly Thr Gln Val Thr Val Ser
            100                 105                 110

Ser

<210> SEQ ID NO 179
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 179

Gln Val Gln Leu Gln Glu Ser Gly Gly Gly Leu Val Gln Ser Gly Asp
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
            35                  40                  45

Ser Thr Ile Asn Ser Gly Gly Gly Ser Thr Ser Tyr Ala Tyr Ser Val
             50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

```
Ala Lys Thr Ala Ser His Ile Pro Leu Ser Gln Gly Thr Gln Val Thr
            100                 105                 110

Val Ser Ser
        115

<210> SEQ ID NO 180
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 180

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Asn Ile Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Thr Ala Ser His Ile Pro Leu Ser Gln Gly Thr Gln Val Thr
            100                 105                 110

Val Ser Ser
        115

<210> SEQ ID NO 181
<211> LENGTH: 117
<212> TYPE: PRT
<213> ORGANISM: Artificial Sequence
<220> FEATURE:
<223> OTHER INFORMATION: Generated by phage peptide display

<400> SEQUENCE: 181

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Thr Ile Asn Gly Gly Gly Ile Thr Ser Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Gln Thr Ala Arg Asp Ser Arg Asp Ser Arg Gly Gln Gly Thr Gln
            100                 105                 110

Val Thr Val Ser Ser
        115

<210> SEQ ID NO 182
<211> LENGTH: 117
<212> TYPE: PRT
<213> ORGANISM: Artificial Sequence
```

<220> FEATURE:
<223> OTHER INFORMATION: Generated by phage peptide display

<400> SEQUENCE: 182

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Leu Ala Pro Gly Lys Gly Leu Glu Trp Val
        35                  40                  45

Ser Thr Ile Asn Ile Ala Gly Gly Ile Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Thr Ala Ala Asn Trp Ser Ala Gln Arg Gly Gln Gly Thr Gln
            100                 105                 110

Val Thr Val Ser Ser
        115

<210> SEQ ID NO 183
<211> LENGTH: 117
<212> TYPE: PRT
<213> ORGANISM: Artificial Sequence
<220> FEATURE:
<223> OTHER INFORMATION: Generated by phage peptide display

<400> SEQUENCE: 183

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Asn Met Gly Gly Gly Thr Thr Ser Tyr Ala Asp Ser Val
    50                  55                  60

Lys Gly Arg Phe Thr Ile Ser Arg His Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Thr Ala Gly Asn Trp Ser Ala Gln Arg Gly Gln Gly Thr Gln
            100                 105                 110

Val Thr Val Ser Ser
        115

<210> SEQ ID NO 184
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 184

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

```
Ala Met Ser Trp Ile Arg Gln Pro Pro Gly Lys Ala Arg Glu Val Val
            35                  40                  45

Ala Thr Ile Thr Ser Ala Gly Gly Ser Ile Ser Tyr Val Asn Ser Val
        50                  55                  60

Lys Gly Arg Phe Thr Ile Ser Arg Asp Asn Ala Lys Asn Thr Leu Tyr
 65                  70                  75                  80

Leu Gln Met Asn Met Leu Lys Pro Glu Asp Thr Ala Val Tyr Tyr Cys
                85                  90                  95

Ala Arg Leu Val Asn Leu Ala Gln Thr Gly Gln Gly Thr Gln Val Thr
            100                 105                 110

Val Ser Ser
        115

<210> SEQ ID NO 185
<211> LENGTH: 115
<212> TYPE: PRT
<213> ORGANISM: Artificial Sequence
<220> FEATURE:
<223> OTHER INFORMATION: Generated by phage peptide display

<400> SEQUENCE: 185

Gln Val Gln Leu Gln Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Asn
            20                  25                  30

Ala Met Ser Trp Ile Arg Gln Pro Pro Gly Lys Ala Arg Glu Val Val
            35                  40                  45

Ala Thr Ile Thr Ser Ala Gly Gly Ser Ile Ser Tyr Val Asn Ser Val
        50                  55                  60

Lys Gly Arg Phe Thr Ile Ser Arg Asp Asn Ala Lys Asn Thr Leu Tyr
 65                  70                  75                  80

Leu Gln Met Asn Met Leu Lys Pro Glu Asp Thr Ala Val Tyr Tyr Cys
                85                  90                  95

Ala Arg Leu Val Asn Leu Ala Gln Thr Gly Gln Gly Thr Gln Val Thr
            100                 105                 110

Val Ser Ser
        115

<210> SEQ ID NO 186
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 186
caggtgcagc tgcaggagtc tgggggaggc ttggtgcagg ctggggggctc tctgagactc     60 tcctgtgcag tttctggaat gatgtacatt agggaggcta tacgctggta ccgccaggct    120
ccagggaagc agcgcgagtg ggtcgccttt gtaagtagta ctggtaatcc acgctataca    180
gactccgtga agggccgatt caccatctcc agagacaacg ccaagaacac ggtgtatctg    240
caaatgaaca gcctgacacc tgaggacacg gccgtctatt actgtaatac atacttgggc    300
tcgagggact actggggcca ggggacccag gtcaccgtct ccagcggccg ctacccgtac    360
gacgttccgg actacggttc cggccgagca tag                                 393
```

<210> SEQ ID NO 187
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 187

```
caggtgcagc tgcaggagtc tggaggaggc ttggtgcagc ctgggggtc tctgagactc      60
tcctgtgcag tttctggaat gatgtacatt aggtacacta tgcgctggta ccgccaggct     120
ccagggaagc agcgcgagtg ggtcgccgtt gtaagtagta ctggtaatcc acactatgca    180
gactccgtga agggccgatt caccatctcc agagacaacg ccaagaacac ggtgtatctg    240
caaatgaaca gcctgacacc tgaggacacg gccgtctatt actgtaatac atacttgggc    300
tcgagggact actggggcca ggggacccag gtcaccgtct ccagcggccg ctacccgtac    360
gacgttccgg actacggttc cggccgagca tag                                  393
```

<210> SEQ ID NO 188
<211> LENGTH: 381
<212> TYPE: DNA
<213> ORGANISM: Artificial Sequence
<220> FEATURE:
<223> OTHER INFORMATION: Generated by phage peptide display

<400> SEQUENCE: 188

```
caggtgcagc tgcaggagtc tgggggaggc ttggtgcggc ctgggggtc tctgagactc      60
tcctgtgcag tctctggaag agccgtcaat aggtatcaca tgcactggta ccgccaggct    120
ccagggaagc agcgcgagtg ggtcacattt attagtgttg gtggtaccac aaactatgca    180
ggctccgtga agggccgatt caccgtctcc cgagacaacg ccaaaaacac gctgtatctg    240
caaatgaaca gcctgaaacc tgaggacacg gccgtctatt actgtaattc agctgaatac    300
tggggccagg ggacccaggt caccgtctcc agcggccgct acccgtacga cgttccggac    360
tacggttccg gccgagcata g                                                381
```

<210> SEQ ID NO 189
<211> LENGTH: 396
<212> TYPE: DNA
<213> ORGANISM: Artificial Sequence
<220> FEATURE:
<223> OTHER INFORMATION: Generated by phage peptide display

<400> SEQUENCE: 189

```
caggtgcagc tgcaggagtc tgggggaggc tcggtgcagc ctgggggtc tctgagcctc      60
tcctgttcag cctctggaat catcttcagt gactatgccc tgacctggta ccgccaggct    120
ccagggaagc agcgcgagtg ggttgcacag attacgcgaa gtcaaaatat aaattataca    180
ggatccgtga agggccgatt caccgtctcc agagacaacg ccaagaacac agtgcatctg    240
caaatgaaca gcctgaaacc tgaggacacg gccgtctact attgtcatgc atatgacggt    300
cgacgcccac cctactgggg ccaggggacc caggtcaccg tctccagcgg ccgctacccg    360
tacgacgttc cggactacgg ttccggccga gcatag                              396
```

<210> SEQ ID NO 190
<211> LENGTH: 396
<212> TYPE: DNA
<213> ORGANISM: Artificial Sequence
<220> FEATURE:
<223> OTHER INFORMATION: Generated by phage peptide display

<400> SEQUENCE: 190

```
caggtgcagc tgcaggagtc tgggggaggc tcggtgcagc ctgggggtc tctgagcctc    60
tcctgttcag cctctggaat catcttcagt gactatgccc tgacctggta ccgccaggct   120
ccagggaagc agcgcgagtg ggttgcacag attacgcgaa gccaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgccgaa cctactgggg ccaggggacc caggtcaccg tctccagcgg ccgctacccg   360
tacgacgttc cggactacgg ttccggccga gcatag                             396
```

<210> SEQ ID NO 191
<211> LENGTH: 396
<212> TYPE: DNA
<213> ORGANISM: Artificial Sequence
<220> FEATURE:
<223> OTHER INFORMATION: Generated by phage peptide display

<400> SEQUENCE: 191

```
caggtgcagc tgcaggagtc tgggggaggc ttggtgcagc ctgggggtc tctgagcctc    60
tcctgttcag cctctggaat catcttcagt gactatgccc tgacctggta ccgccaggct   120
ccagggaagc agcgcgagtg ggttgcacag attacgcgaa gccaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgcccac cctactgggg ccaggggacc caggtcaccg tctccagcgg ccgctacccg   360
tacgacgttc cggactacgg ttccggccga gcatag                             396
```

<210> SEQ ID NO 192
<211> LENGTH: 396
<212> TYPE: DNA
<213> ORGANISM: Artificial Sequence
<220> FEATURE:
<223> OTHER INFORMATION: Generated by phage peptide display

<400> SEQUENCE: 192

```
caggtgcagc tgcaggagtc tgggggaggc ttggtgcagc ctgggggtc tctgagcctc    60
tcctgttcag cctctggaat catcttcagt gactatgccc tgacctggta ccgccaggct   120
ccagggaagc agcgcgagtg ggttgcacag attacgcgaa ggcaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgatcac cctactgggg ccaggggacc caggtcaccg tctccagcgg ccgctacccg   360
tacgacgttc cggactacgg ttccggccga gcatag                             396
```

<210> SEQ ID NO 193
<211> LENGTH: 396
<212> TYPE: DNA
<213> ORGANISM: Artificial Sequence
<220> FEATURE:
<223> OTHER INFORMATION: Generated by phage peptide display

<400> SEQUENCE: 193

```
caggtgcagc tgcaggagtc tgggggaggc ttggtgcagc ctgggggtc tctgagactc    60
tcctgttcag cctctggaat catcttcagt gactatgccc tgacctggta ccgccaggct   120
ccagggaagc agcgcgagtg ggttgcacag attacgcgaa gtcaaaatat aaattataca   180
```

```
ggatccgtga agggccgatt caccgtctcc agagacaacg ccaagaacac agtgcatctg      240
caaatgaaca gcctgaaacc tgaggacgcg gccgtctact attgtcatgc atatgacggt      300
cgacgcccac cctactgggg ccaggggacc caggtcaccg tctccagcgg ccgctacccg      360
tacgacgttc cggactacgg ttccggccga gcatag                                396

<210> SEQ ID NO 194
<211> LENGTH: 381
<212> TYPE: DNA
<213> ORGANISM: Artificial Sequence
<220> FEATURE:
<223> OTHER INFORMATION: Generated by phage peptide display

<400> SEQUENCE: 194
caggtgcagc tgcaggagtc tgggggaggc ttggtgcagc ctgggggtc tctgagactc        60 tcctgtgcag cctctgcccg catcttcagt atctatgcca tggtatggta ccgccaggct      120
ccagggaagc agcgcgagtg ggtcgcagct attactactg gtggtaccac aaactatgca      180
gactccgtga agggccgatt caccatctcc agagacaacg ccaagaacac ggtgtatctg      240
caaatgaaca gcctgaaacc tgaggacacg gccgtctatt actgtaatgc tccgggctac      300
tggggccagg gaacccaggt caccgtctcc agcggccgct acccgtacga cgttccggac      360
tacggttccg gccgagcata g                                                381

<210> SEQ ID NO 195
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 195
caggtgcagc tgcaggagtc tgggggaggc ttggtgcagc ctgggggtc tctgagactc        60 tcctgtgcag cctctggagt catcgccagt atctccgtcc tgcgctggta ccgccaaaca      120
ccaggaaaga gcgcgactg gtcgcaatt attactagtg gtggcaacac acgctatgca        180
gactccgtga agggccgatt caccacctcc agagataacg ccaggaacac ggtgtatctg      240
caaatgaaca gcctgaaacc tgaggacacg gccgtctatt actgtaatac acttgtagga      300
gccaaggact actggggcca ggggacccag gtcaccgtct ccagcggccg ctacccgtac      360
gacgttccgg actacggttc cggccgagca tag                                    393

<210> SEQ ID NO 196
<211> LENGTH: 387
<212> TYPE: DNA
<213> ORGANISM: Artificial Sequence
<220> FEATURE:
<223> OTHER INFORMATION: Generated by phage peptide display

<400> SEQUENCE: 196
caggtgcagc tgcaggagtc tgggggaggc ttggtgcggc ctgggggatc tctaagactc        60
tcctgtgaag cctctggaac caccttcaga agcctcgtaa tgaaatggta ccgccaggct      120
ccagggaagg agcgcgagtg ggtcgcattt atttctagtc ctggtgatcg cactcgctac      180
acagaagccg tgaagggccg attcaccatc tccagagaca atgccaagaa cgcgctgtat      240
ctgcaaatga acggcctgaa acctgaggac acggccgtgt attattgtaa cgcgaacgga      300
atatactggg gcaagggac ccaggtcacc gtctccagcg gccgctaccc gtacgacgtt       360
ccggactacg gttccggccg agcatag                                           387
```

<210> SEQ ID NO 197
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 197

```
caggtgcagc tgcaggagtc tgggggaggc ttggtgcaat ctggggattc tctgagactc      60
tcctgtgcag cctctggatt caccttcagt aactatgcta tgagctgggt ccgccaggct     120
ccaggaaagg ggctcgagtg ggtctcaact attaatagtg gtggtggtag cacaagctat     180
gcgtactccg tgaagggccg attcaccatc tccagagaca cgccaagaa cacgctgtat      240
ctgcaaatga acagcctgaa acctgaggac acggccgtgt attactgtgc aaagacggcc     300
tctcacatac ccttgagcca ggggacccag gtcaccgtct ccagcggccg ctacccgtac     360
gacgttccgg actacggttc cggccgagca tag                                  393
```

<210> SEQ ID NO 198
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 198

```
caggtgcagc tgcaggagtc tgggggaggc ttggtgcaac ctgggggttc tctgagactc      60
tcctgtgcag cctctggatt caccttcagt aactatgcta tgagctgggt ccgccaggct     120
ccaggaaagg ggctcgagtg ggtctcaact attaatattg gtggtggtag cacaagctat     180
gcagactccg tgaagggccg attcaccatc tccagagaca cgccaagaa cacgctgtat      240
ctgcaaatga acagcctgaa acctgaggac acggccgtgt attactgtgc aaagacggcc     300
tctcacatac ccttgagcca ggggacccag gtcaccgtct ccagcggccg ctacccgtac     360
gacgttccgg actacggttc cggccgagca tag                                  393
```

<210> SEQ ID NO 199
<211> LENGTH: 399
<212> TYPE: DNA
<213> ORGANISM: Artificial Sequence
<220> FEATURE:
<223> OTHER INFORMATION: Generated by phage peptide display

<400> SEQUENCE: 199

```
caggtgcagc tgcaggagtc tgggggaggc ttggtgcaac ctgggggttc tctgagactc      60
tcctgtgcag cctctggatt caccttcagg aactatgcaa tgagctgggt ccgtcaggct     120
ccaggaaagg ggctcgagtg ggtctcaact attaatggtg gtggtggtat cacaagctat     180
gcagactccg tgaagggccg attcaccatc tccagagaca cgccaagaa cacaatgtat      240
ctgcaaatga acagcctgaa acctgaggac acggccgtct attactgtgc ccaaaccgcc     300
cgcgattccc gcgattcccg gggccagggg acccaggtca ccgtctccag cggccgctac     360
ccgtacgacg ttccggacta cggttccggc cgagcatag                            399
```

<210> SEQ ID NO 200
<211> LENGTH: 399
<212> TYPE: DNA
<213> ORGANISM: Artificial Sequence
<220> FEATURE:
<223> OTHER INFORMATION: Generated by phage peptide display

<400> SEQUENCE: 200

```
caggtgcagc tgcaggagtc tgggggaggc ttggtgcaac ctgggggttc tctgagactc        60
tcctgtgcag cctctggatt caccttcagt agctatgcta tgagctgggt ccgcctggct       120
ccaggaaagg ggctcgagtg gtctcaact attaatatcg ctggtggtat cacaagctat       180
gcagactccg tgaagggccg attcaccatc tccagagaca acgccaagaa cacgctgtat       240
ctgcaaatga acagcctgaa acctgaggac acggccgtgt attactgtgc aaaaacggcg       300
gccaactgga gcgcccagag aggccagggg acccaggtca ccgtctccag cggccgctac       360
ccgtacgacg ttccggacta cggttccggc cgagcatag                              399
```

<210> SEQ ID NO 201
<211> LENGTH: 399
<212> TYPE: DNA
<213> ORGANISM: Artificial Sequence
<220> FEATURE:
<223> OTHER INFORMATION: Generated by phage peptide display

<400> SEQUENCE: 201

```
caggtgcagc tgcaggagtc tgggggaggc ttggtgcaac ctgggggttc tctgagactc        60
tcctgtgcag cctctggatt caccttcagt agctatgcta tgagctgggt ccgccaggct       120
ccaggaaagg ggctcgagtg gtctcaact attaatatgg gtggtggtac cacaagctat       180
gcagactccg tgaagggccg attcaccatc tccagacaca acgccaagaa cacgctgtat       240
ctgcaaatga acagcctgaa acctgaggac acggccgtgt attactgtgc aaaaacggcg       300
ggcaactgga gcgcccagag aggccagggg acccaggtca ccgtctccag cggccgctac       360
ccgtacgacg ttccggacta cggttccggc cgagcatag                              399
```

<210> SEQ ID NO 202
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 202

```
caggtgcagc tgcaggagtc tgggggaggc ttggtgcaac ctgggggttc tctgagactg        60
tcctgtgcag cctctggatt caccttcagt acaagtgcca tgagttggat ccgccagcct       120
ccagggaagg cgcgcgaggt ggtcgcaact attactagtg ctggtggtag tataagttat       180
gtaaactccg tgaagggccg attcaccatc tccagagaca acgccaagaa cacgctgtat       240
ctgcaaatga acatgctgaa acctgaggac acggccgtgt attactgtgc ccgactggtc       300
aaccttgccc agaccggcca gggaaccag gtcaccgtct ccagcggccg ctacccgtac       360
gacgttccgg actacggttc cggccgagca tag                                    393
```

<210> SEQ ID NO 203
<211> LENGTH: 393
<212> TYPE: DNA
<213> ORGANISM: Artificial Sequence
<220> FEATURE:
<223> OTHER INFORMATION: Generated by phage peptide display

<400> SEQUENCE: 203

```
caggtgcagc tgcaggagtc tgggggaggc ctggtgcaac ctgggggttc tctgagactg        60
tcctgtgcag cctctggatt caccttcagt acaaatgcca tgagttggat ccgccagcct       120
ccagggaagg cgcgcgaggt ggtcgcaact attactagtg ctggtggtag tataagttat       180
```

-continued

```
gtaaactccg tgaagggccg attcaccatc tccagagaca acgccaagaa cacgctgtat    240
ctgcaaatga acatgctgaa acctgaggac acggccgtgt attactgtgc ccgactggtc    300
aaccttgccc agaccggcca ggggacccag gtcaccgtct ccagcggccg ctacccgtac    360
gacgttccgg actacggttc cggccgagca tag                                 393
```

```
<210> SEQ ID NO 204
<211> LENGTH: 130
<212> TYPE: PRT
<213> ORGANISM: Artificial Sequence
<220> FEATURE:
<223> OTHER INFORMATION: Generated by phage peptide display

<400> SEQUENCE: 204
```

Gln Val Gln Leu Gln Glu Ser Gly Gly Gly Met Val Glu Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Arg Val
        35                  40                  45

Ser Ala Ile Asn Ser Asp Gly Asp Lys Thr Ser Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Asn Leu Lys Pro Glu Asp Thr Ala Val Tyr Tyr Cys
                85                  90                  95

Ala Asp Arg Asp Leu Tyr Cys Ser Gly Ser Met Cys Lys Asp Val Leu
            100                 105                 110

Gly Gly Ala Arg Tyr Asp Phe Arg Gly Gln Gly Thr Gln Val Thr Val
        115                 120                 125

Ser Ser
    130

```
<210> SEQ ID NO 205
<211> LENGTH: 130
<212> TYPE: PRT
<213> ORGANISM: Artificial Sequence
<220> FEATURE:
<223> OTHER INFORMATION: Generated by phage peptide display

<400> SEQUENCE: 205
```

Gln Val Gln Leu Gln Glu Ser Gly Gly Gly Leu Val Glu Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Arg Val
        35                  40                  45

Ser Ala Ile Asn Ser Asp Gly Asp Lys Thr Ser Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Asn Leu Lys Pro Glu Asp Thr Ala Val Tyr Tyr Cys
                85                  90                  95

Ala Asp Arg Asp Leu Tyr Cys Ser Gly Ser Met Cys Lys Asp Val Leu
            100                 105                 110

```
Gly Gly Ala Arg Tyr Asp Phe Arg Gly Gln Gly Thr Gln Val Thr Val
            115                 120                 125
Ser Ser
    130

<210> SEQ ID NO 206
<211> LENGTH: 130
<212> TYPE: PRT
<213> ORGANISM: Artificial Sequence
<220> FEATURE:
<223> OTHER INFORMATION: Generated by phage peptide display

<400> SEQUENCE: 206

Gln Val Gln Leu Gln Glu Ser Gly Gly Gly Met Val Glu Pro Gly Gly
1               5                   10                  15
Ser Leu Arg Leu Ser Cys Ala Ala Ser Gly Phe Arg Phe Ser Ser Tyr
            20                  25                  30
Ala Met Ser Trp Val Arg Gln Ala Pro Gly Lys Gly Leu Glu Arg Val
        35                  40                  45
Ser Ala Ile Asn Ser Asp Gly Asp Lys Thr Ser Tyr Ala Asp Ser Val
    50                  55                  60
Lys Gly Arg Phe Thr Ile Ser Arg Asp Asn Ala Arg Asn Thr Leu Tyr
65                  70                  75                  80
Leu Gln Met Asn Asn Leu Lys Pro Glu Asp Thr Ala Val Tyr Tyr Cys
                85                  90                  95
Ala Asp Arg Asp Leu Tyr Cys Ser Gly Ser Met Cys Lys Asp Val Leu
            100                 105                 110
Gly Gly Ala Arg Tyr Asp Phe Arg Gly Gln Gly Thr Gln Val Thr Val
            115                 120                 125
Ser Ser
    130

<210> SEQ ID NO 207
<211> LENGTH: 130
<212> TYPE: PRT
<213> ORGANISM: Artificial Sequence
<220> FEATURE:
<223> OTHER INFORMATION: Generated by phage peptide display

<400> SEQUENCE: 207

Gln Val Gln Leu Gln Glu Ser Gly Gly Gly Leu Val Gln Ser Gly Glu
1               5                   10                  15
Ser Leu Arg Leu Ser Cys Ala Ala Ser Gly Leu Arg Phe Ser Ser Tyr
            20                  25                  30
Ala Met Ser Trp Val Arg Gln Ala Pro Gly Lys Gly Leu Glu Arg Val
        35                  40                  45
Ser Ala Ile Asn Ser Asp Gly Asp Lys Thr Ser Tyr Ala Asp Ser Val
    50                  55                  60
Lys Gly Arg Phe Thr Ile Ser Arg Asp Asn Ala Arg Asn Thr Leu Tyr
65                  70                  75                  80
Leu Gln Met Ser Asn Leu Lys Pro Glu Asp Thr Ala Val Tyr Tyr Cys
                85                  90                  95
Ala Asp Arg Asp Leu Tyr Cys Ser Gly Ser Met Cys Lys Asp Val Leu
            100                 105                 110
Gly Gly Ala Arg Tyr Asp Phe Arg Gly Gln Gly Thr Gln Val Thr Val
            115                 120                 125
Ser Ser
    130
```

<210> SEQ ID NO 208
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 208

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Asn Trp Tyr
            20                  25                  30

Thr Met Ala Trp Tyr Arg Gln Val Pro Gly Glu Glu Arg Lys Met Val
        35                  40                  45

Ala Thr Ile Thr Gly Ala Ser Gly Asp Thr Lys Tyr Ala Asp Ser Val
    50                  55                  60

Lys Gly Arg Phe Thr Ile Ser Arg Asp Asn Ala Lys Asn Thr Val Thr
65                  70                  75                  80

Leu Gln Met Asn Ser Leu Lys Pro Gly Asp Ala Val Tyr Tyr Cys
                85                  90                  95

His Ala Tyr Leu Thr Tyr Asp Ser Gly Ser Val Lys Gly Val Asn Tyr
            100                 105                 110

Trp Gly Gln Gly Thr Gln Val Thr Val Ser Ser
        115                 120

<210> SEQ ID NO 209
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 209

Gln Val Gln Leu Gln Glu Ser Gly Gly Gly Leu Val Arg Pro Gly Gly
1               5                   10                  15

Ser Leu Lys Leu Ser Cys Ala Ala Ser Gly Phe Thr Phe Asn Trp Tyr
            20                  25                  30

Thr Met Ala Trp Tyr Arg Gln Val Pro Gly Glu Glu Arg Lys Met Val
        35                  40                  45

Ala Thr Ile Thr Gly Ala Ser Gly Asp Thr Lys Tyr Ala Asp Ser Val
    50                  55                  60

Lys Gly Arg Phe Thr Ile Ser Arg Asp Asn Ala Lys Asn Thr Val Thr
65                  70                  75                  80

Leu Gln Met Asn Ser Leu Lys Pro Gly Asp Thr Ala Val Tyr Tyr Cys
                85                  90                  95

His Ala Tyr Leu Thr Tyr Asp Ser Gly Ser Val Lys Gly Val Asn Tyr
            100                 105                 110

Trp Gly Gln Gly Thr Gln Val Thr Val Ser Ser
        115                 120

<210> SEQ ID NO 210
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 210

Gln Val Gln Leu Gln Glu Ser Gly Gly Gly Ser Val Gln Pro Gly Gly
1               5                   10                  15

Ser Leu Lys Leu Ser Cys Ala Ala Ser Gly Phe Thr Phe Asn Trp Tyr
            20                  25                  30

Thr Met Ala Trp Tyr Arg Gln Val Pro Gly Glu Glu Arg Lys Met Val
        35                  40                  45

Ala Thr Ile Thr Gly Ala Ser Gly Asp Thr Lys Tyr Ala Asp Ser Val
    50                  55                  60

Lys Gly Arg Phe Thr Ile Ser Arg Asp Asn Ala Lys Asn Thr Val Thr
65                  70                  75                  80

Leu Gln Met Asn Ser Leu Lys Pro Gly Asp Thr Ala Val Tyr Tyr Cys
                85                  90                  95

His Ala Tyr Leu Thr Tyr Asp Ser Gly Ser Val Lys Val Asn Tyr
            100                 105                 110

Trp Gly Gln Gly Thr Gln Val Thr Val Ser Ser
        115                 120

<210> SEQ ID NO 211
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 211

Gln Val Gln Leu Gln Glu Ser Gly Gly Gly Ser Val Gln Pro Gly Gly
1               5                   10                  15

Ser Leu Lys Leu Ser Cys Ala Ala Ser Gly Phe Thr Phe Asn Trp Tyr
            20                  25                  30

Thr Met Ala Trp Tyr Arg Gln Val Pro Gly Glu Glu Arg Lys Met Val
        35                  40                  45

Ala Thr Ile Thr Gly Ala Ser Gly Asp Thr Lys Tyr Ala Asp Ser Val
    50                  55                  60

Lys Gly Arg Ser Thr Ile Ser Arg Asp Asn Ala Lys Asn Thr Val Thr
65                  70                  75                  80

Leu Gln Met Asn Ser Leu Lys Pro Gly Asp Thr Ala Val Tyr Tyr Cys
                85                  90                  95

His Ala Cys Leu Thr Tyr Asp Ser Gly Ser Val Lys Val Asn Tyr
            100                 105                 110

Trp Gly Gln Gly Thr Gln Val Thr Val Ser Ser
        115                 120

<210> SEQ ID NO 212
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 212

Gln Val Gln Leu Gln Glu Ser Gly Gly Gly Phe Val Gln Pro Gly Gly
1               5                   10                  15

Ser Leu Lys Leu Ser Cys Ala Ala Ser Gly Phe Thr Phe Asn Trp Tyr
            20                  25                  30

Thr Met Ala Trp Tyr Arg Gln Val Pro Gly Glu Glu Arg Lys Met Val
        35                  40                  45

Ala Thr Ile Thr Gly Ala Ser Gly Asp Thr Lys Tyr Ala Asp Ser Val
            50                  55                  60

Lys Gly Arg Phe Thr Ile Ser Arg Asp Asn Ala Lys Asn Thr Val Thr
 65                  70                  75                  80

Leu Gln Met Asn Ser Leu Lys Pro Gly Asp Thr Ala Val Tyr Tyr Cys
                 85                  90                  95

His Ala Tyr Leu Thr Tyr Asp Ser Gly Ser Val Lys Gly Val Asn Tyr
            100                 105                 110

Trp Gly Gln Gly Thr Gln Val Thr Val Ser Ser
            115                 120

<210> SEQ ID NO 213
<211> LENGTH: 123
<212> TYPE: PRT
<213> ORGANISM: Artificial Sequence
<220> FEATURE:
<223> OTHER INFORMATION: Generated by phage peptide display

<400> SEQUENCE: 213

Gln Val Gln Leu Gln Glu Ser Gly Gly Gly Leu Val Gln Pro Gly Gly
  1               5                  10                  15

Ser Leu Lys Leu Ser Cys Ala Ala Ser Gly Phe Thr Phe Asn Trp Tyr
                 20                  25                  30

Thr Met Ala Trp Tyr Arg Gln Val Pro Gly Glu Glu Arg Lys Met Val
             35                  40                  45

Ala Thr Ile Thr Gly Ala Ser Gly Asp Thr Lys Tyr Ala Asp Ser Val
            50                  55                  60

Lys Gly Arg Phe Thr Ile Ser Arg Asp Asn Ala Lys Asn Thr Val Thr
 65                  70                  75                  80

Leu Gln Met Asn Ser Leu Lys Pro Gly Asp Thr Ala Val Tyr Tyr Cys
                 85                  90                  95

His Ala Tyr Leu Thr Tyr Asp Ser Gly Ser Ala Lys Gly Val Asn Tyr
            100                 105                 110

Trp Gly Gln Gly Thr Gln Val Thr Val Ser Ser
            115                 120

<210> SEQ ID NO 214
<211> LENGTH: 124
<212> TYPE: PRT
<213> ORGANISM: Artificial Sequence
<220> FEATURE:
<223> OTHER INFORMATION: Generated by phage peptide display

<400> SEQUENCE: 214

Gln Val Gln Leu Gln Glu Ser Gly Gly Gly Leu Val Gln Pro Gly Gly
  1               5                  10                  15

Ser Leu Gly Leu Ser Cys Ala Ala Ser Gly Ser Leu Leu Asn Ile Tyr
                 20                  25                  30

Ala Met Gly Trp Tyr Arg Gln Ala Pro Gly Arg Gln Arg Glu Leu Val
             35                  40                  45

Ala Thr Val Thr Ser Ser Gly Thr Ala Glu Tyr Ala Asp Ser Val Lys
            50                  55                  60

Gly Arg Phe Thr Ile Ser Arg Asp Asn Ala Lys Asn Thr Val Tyr Leu
 65                  70                  75                  80

Gln Met Asn Ser Leu Arg Pro Glu Asp Thr Gly Val Tyr Tyr Cys Asn
                 85                  90                  95

```
Ala His Leu Arg Tyr Gly Asp Tyr Val Arg Gly Pro Pro Glu Tyr Asn
            100                 105                 110

Tyr Trp Gly Gln Gly Thr Gln Val Thr Val Ser Ser
        115                 120

<210> SEQ ID NO 215
<211> LENGTH: 129
<212> TYPE: PRT
<213> ORGANISM: Artificial Sequence
<220> FEATURE:
<223> OTHER INFORMATION: Generated by phage peptide display

<400> SEQUENCE: 215

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Leu Gly Tyr Tyr
            20                  25                  30

Ala Ile Gly Trp Phe Arg Gln Ala Pro Gly Lys Glu Arg Glu Ala Val
        35                  40                  45

Ser Cys Ile Thr Ser Ser Asp Thr Ser Ala Tyr Tyr Ala Asp Ser Ala
    50                  55                  60

Lys Gly Arg Phe Thr Ile Ser Arg Asp Asn Ala Lys Asn Thr Met Tyr
65                  70                  75                  80

Leu Gln Met Asn Asn Leu Lys Pro Glu Asp Thr Ala Val Tyr Tyr Cys
                85                  90                  95

Ala Ala Gly Tyr Tyr Phe Arg Asp Tyr Ser Asp Ser Tyr Tyr Tyr Thr
            100                 105                 110

Gly Thr Gly Met Lys Val Trp Gly Lys Gly Thr Gln Val Thr Val Ser
        115                 120                 125

Ser

<210> SEQ ID NO 216
<211> LENGTH: 129
<212> TYPE: PRT
<213> ORGANISM: Artificial Sequence
<220> FEATURE:
<223> OTHER INFORMATION: Generated by phage peptide display

<400> SEQUENCE: 216

Gln Val Gln Leu Gln Glu Ser Gly Gly Gly Leu Val Gln Pro Gly Gly
1               5                   10                  15

Ser Thr Arg Leu Ser Cys Ala Ala Ser Gly Phe Thr Leu Asp Ile Tyr
            20                  25                  30

Ala Ile Gly Trp Phe Arg Gln Ala Pro Gly Lys Glu His Glu Gly Val
        35                  40                  45

Ser Trp Ile Val Gly Asn Asp Gly Arg Thr Tyr Tyr Ile Asp Ser Val
    50                  55                  60

Lys Gly Arg Phe Thr Ile Ser Arg Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Ala Ala Lys Phe Trp Pro Arg Tyr Tyr Ser Gly Arg Pro Pro Val Gly
            100                 105                 110

Arg Asp Gly Tyr Asp Tyr Trp Gly Gln Gly Thr Gln Val Thr Val Ser
        115                 120                 125

Ser
```

<210> SEQ ID NO 217
<211> LENGTH: 111
<212> TYPE: PRT
<213> ORGANISM: Artificial Sequence
<220> FEATURE:
<223> OTHER INFORMATION: Generated by phage peptide display

<400> SEQUENCE: 217

```
Gln Val Gln Leu Gln Glu Ser Gly Gly Gly Leu Val Gln Pro Gly Gly
1               5                   10                  15

Ser Leu Ile Leu Ser Cys Thr Ile Ser Gly Ala Ser Leu Arg Asp Arg
            20                  25                  30

Arg Val Thr Trp Ser Arg Gln Gly Pro Gly Lys Ser Leu Glu Ile Ile
        35                  40                  45

Ala Val Met Ala Pro Asp Tyr Gly Val His Tyr Phe Gly Ser Leu Glu
    50                  55                  60

Gly Arg Val Ala Val Arg Gly Asp Val Val Lys Asn Thr Val Tyr Leu
65                  70                  75                  80

Gln Val Asn Ala Leu Lys Pro Glu Asp Thr Ala Ile Tyr Trp Cys Ser
                85                  90                  95

Met Gly Asn Ile Arg Gly Leu Gly Thr Gln Val Thr Val Ser Ser
            100                 105                 110
```

<210> SEQ ID NO 218
<211> LENGTH: 438
<212> TYPE: DNA
<213> ORGANISM: Artificial Sequence
<220> FEATURE:
<223> OTHER INFORMATION: Generated by phage peptide display

<400> SEQUENCE: 218

| | |
|---|---|
| caggtgcagc tgcaggagtc tgggggaggc atggtagaac ctgggggttc tctgagactc | 60 |
| tcctgtgcag cctctggatt ccgcttcagt agtatgctga tgagttgggt ccgccaggct | 120 |
| ccaggaaagg ggctcgagcg ggtctcggct attaatagtg atggtgataa acaagctat | 180 |
| gcagactccg tgaagggccg atttaccatc tccagagaca acgccaggaa cacgctgtat | 240 |
| ctgcaaatga gcaacctgaa acctgaagac acggccgtgt attactgtgc agaccgagat | 300 |
| ttgtactgtt caggctctat gtgtaaggac gtcttggggg gagcacgcta tgactttcgg | 360 |
| ggccagggga cccaggtcac cgtctccagc ggccgctacc cgtacgacgt tccggactac | 420 |
| ggttccggcc gagcatag | 438 |

<210> SEQ ID NO 219
<211> LENGTH: 438
<212> TYPE: DNA
<213> ORGANISM: Artificial Sequence
<220> FEATURE:
<223> OTHER INFORMATION: Generated by phage peptide display

<400> SEQUENCE: 219

| | |
|---|---|
| caggtgcagc tgcaggagtc tggaggaggc ttggtagaac ctgggggttc tctgagactc | 60 |
| tcctgtgcag cctctggatt ccgcttcagt agtatgctga tgagttgggt ccgccaggct | 120 |
| ccaggaaagg ggctcgagcg ggtctcagct attaatagtg atggtgataa acaagctat | 180 |
| gcagactccg tgaagggccg atttaccatc tccagagaca acgccaggaa cacgctgtat | 240 |
| ctgcaaatga gcaacctgaa acctgaagac acggccgtgt attactgtgc agaccgagat | 300 |
| ttgtactgtt caggctctat gtgtaaggac gtcttggggg gagcacgcta tgactttcgg | 360 |

```
ggccagggga cccaggtcac cgtctccagc ggccgctacc cgtacgacgt tccggactac      420
ggttccggcc gagcatag                                                    438
```

<210> SEQ ID NO 220
<211> LENGTH: 438
<212> TYPE: DNA
<213> ORGANISM: Artificial Sequence
<220> FEATURE:
<223> OTHER INFORMATION: Generated by phage peptide display

<400> SEQUENCE: 220

```
caggtgcagc tgcaggagtc tgggggaggc atggtagaac ctggggggttc tctgagactc      60 tcttgtgcag cctctggatt ccgcttcagt agttatgcta tgagttgggt ccgccaggct     120
ccaggaaagg ggctcgagcg ggtctcggct attaatagtg atggtgataa acaagctat      180 gcagactccg tgaagggccg attcaccatc tccagagaca acgccaggaa cacgctgtat     240
ctgcaaatga acaacctgaa acctgaagac acggccgtgt attactgtgc agaccgagat     300
ttgtactgtt cgggctctat gtgtaaggac gtcttggggg gagcacgcta tgactttcgg     360
ggccagggga cccaggtcac cgtctccagc ggccgctacc cgtacgacgt tccggactac     420
ggttccggcc gagcatag                                                   438
```

<210> SEQ ID NO 221
<211> LENGTH: 438
<212> TYPE: DNA
<213> ORGANISM: Artificial Sequence
<220> FEATURE:
<223> OTHER INFORMATION: Generated by phage peptide display

<400> SEQUENCE: 221

```
caggtgcagc tgcaggagtc tgggggaggc ttggtgcagt ctggcgagtc tctcagactc       60
tcctgtgcag cctctggact ccgcttcagt agttatgcta tgagttgggt ccgccaggct     120
ccaggaaagg ggctcgagcg ggtctcggct attaatagtg atggtgataa acaagctat      180 gcagactccg tgaagggccg atttaccatc tccagagaca acgccaggaa cacgctgtat     240
ctgcaaatga gcaacctgaa acctgaagac acggccgtgt attactgtgc agaccgagat     300
ttgtactgtt caggctctat gtgtaaggac gtcttggggg gagcacgcta tgactttcgg     360
ggccagggga cccaggtcac cgtctccagc ggccgctacc cgtacgacgt tccggactac     420
ggttccggcc gagcatag                                                   438
```

<210> SEQ ID NO 222
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 222

```
caggtgcagc tgcaggagtc tggaggaggc ctggtgcagc ctgggggtc tctgaaactc        60 tcctgtgcag cctctggatt caccttcaat ggtatacca tggcctggta tcgccaggtt      120
ccaggggagg agcgcaaaat ggtcgccaca attacaggtg ctagtggtga cacaaaatat     180
gcagactccg tgaagggccg gttcaccatc tccagagaca atgccaagaa cacggtgaca     240
ctgcaaatga acagccttaa acctggagac gcggccgtct attactgtca tgcctaccta     300
acctacgact cggggtccgt caaaggagtt aactactggg gccaggggac ccaggtcacc     360
gtctccagcg gccgctaccc gtacgacgtt ccggactacg gttccggccg agcatag        417
```

<210> SEQ ID NO 223
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 223

```
caggtgcagc tgcaggagtc tgggggaggc ttggtgcggc ctggggggtc tctgaaactc      60
tcctgtgcag cctctggatt caccttcaat tggtatacca tggcctggta tcgccaggtt     120
ccagggagg agcgcaaaat ggtcgccaca attacaggtg ctagtggtga cacaaaatat     180
gcagactccg tgaagggccg gttcaccatc tccagagaca tgccaagaa cacggtgaca     240
ctgcaaatga acagccttaa acctggagac acggccgtct attactgtca tgcctaccta     300
acctacgact cggggtccgt caaaggagtt aactactggg gccaggggac ccaggtcacc     360
gtctccagcg gccgctaccc gtacgacgtt ccggactacg gttccggccg agcatag       417
```

<210> SEQ ID NO 224
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 224

```
caggtgcagc tgcaggagtc tgggggaggc tcggtgcagc ctggggggtc tctgaaactc      60
tcctgtgcag cctctggatt caccttcaat tggtatacca tggcctggta tcgccaggtt     120
ccagggagg agcgcaaaat ggttgccaca attacaggtg ctagtggtga cacaaaatat     180
gcagactccg tgaagggccg gttcaccatc tccagagaca tgccaagaa cacggtgaca     240
ctgcaaatga acagccttaa acctggagac acggccgtct attactgtca tgcctaccta     300
acctacgact cggggtccgt caaaggagtt aactactggg gccaggggac ccaggtcacc     360
gtctccagcg gccgctaccc gtacgacgtt ccggactacg gttccggccg agcatag       417
```

<210> SEQ ID NO 225
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 225

```
caggtgcagc tgcaggagtc tgggggaggc tcggtgcagc ctggggggtc tctgaaactc      60
tcctgtgcag cctctggatt caccttcaat tggtatacca tggcctggta tcgccaggtt     120
ccagggagg agcgcaaaat ggtcgccaca attacaggtg ctagtggtga cacaaaatat     180
gcagactccg tgaagggccg gtccaccatc tccagagaca tgccaagaa cacggtgaca     240
ctgcaaatga acagccttaa acctggagac acggccgtct attactgtca tgcctgccta     300
acctacgact cggggtccgt caaaggagtt aactactggg gtcaggggac ccaggtcacc     360
gtctccagcg gccgctaccc gtacgacgtt ccggactacg gttccggccg agcatag       417
```

<210> SEQ ID NO 226
<211> LENGTH: 417
<212> TYPE: DNA
<213> ORGANISM: Artificial Sequence
<220> FEATURE:
<223> OTHER INFORMATION: Generated by phage peptide display

```
<400> SEQUENCE: 226
caggtgcagc tgcaggagtc tgggggaggc ttcgtgcagc ctgggggtc tctgaaactc      60 tcctgtgcag cctctggatt caccttcaat tggtatacca tggcctggta tcgccaggtt    120
ccaggggagg agcgcaaaat ggtcgccaca attacaggtg ctagtggtga cacaaaatat    180
gcagactccg tgaagggccg gttcaccatc tccagagaca atgccaagaa cacggtgaca    240
ctgcaaatga acagccttaa acctggagac acggccgtct attactgtca tgcctaccta    300
acctacgact cggggtccgt caaggagtt aactactggg gccaggggac ccaggtcacc    360
gtctccagcg ccgctaccc gtacgacgtt ccggactacg gttccggccg agcatag       417

<210> SEQ ID NO 227
<211> LENGTH: 417
<212> TYPE: DNA
<213> ORGANISM: Artificial Sequence
<220> FEATURE:
<223> OTHER INFORMATION: Generated by phage peptide display

<400> SEQUENCE: 227
caggtgcagc tgcaggagtc tgggggaggc ctggtgcagc ctgggggtc tctgaaactc      60 tcctgtgcag cctctggatt caccttcaat tggtatacca tggcctggta tcgccaggtt    120
ccaggggagg agcgcaaaat ggtcgccaca attacaggtg ctagtggtga cacaaaatat    180
gcagactccg tgaagggccg gttcaccatc tccagagaca atgccaagaa cacggtgaca    240
ctgcaaatga acagccttaa acctggagac acggccgtct attactgtca tgcctaccta    300
acctacgact cggggtccgc caaggagtt aactactggg gccaggggac ccaggtcacc    360
gtctccagcg ccgctaccc gtacgacgtt ccggactacg gttccggccg agcatag       417

<210> SEQ ID NO 228
<211> LENGTH: 420
<212> TYPE: DNA
<213> ORGANISM: Artificial Sequence
<220> FEATURE:
<223> OTHER INFORMATION: Generated by phage peptide display

<400> SEQUENCE: 228
caggtgcagc tgcaggagtc tgggggaggc ttggtgcagc ctgggggtc tctaggactc      60 tcctgtgcag cctctggaag cctcttaaat atctatgcca tggctgtta ccgccaggct    120 ccagggagac agcgcgagtt ggtcgcaact gtaacgagta gtggaaccgc agaatatgca    180
gactccgtga agggccgatt caccatctct agagacaacg ccaagaacac ggtgtatctg    240
caaatgaaca gcctgagacc tgaggacacg gccgtctatt actgtaatgc acatctcaga    300
tatggcgact atgtccgtgg ccctccggag tataactact ggggccaggg gacccaggtc    360
accgtctcca gcggccgcta cccgtacgac gttccggact acggttccgg ccgagcatag    420

<210> SEQ ID NO 229
<211> LENGTH: 435
<212> TYPE: DNA
<213> ORGANISM: Artificial Sequence
<220> FEATURE:
<223> OTHER INFORMATION: Generated by phage peptide display

<400> SEQUENCE: 229
caggtgcagc tgcaggagtc tgggggaggc ttggtgcagc ctgggggtc tctgagactc      60 tcctgtgcag cctctggagg cactttgggt tactatgcca taggctggtt ccgccaggcc    120
ccagggaagg agcgcgaggc ggtctcctgt attactagta gtgacactag cgcatactat    180
```

```
gcagactccg cgaagggccg attcaccatc tccagagaca acgccaagaa cacgatgtat    240
ctgcaaatga acaacctgaa acctgaggac acagccgttt attactgtgc agccggttac    300
tattttagag actatagtga cagttactac tacacgggga cgggtatgaa agtctggggc    360
aaagggaccc aggtcaccgt ctccagcggc cgctacccgt acgacgttcc ggactacggt    420
tccggccgag catag                                                    435

<210> SEQ ID NO 230
<211> LENGTH: 435
<212> TYPE: DNA
<213> ORGANISM: Artificial Sequence
<220> FEATURE:
<223> OTHER INFORMATION: Generated by phage peptide display

<400> SEQUENCE: 230
caggtgcagc tgcaggagtc tgggggaggc ttggtgcagc ctgggggtc tacgagactc     60 tcctgtgcag cctctggatt cactttggat atttatgcta taggctggtt ccgccaggcc   120
ccagggaagg agcatgaggg ggtctcgtgg attgttggta atgatggtag gacatactac   180
atagactccg tgaagggccg attcaccatc tccagagaca acgccaagaa cacggtgtat   240
cttgaaatga acagcctgaa acctgaggat acagccgttt attactgcgc agctaagttc   300
tggccccgat attatagtgg taggcctcca gtagggaggg atggctatga ctattgggc    360 caggggaccc aggtcaccgt ctccagcggc cgctacccgt acgacgttcc ggactacggt   420
tccggccgag catag                                                   435

<210> SEQ ID NO 231
<211> LENGTH: 381
<212> TYPE: DNA
<213> ORGANISM: Artificial Sequence
<220> FEATURE:
<223> OTHER INFORMATION: Generated by phage peptide display

<400> SEQUENCE: 231
caggtgcagc tgcaggagtc tgggggaggc ttggtgcagc ctggcgggtc tctgatactc     60
tcctgtacaa tctcgggagc ctcgctccga gaccgacgcg tcacctggag tgccaaggt    120 ccagggaaat cgcttgagat catcgcagtt atggcgccgg attacggggt ccattacttt   180
ggctccctgg aggggcgagt tgccgtccga ggagacgtcg tcaagaatac agtatatctc   240
caagtaaacg ccctgaaacc cgaagacaca gccatctatt ggtgcagtat ggggaatatc   300
cggggcctgg ggacccaggt caccgtctcc agcggccgct acccgtacga cgttccggac   360
tacggttccg gccgagcata g                                             381
```